(12) United States Patent
Kling et al.

(10) Patent No.: US 9,051,304 B2
(45) Date of Patent: Jun. 9, 2015

(54) CARBOXAMIDE COMPOUNDS AND THEIR USE AS CALPAIN INHIBITORS V

(75) Inventors: Andreas Kling, Ludwigshafen (DE);
Katja Jantos, Lugwigshafen (DE);
Helmut Mack, Ludwigshafen (DE);
Achim Möller, Ludwigshafen (DE);
Wilfried Hornberger, Ludwigshafen (DE); Gisela Backfisch, Ludwigshafen (DE); Yanbin Lao, Abbott Park, IL (US); Marjoleen Nijsen, Abbott Park, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 220 days.

(21) Appl. No.: 12/972,663

(22) Filed: Dec. 20, 2010

(65) Prior Publication Data

US 2011/0152265 A1 Jun. 23, 2011

Related U.S. Application Data

(60) Provisional application No. 61/410,414, filed on Nov. 5, 2010, provisional application No. 61/288,935, filed on Dec. 22, 2009.

(51) Int. Cl.
| | |
|---|---|
| *C07D 401/04* | (2006.01) |
| *C07D 401/14* | (2006.01) |
| *C07D 207/28* | (2006.01) |
| *C07D 409/14* | (2006.01) |
| *C07D 417/14* | (2006.01) |

(52) U.S. Cl.
CPC ............ *C07D 401/14* (2013.01); *C07D 401/04* (2013.01); *C07D 207/28* (2013.01); *C07D 409/14* (2013.01); *C07D 417/14* (2013.01)

(58) Field of Classification Search
CPC .................................................... C07D 401/04
USPC ............................ 546/275.4, 276.1; 514/341
See application file for complete search history.

(56) References Cited

U.S. PATENT DOCUMENTS

| | | | |
|---|---|---|---|
| 6,380,220 | B1 | 4/2002 | Lubisch et al. |
| 6,436,949 | B1 | 8/2002 | Lubisch et al. |
| 6,448,254 | B1 | 9/2002 | Lubisch et al. |
| 6,482,832 | B1 | 11/2002 | Lubisch et al. |
| 6,562,827 | B1 | 5/2003 | Lubisch et al. |
| 6,630,493 | B1 | 10/2003 | Lubisch et al. |

(Continued)

FOREIGN PATENT DOCUMENTS

| | | |
|---|---|---|
| CA | 2328720 | 10/1999 |
| WO | 98/16512 | 4/1998 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*
Saez, M.E., et al. "Drug Discovery Today", 2006, 11(19/20), pp. 917-923.
Suzuki, K., et al., Biol. Chem. Hoppe-Seyler, 1995, 376(9), pp. 523-529.
Barrett, M.J., et al. Life Sci. 1991, 48, pp. 1659-1669.
Wang, K., et al., Trends in Pharmacol. Sci. 1994, 15, pp. 412-419.
Medana, et al., Neuropath and Appl. Neurobiol. 2007, 33, pp. 179-192.
Hong, Seung-Chyul, et al., Stroke, 1994, 25(3), pp. 663-669.
Bartus, R.T., et al., Neurological Res. 1995, 17, pp. 249-258.
Saatman, K.E., et al., Proc. Natl. Acad. Sci. USA, 1996, 93, pp. 3428-3433.
Edelstein, C.L., et al., Proc. Natl. Acad. Sci, USA, 1995, 92, pp. 7662-7666.

(Continued)

*Primary Examiner* — Patricia L Morris
(74) *Attorney, Agent, or Firm* — Lisa V. Mueller; Michael Best & Friedrich LLP

(57) ABSTRACT

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.
The carboxamide compounds are compounds of the general formula I

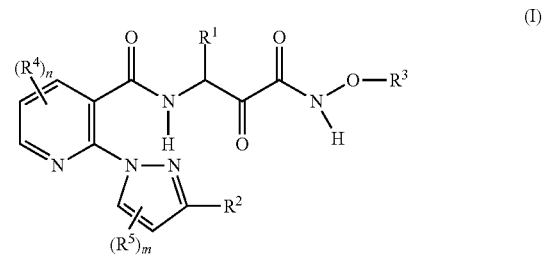

in which $R^1$, $R^2$, $R^3$, $R^4$, $R^5$, m and n have the meanings mentioned in the claims and the description, the tautomers thereof, the hydrates thereof and the pharmaceutically suitable salts thereof. Of these compounds those are preferred wherein $R^1$ is optionally substituted phenyl-$C_1$-$C_2$-alkyl or hetaryl-$C_1$-$C_2$-alkyl, $R^2$ is optionally substituted aryl, hetaryl, aryl-$C_1$-$C_6$-alkyl, aryl-$C_2$-$C_6$-alkenyl or hetaryl-$C_1$-$C_4$-alkyl, $R^3$ is $C_1$-$C_3$-alkyl, $C_1$-$C_3$-haloalkyl, $C_2$-$C_4$-alkenyl, $C_3$-$C_6$-cycloalkyl, $C_3$-$C_6$-cycloalkyl-$C_1$-$C_2$-alkyl, or phenyl-$C_1$-$C_3$-alkyl, $R^4$ and $R^5$ independently of one another are halogen, $CF_3$, $CHF_2$, $CH_2F$, $C_1$-$C_2$-alkyl or $C_1$-$C_2$-alkoxy, and m and n independently of one another are 0 or 1.

11 Claims, No Drawings

(56) References Cited

U.S. PATENT DOCUMENTS

| | | |
|---|---|---|
| 2010/0216844 A1 | 8/2010 | Kling et al. |
| 2010/0286146 A1 | 11/2010 | Mack et al. |

FOREIGN PATENT DOCUMENTS

| | | |
|---|---|---|
| WO | 98/25899 | 6/1998 |
| WO | 99/17775 | 4/1999 |
| WO | 99/54294 | 10/1999 |
| WO | 99/54304 | 10/1999 |
| WO | 99/54305 | 10/1999 |
| WO | 99/61423 | 12/1999 |
| WO | 03/080182 | 10/2003 |
| WO | 2007/016589 | 2/2007 |
| WO | 2008/080969 | 7/2008 |
| WO | 2008/106130 | 9/2008 |
| WO | 2010/094755 | 8/2010 |
| WO | 2010/128102 | 11/2010 |

OTHER PUBLICATIONS

Yoshida, K.I., et al., Jap. Circ. J. 1995, 59(1), pp. 40-48.
Li, X., et al., Mol. Biochem. Parasitol. 2007, 155(1), pp. 26-32.
Peltier, J., et al., J A, Soc Nephrol. 2006, 17, pp. 3415-3423.
Groshong, J.S., et al., J. Clin. Invest. 2007, 117(10), pp. 2903-2912.
Takano, et al., J Biol Chem. 2005, 280(16), pp. 16175-16184.
Spencer, M.J., et al., Hum Mol Gen, 2002, 11(21), pp. 2645-2655.
Patrick, G., et al., Nature 1999, 402, pp. 615-622.
Monaco, E.A., et al., Curr. Alzheimer Res. 2004, 1(1), pp. 33-38.
Higuchi, J., et al., J. Biol. Chem. 2005, 280(15), pp. 15229-15237.
Mokhtarian, F., et al., J. Neuroimmunology 2006, vol. 180, pp. 135-146.
Park, et al. J. Meurosci. 2005, 25, pp. 5365-5375.
Higaki, J., et al., Neuron, 1995, 14, pp. 651-659.
Watanabe, N., et al., Cytokine 1994, 6(6), pp. 597-601.
Shiba, E., et al. 20th Meeting Int. Association Breast Cancer Res., Sendai Jp, Sep. 25-28, 1994, Int. J. Oncol. S (Suppl.), 1994, p. 381.
O'Donnell, et al., J. Neurosci. 2006, 26(3), pp. 981-990.
Teranishi, et al., Biochem. Biophys. Res. Comm. 2003, 303(3), pp. 940-946.
Kunz, et al., Pain 2004, 110, pp. 409-418.
Wang, et al., Brain 2004, 127, pp. 671-679.
Cuzzocrea, et al., American Journal of Pathology 2000, 157(6), pp. 2065-2079.
Shi, Y., et al., Am. J. Physiol. Renal Physiol. 2000, 279, pp. 509-517.
Dnyanmote, et al., Toxicology and Applied Pharmacology 2006, 215, pp. 146-157.
Chatterjee, P. et al., Biochem. Pharmacol. 2005, 7, pp. 1121-1131.
Greenbaum, D., et al. Science 324, 794 (2009).
Jung, et al., Archives of Pharmacal Research (2009), 32(6), 899-906.
Pietsch, M., et al., current Topics in Medicinal Chemistry, 2010, 10, pp. 270-293.
Carragher, N.O., Curr. Pharm. Design 2006, 12, pp. 615-638.
Wang, K.K., et al. Drugs of the Future, 1998, 23(7), pp. 741-749; and Trends in Pharmacol. Sc. 1994, 15, pp. 412-419.
Fehrentz, J.A., et al., Synthesis 1983, pp. 676-678.
Rosemond, M.J.C, et al., "Human carbonyl reduction pathways and a strategy for their study in vitro", Drug Metabolism Reviews, 2004, 36, 335-361.
Hoffmann, F., et al., "Carbonyl reductases and pluripotent hydroxysteroid dehydrogenases of the shortchain dehydrogenases/ reductases superfamily." Drug Metabolism Reviews 2007, 39, 87-144.

\* cited by examiner

CARBOXAMIDE COMPOUNDS AND THEIR USE AS CALPAIN INHIBITORS V

CROSS-REFERENCE TO RELATED APPLICATIONS

This claims priority to U.S. Provisional Patent Application No. 61/410,414, filed on Nov. 5, 2010, and U.S. Provisional Patent Application No. 61/288,935, filed on Dec. 22, 2009.

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.

Calpains are intracellular, proteolytic enzymes from the cysteine protease group and are found in many cells. The enzyme calpain is activated by elevated calcium concentration, with a distinction being made between calpain I or µ-calpain, which is activated by µ-molar concentrations of calcium ions, and calpain II or m-calpain, which is activated by m-molar concentrations of calcium ions. Currently, further calpain isoenzymes are also postulated (M. E. Saez et al.; Drug Discovery Today 2006, 11 (19/20), pp. 917-923; K. Suzuki et al., Biol. Chem. Hoppe-Seyler, 1995, 376 (9), pp. 523-9).

Calpains play an important role in various physiological processes. These processes include the cleavage of different regulatory proteins such as protein kinase C, cytoskeletal proteins such as MAP 2 and spectrin, and muscle proteins, protein degradation in rheumatoid arthritis, proteins in the activation of platelets, neuropeptide metabolism, proteins in mitosis, and others which are listed in: M. J. Barrett et al., Life Sci. 1991, 48, pp. 1659-69; K. Wang et al., Trends in Pharmacol. Sci. 1994, 15, pp. 412-419.

Elevated calpain levels have been measured in various pathophysiological processes, for example: ischemias of the heart (e.g. myocardial infarction), the kidney, the lung, the liver or the central nervous system (e.g. stroke), inflammations, muscular dystrophies, cataracts of the eyes, diabetes, HIV disorders, injuries to the central nervous system (e.g. brain trauma), Alzheimer's, Huntington's, Parkinson's diseases, multiple sclerosis etc. (see K. K. Wang, above) and infectious diseases such as malaria (I M Medana et al., Neuropath and Appl. Neurobiol. 2007, 33, pp. 179-192). It is assumed that there is a connection between these diseases and generally or persistently elevated intracellular calcium levels. This results in calcium-dependent processes becoming hyperactivated and no longer being subject to normal physiological control. A corresponding hyperactivation of calpains can also trigger pathophysiological processes.

For this reason, it was postulated that inhibitors of calpain could be of use for treating these diseases. This postulate was confirmed by a variety of investigations. Thus, Seung-Chyul Hong et al., Stroke 1994, 25 (3), pp. 663-669, and R. T. Bartus et al., Neurological Res. 1995, 17, pp. 249-258, have demonstrated that calpain inhibitors have a neuroprotective effect in acute neurodegenerative impairments or ischemias such as occur after cerebral stroke. K. E. Saatman et al., Proc. Natl. Acad. Sci. USA, 1996, 93, pp. 3428-3433 describe that following experimental brain trauma, calpain inhibitors also improved recovery from the memory performance deficits and neuromotor impairments. C. L. Edelstein et al., Proc. Natl. Acad. Sci. USA, 1995, 92, pp. 7662-6, found that calpain inhibitors have a protective effect on hypoxia-damaged kidneys. Yoshida, Ken Ischi et al., Jap. Circ. J. 1995, 59 (1), pp. 40-48, pointed out that calpain inhibitors had favorable effects following cardiac damage which was produced by ischemia or reperfusion. The calpain inhibitor BDA-410 delayed the progression of malaria infection in a mouse model of malaria pathogenesis as shown by X. Li et al., Mol. Biochem. Parasitol. 2007, 155 (1), pp 26-32.

More recent studies have shown in calpastatin transgenic animals that the expression of the natural inhibitor of calpain significantly attenuates the pathophysiological effects of activated calpain in experimental glomerulonephritis shown by J. Peltier et al., J A, Soc Nephrol. 2006, 17, pp. 3415-3423, in cardiovascular remodeling in angiotensin II-induced hypertension, in impaired synaptic transmission in slow-channel congenital myasthenic syndrome shown by Groshong J S et al., J Clin Invest. 2007, 117 (10), pp 2903-2912, in excitotoxic DNA fragmentation via mitochondrial pathways shown by J Takano et al., J Biol Chem. 2005, 280 (16) pp. 16175-16184, and in necrotic processes in dystrophic muscles shown by M J Spencer et al., Hum Mol Gen, 2002, 11(21), pp 2645-2655.

It has been shown in recent years that both the function and the metabolism of a number of important proteins involved in the development of Alzheimer's disease are modulated by calpain. Various external influences such as, for example, excitotoxins, oxidative stress or else the action of amyloid protein lead to hyperactivation of calpain in the nerve cell, causing, as cascade, a dysregulation of the CNS-specific kinase cdk5 and subsequently a hyperphosphorylation of the so-called tau protein. Whereas the actual task of the tau protein consists of stabilizing the microtubules and thus the cytoskeleton, phosphorylated tau is no longer able to fulfill this function; the cytoskeleton collapses, axonal transport of matter is impaired and thus eventually the nerve cell degenerates (G. Patrick et al., Nature 1999, 402, pp. 615-622; E. A. Monaco et al.; Curr. Alzheimer Res. 2004, 1 (1), pp. 33-38). Accumulation of phosphorylated tau additionally leads to the formation of so-called neurofibrillary tangles (NFTs) which, together with the well-known amyloid plaques, represent a pathological hallmark of Alzheimer's disease. Similar changes in the tau protein, generally referred to important feature of as tauopathies are also observed in other (neuro) degenerative disorders such as, for example, following stroke, inflammations of the brain, Parkinsonism, in normal-pressure hydrocephalus and Creutzfeldt-Jakob disease.

The involvement of calpain in neurodegenerative processes has been demonstrated in transgenic mice with the aid of calpastatin, a specific and natural inhibitor of calpains (Higuchi et al.; J. Biol. Chem. 2005, 280 (15), pp. 15229-15237). It was possible with the aid of a calpain inhibitor to reduce markedly the clinical signs of acute autoimmune encephalomyelitis in a mouse model of multiple sclerosis (F. Mokhtarian et al.; J. Neuroimmunology 2006, Vol. 180, pp. 135-146). It has further been shown that calpain inhibitors on the one hand block the Ab-induced degeneration of neurons (Park et al.; J. Neurosci. 2005, 25, pp. 5365-5375), and in addition reduce the release of the β-amyloid precursor protein (β APP) (J. Higaki et al., Neuron, 1995, 14, pp. 651-659). With this background, calpain inhibitors having sufficient CNS availability represent a novel therapeutic principle for the treatment of neurodegenerative disorders in general and in particular also of Alzheimer's disease.

The release of interleukin-1α is likewise inhibited by calpain inhibitors (N. Watanabe et al., Cytokine 1994, 6(6), pp. 597-601). It has additionally been found that calpain inhibitors show cytotoxic effects on tumor cells (E. Shiba et al. 20th Meeting Int. Ass. Breast Cancer Res., Sendai Jp, 1994, 25.-28. Sep., Int. J. Oncol. S(Suppl.), 1994, 381).

The involvement of calpain in HIV disorders has only recently been shown. Thus, it has been demonstrated that the HIV-induced neurotoxicity is mediated by calpain (O'Donnell et al.; J. Neurosci. 2006, 26 (3), pp. 981-990). Calpain involvement in the replication of the HIV virus has also been shown (Teranishi et al.; Biochem. Biophys. Res. Comm 2003, 303 (3), pp. 940-946).

Recent investigations indicate that calpain plays a part in so-called nociception, the perception of pain. Calpain inhibitors showed a distinctly beneficial effect in various preclinically relevant models of pain, e.g. in the thermally induced hyperalgesia in rats (Kunz et al.; Pain 2004, 110, pp. 409-418), in Taxol-induced neuropathy (Wang et al.; Brain 2004, 127, pp. 671-679) and in acute and chronic inflammatory processes (Cuzzocrea et al.; American Journal of Pathology 2000, 157 (6), pp. 2065-2079).

The involvement of calpain in the development of kidney diseases, such as chronic kidney diseases, e.g. diabetic nephropathy, has also been shown recently. Thus, it has been demonstrated by Y. Shi et al. in animal models that the natural calpain inhibitor calpastatin is down regulated during renal ischemia reperfusion (Am. J. Physiol. Renal Physiol. 2000, 279, pp. 509-517). Furthermore, A. Dnyanmote et al., Toxicology and Applied Pharmacology 2006, 215, pp. 146-157, have shown that inhibition of calpain via overexpression of calpastatin reduces the progression of DCVC-induced renal injury in a model of acute renal failure. In addition, Peltier et al. have demonstrated that calpain activation and secretion promotes glomerular injury in experimental glomerulonephritis (J. Am. Soc. Nephrol. 2006, 17, pp. 3415-3423). It has also been shown that calpain inhibitors reduce renal dysfunction and injury caused by renal ischemia-reperfusion and thus may be useful in enhancing the tolerance of the kidney against renal injury associated with aortovascular surgery or renal transplantation (P. Chatterjee et al., Biochem. Pharmacol. 2005, 7, pp. 1121-1131).

Calpain has also been identified as a central mediator essential for parasitic activity. Parasites like *Plasmodium falciparum* and *Toxoplasma gondii* exploit host cell calpains to facilitate escape from the intracellular parasitophorous vacuole and/or host plasma membrane Inhibition of calpain-1 in hypotonically lysed and resealed erythrocytes prevented the escape of *P. falciparum* parasites, which was restored by adding purified calpain-1. Similarly, efficient egress of *T. gondii* from mammalian fibroblasts was blocked by either small interfering RNA-mediated suppression or genetic deletion of calpain activity and could be restored by genetic complementation (D. Greenbaum et al., Science 324, 794 (2009). Because parasites that fail to escape from their host cells are unable to proliferate, suggesting a strategy for anti-parasitic therapeutics. Pharmacological inhibition of calpain has been shown to exert anti-malarial activity, and hence presents a novel strategy for anti-parasitic strategy such as diseases caused by protest infections like malaria or toxoplasmosis (Li et al., *Mol Biochem Parasitol.* 2007; 155(1): 26-32; Jung et al. Archives of Pharmacal Research (2009), 32(6), 899-906, Chandramohanadas et al. Science (2009), 324, 794).

Further possible applications of calpain inhibitors are detailed in: M. Pietsch et al. Current Topics in Medicinal Chemistry, 2010, 10, 270-293; M. E. Saez et al.; Drug Discovery Today 2006, 11 (19/20), pp. 917-923; N. O. Carragher, Curr. Pharm. Design 2006, 12, pp. 615-638; K. K. Wang et al.; Drugs of the Future 1998, 23 (7), pp. 741-749; and Trends in Pharmacol. Sci. 1994, 15, pp. 412-419.

With the calpain inhibitors described to date a general distinction is made between irreversible and reversible inhibitors, and peptide and non-peptide inhibitors.

Irreversible inhibitors are usually alkylating substances. They have the disadvantage that they firstly react unselectively and/or are unstable in the body. Thus, corresponding inhibitors often show unwanted side effects such as toxicity, and application thereof is therefore markedly restricted. The irreversible inhibitors include for example epoxides such as E64, α-halo ketones, and disulfides.

A large number of known reversible calpain inhibitors are peptide aldehydes which are derived in particular from di- or tripeptides such as, for example, Z-Val-Phe-H (MDL 28170). Derivatives and prodrugs structurally derived from aldehydes are also described, especially corresponding acetals and hemiacetals (e.g. hydroxytetrahydrofurans, hydroxyoxazolindines, hydroxymorpholines and the like), but also imines or hydrazones. However, under physiological conditions, peptide aldehydes and related compounds usually have the disadvantage that, owing to their reactivity, they are frequently unstable, are rapidly metabolized and are prone to unspecific reactions which may likewise cause toxic effects (J. A. Fehrentz and B. Castro, Synthesis 1983, pp. 676-78).

In recent years, a number of non-peptide carboxamides having a β-keto function in the amine moiety and inhibiting calpain have been described. Thus, WO 98/16512 describes 3-amino-2-oxo carboxylic acid derivatives whose amino group is amidated with a 4-piperidinecarboxylic acid compound. WO 99/17775 describes similar compounds which are amidated with a quinolinecarboxylic acid. WO 98/25883, WO 98/25899 and WO 99/54294 describe 3-amino-2-oxo carboxylic acid derivatives whose amino group is amidated with a substituted benzoic acid. WO 99/61423 describes 3-amino-2-oxo carboxylic acid derivatives whose amino group is amidated with an aromatic carboxylic acid carrying a tetrahydroquinoline/isoquinoline and 2,3-dihydroindole/isoindole residue. Similar compounds in which the aromatic carboxylic acid residue carries a heterocyloalkyl radical or (hetero)aryl radical which is optionally connected via a linker are described in WO 99/54320, WO 99/54310, WO 99/54304 and WO 99/54305. Likewise, WO 08/080969 describes nicotinamides of 3-amino-2-oxo carboxylic acid derivatives that in position 2 of the pyridine ring are linked to a substituted pyrazole via a nitrogen atom. WO 03/080182 describes the use of the aforementioned amides for the treatment of pulmonary diseases. The nonpeptide calpain inhibitors mentioned therein also have a number of disadvantages, in particular a low or absent selectivity in respect of related cysteine proteases, such as various cathepsins, likewise possibly leading to unwanted side effects.

WO 07/016589 and WO 08/106130 describe 2-oxo carboxylic acid derivatives carrying a N-acylated 2-pyrrolidinecarboxylamido group in the 3-position. Also disclosed is their use for treating hepatitis C virus infections.

Carboxamides comprising an α-ketoamide moiety in the amine component, in particular those described in WO 08/080969, have been demonstrated to be highly effective and selective calpain inhibitors. However, as found out by the inventors of the present invention, in some cases they have limited cytosolic stability, namely in humans, possibly resulting in their premature clearance from the cytosol. As a consequence, the pharmacokinetics of these compounds may be insufficient.

The cytosolic degradation of said carboxamide compounds having an α-ketoamide moiety is believed to be mainly caused by metabolic reduction of the carbonyl function in the α-position. Carbonyl reduction is an important step in Phase I metabolism of carbonyl-containing drugs by converting aldehyde, ketone or quinone moieties to alcohols to facilitate the elimination by Phase II conjugation or direct excretion (M. J. C. Rosemond and J. S. Walsh: "Human carbonyl reduction pathways and a strategy for their study in vitro", Drug Metabolism Reviews, 2004, 36, 335-361). Human carbonyl-reducing activities are ubiquitous, found in many tissues including liver, lung, brain, heart, kidney, and blood. Multiple human carbonyl-reducing enzymes have been characterized, including medium-chain (MDR), and short-chain (SDR) dehydrogenases/reductases, aldo-keto reductases (AKR), and quinone reductases (QR), most of these are present in liver cytosols, except for some SDR family present in liver microsomes and mitochondria as described in F. Hoffmann and E. Maser: "Carbonyl reductases and pluripotent hydroxysteroid dehydrogenases of the shortchain dehydrogenases/reductases superfamily", Drug Metabolism Reviews 2007, 39, 87-144.

The present invention is thus based on the object of providing compounds which inhibit calpain with high affinity and selectivity. The compounds are further intended to display enhanced cytosolic stability in human cells, such as hepatocytes, and in consequence improved pharmacokinetics.

This object and further objects are achieved by the carboxamide compounds of the general formula I described below, the pharmaceutically suitable salts, the prodrugs, the hydrates and the tautomers thereof:

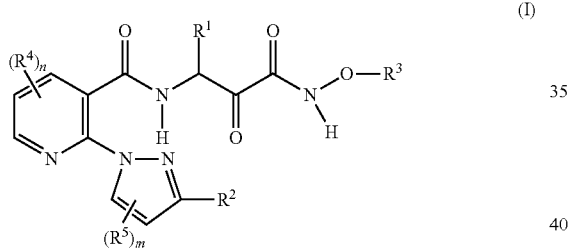

(I)

in which $R^1$ is $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$, aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where $R^{1a}$ is selected independently of one another from OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, COOR$^{a1}$, CONR$^{a2}$R$^{a3}$, SO$_2$NR$^{a2}$R$^{a3}$, —NR$^{a2}$—SO$_2$—R$^{a4}$, NR$^{a2}$—CO—R$^{a5}$, SO$_2$—R$^{a4}$ and NR$^{a6}$R$^{a7}$, $R^{1b}$ is selected independently of one another from OH, SH, COOH, CN, OCH$_2$COOH, halogen, phenyl which optionally has 1, 2 or 3 substituents $R^{1d}$, $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$, COOR$^{b1}$, CONR$^{b2}$R$^{b3}$, SO$_2$NR$^{b2}$R$^{b3}$, NR$^{b2}$—SO$_2$—R$^{b4}$, NR$^{b2}$—CO—R$^{b5}$, SO$_2$—R$^{b4}$ and NR$^{b6}$R$^{b7}$, in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring, $R^{1c}$ is selected independently of one another from OH, SH, halogen, NO$_2$, NH$_2$, CN, COOH, OCH$_2$COOH, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals, aryl, hetaryl, O-aryl, O—CH$_2$-aryl, where the last three radicals mentioned are unsubstituted in the aryl moiety or may carry 1, 2, 3 or 4 $R^{1d}$ radicals, COOR$^{c1}$, CONR$^{c2}$R$^{c3}$, SO$_2$NR$^{c2}$R$^{c3}$, NR$^{c2}$—SO$_2$—R$^{c4}$, NR$^{c2}$—CO—R$^{c5}$, SO$_2$—R$^{c4}$, —(CH$_2$)$_p$—NR$^{c6}$R$^{c7}$ with p=0, 1, 2, 3, 4, 5 or 6 and O—(CH$_2$)$_q$—NR$^{c6}$R$^{c7}$ with q=2, 3, 4, 5 or 6; where $R^{a1}$, $R^{b1}$ and $R^{c1}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, $R^{a2}$, $R^{b2}$ and $R^{c2}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and $R^{a3}$, $R^{b3}$ and $R^{c3}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a3}$, or $R^{b2}$ and $R^{b3}$ or $R^{c2}$ and $R^{c3}$ form together with the N atom a 3 to 7-membered, optionally substituted nitrogen heterocycle which may optionally have 1, 2 or 3 further different or identical heteroatoms from the group of O, N, S as ring members, $R^{a4}$, $R^{b4}$ and $R^{c4}$ are independently of one another $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-

C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, and R$^{a5}$, R$^{b5}$ and R$^{c5}$ have independently of one another one of the meanings mentioned for R$^{a1}$, R$^{b1}$ and R$^{c1}$;

R$^{a6}$, R$^{b6}$ and R$^{c6}$ are independently of one another H, C$_1$-C$_6$-alkyl, C$_1$-C$_6$-alkoxy, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, SO$_2$—C$_1$-C$_6$-alkyl, aryl, hetaryl, O-aryl, OCH$_2$-aryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$-(aryl-C$_1$-C$_4$-alkyl) or SO$_2$-(hetaryl-C$_1$-C$_4$-alkyl), where aryl and hetaryl in the last 18 radicals mentioned are unsubstituted or have 1, 2 or 3 substituents R$^{1d}$, and R$^{a7}$, R$^{b7}$ and R$^{c7}$ are independently of one another H, C$_1$-C$_6$-alkyl, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, or the two radicals R$^{a6}$ and R$^{a7}$, or R$^{b6}$ and R$^{b7}$ or R$^{c6}$ and R$^{c7}$ form together with the N atom a 3 to 7-membered, optionally substituted nitrogen heterocycle which may optionally have 1, 2 or 3 further different or identical heteroatoms from the group of O, N and S as ring members, or two radicals R$^{1b}$ or two radicals R$^{1c}$ bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N and S as ring members;

R$^{1d}$ is selected from halogen, OH, SH, NO$_2$, COOH, C(O)NH$_2$, CHO, CN, NH$_2$, OCH$_2$COOH, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, CO—C$_1$-C$_6$-alkyl, CO—O—C$_1$-C$_6$-alkyl, NH—C$_1$-C$_6$-alkyl, NHCHO, NH—C(O)C$_1$-C$_6$-alkyl, and SO$_2$—C$_1$-C$_6$-alkyl;

R$^2$ is C$_3$-C$_7$-cycloalkyl, C$_3$-C$_7$-cycloalkyl-C$_1$-C$_4$-alkyl, where a CH$_2$ group in the cycloalkyl moiety of the last two radicals mentioned may be replaced by O, NH, or S, or two adjacent C atoms may form a double bond, where the cycloalkyl moiety may additionally have 1, 2, 3 or 4 R$^{2b}$ radicals;

aryl, O-aryl, O—CH$_2$-aryl, hetaryl, aryl-C$_1$-C$_6$-alkyl, aryl-C$_2$-C$_6$-alkenyl, hetaryl-C$_1$-C$_4$-alkyl or hetaryl-C$_2$-C$_6$-alkenyl, where aryl and hetaryl in the last 8 radicals mentioned may be unsubstituted or carry 1, 2, 3 or 4 identical or different R$^{2c}$ radicals; where R$^{2b}$ has one of the meanings indicated for R$^{1b}$, and R$^{2c}$ has one of the meanings indicated for R$^{1c}$;

R$^3$ is C$_1$-C$_4$-haloalkyl or C$_1$-C$_6$-alkyl, C$_3$-C$_6$-alkenyl, C$_3$-C$_6$-alkynyl, C$_3$-C$_6$-cycloalkyl, C$_3$-C$_6$-cycloalkyl-C$_1$-C$_2$-alkyl, C$_3$-C$_6$-heterocycloalkyl-C$_1$-C$_2$-alkyl, C$_1$-C$_4$-alkoxy-C$_1$-C$_2$-alkyl, where alkyl, alkenyl, alkoxy, alkynyl, cycloalkyl, heterocycloalkyl in the last 7 radicals mentioned are unsubstituted or have 1, 2 or 3 substituents R$^{xa}$, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{xd}$, where R$^{xa}$ has one of the meanings indicated for R$^{1a}$, and R$^{xd}$ has one of the meanings indicated for R$^{1d}$;

R$^4$ and R$^5$ are selected independently of one another from halogen, NH$_2$, CN, CF$_3$, CHF$_2$, CH$_2$F, O—CF$_3$, O—CHF$_2$, O—CH$_2$F, COOH, OCH$_2$COOH, C$_1$-C$_2$-alkyl, C$_1$-C$_2$-alkoxy, C$_1$-C$_2$-alkoxy-C$_1$-C$_2$-alkyl, C$_1$-C$_2$-alkylthio, CH$_2$NRR', where R and R' are selected independently of one another from hydrogen and C$_1$-C$_4$-alkyl;

m is 0, 1 or 2; and n is 0, 1 or 2.

The present invention therefore relates to the carboxamide compounds of the general formula I, their tautomers, the hydrates thereof, the pharmaceutically suitable salts of the carboxamide compounds I, the prodrugs of I and the pharmaceutically suitable salts of the prodrugs, tautomers or hydrates of I.

The carboxamide compounds of the invention of the formula I, their salts, their prodrugs, their hydrates and their tautomers effectively inhibit calpain even at low concentrations. They are additionally distinguished by a high selectivity in relation to the inhibition of the calpain compared with other cysteine proteases, such as cathepsin B, cathepsin K, cathepsin L and cathepsin S, and by their improved stability against cytosolic degradation.

The carboxamide compounds of the invention of the formula I, their salts, their prodrugs, their hydrates and their tautomers are therefore particularly suitable for treating disorders and conditions in creatures, especially human creatures, which are associated with an elevated calpain activity.

The invention therefore also relates to the use of carboxamide compounds of the formula I, their tautomers, their hydrates and their pharmaceutically suitable salts for the manufacture of a medicament, in particular of a medicament which is suitable for the treatment of a disorder or a condition which is associated with an elevated calpain activity.

The invention further relates to a medicament, in particular a medicament which is suitable for the treatment of a disorder or a condition which is associated with an elevated calpain activity. The medicament comprises at least one carboxamide compound of the formula I, as described herein, the tautomer, the hydrate or a prodrug of compound I, or a pharmaceutically suitable salt of compound I or of the tautomer, the hydrate or a prodrug of I.

The present invention also relates to carboxamide compounds, which are selected from the group consisting of 1-benzyl-N-(4-(ethoxyamino)-3,4-dioxo-1-phenylbutan-2-yl)-5-oxopyrrolidine-2-carboxamide, its stereoisomers (2R)-1-benzyl-N-(4-(ethoxyamino)-3,4-dioxo-1-phenylbutan-2-yl)-5-oxopyrrolidine-2-carboxamide and (2S)-1-benzyl-N-(4-(ethoxyamino)-3,4-dioxo-1-phenylbutan-2-yl)-5-oxopyrrolidine-2-carboxamide, as well as mixtures of these stereoisomers, 1-benzyl-N-(4-(isopropoxyamino)-3,4-dioxo-1-phenylbutan-2-yl)-5-oxopyrrolidine-2-carboxamide, its stereoisomers (2R)-1-benzyl-N-(4-(isopropoxyamino)-3,4-dioxo-1-phenylbutan-2-yl)-5-oxopyrrolidine-2-carboxamide and (2S)-1-benzyl-N-(4-(isopropoxyamino)-3,4-dioxo-1-phenylbutan-2-yl)-5-oxopyrrolidine-2-carboxamide, as well as mixtures of these stereoisomers, 1-benzyl-N-(4-(cyclopropylmethoxyamino)-3,4-dioxo-1-phenylbutan-2-yl)-5-oxopyrrolidine-2-carboxamide, its stereoisomers (2R)-1-benzyl-N-(4-(cyclopropylmethoxyamino)-3,4-dioxo-1-phenylbutan-2-yl)-5-oxopyrrolidine-2-carboxamide and (2S)-1-benzyl-N-(4-(cyclopropylmethoxyamino)-3,4-dioxo-1-phenylbutan-2-yl)-5-oxopyrrolidine-2-carboxamide, as well as mixtures of these stereoisomers, 1-(2-fluorobenzyl)-N-(4-(methoxyamino)-3,4-dioxo-1-phenylbutan-2-yl)-5-oxopyrrolidine-2-carboxamide, its stereoisomers (2R)-1-(2-fluorobenzyl)-N-(4-(methoxyamino)-3,4-dioxo-1-phenylbutan-2-yl)-5-oxopyrrolidine-2-carboxamide and (2-S)-1-(2-fluorobenzyl)-N-(4-(methoxyamino)-3,4-dioxo-1-phenylbutan-2-yl)-5-oxopyrrolidine-2-carboxamide, as well as mixtures of these stereoisomers, 1-(2-chlorobenzyl)-N-(4-(methoxyamino)-3,4-dioxo-1-phenylbutan-2-yl)-5-oxopyrrolidine-2-carboxamide, its stereoisomers (2R)-1-(2-chlorobenzyl)-N-(4-(methoxyamino)-3,4-dioxo-1-phenylbutan-2-yl)-5-oxopyrrolidine-2-carboxamide and (2S)-1-(2-chlorobenzyl)-N-(4-(methoxyamino)-3,4-dioxo-1-phenylbutan-2-yl)-5-oxopyrrolidine-2-carboxamide, as well as mixtures of these stereoisomers, and the tautomers thereof, the hydrates thereof, the prodrugs thereof and the pharmaceutically suitable salts thereof.

Theses carboxamide compounds, their salts, their prodrugs, their hydrates and their tautomers like the compounds of formula I effectively inhibit calpain even at low concentrations. They are additionally distinguished by a high selectivity in relation to the inhibition of the calpain compared with other cysteine proteases, such as cathepsin B, cathepsin K, cathepsin L and cathepsin S, and by their improved stability against cytosolic degradation. Therefore, these carboxamide compounds are particularly suitable for treating disorders and conditions in creatures, especially human creatures, which are associated with an elevated calpain activity. The invention therefore also relates to the use of these carboxamide compounds, their tautomers, their hydrates and their pharmaceutically suitable salts for the manufacture of a medicament, in particular of a medicament which is suitable for the treatment of a disorder or a condition which is associated with an elevated calpain activity as described herein for the compounds of formula I. As regards the tautomers, the hydrates, the pharmaceutically suitable salts or the prodrugs reference is made to the compounds of formula I.

The carboxamide compounds of the formula I may be present in the form of the α-ketoamide, as shown in the formula I. Alternatively they may also be present in the form of a hydrate, i.e. the keto group in the α-position relative to the amide moiety in the amine component is transformed into two geminal hydroxy groups, as shown in the formula I-H below. $R^1$, $R^2$, $R^3$, $R^4$, $R^5$, m and n in formula I-H have the aforementioned meanings.

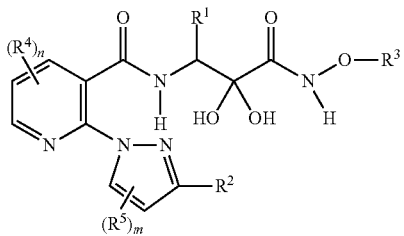

(I-H)

In the presence of water, especially under physiological conditions, usually both the α-ketoamide form and the hydrate form are present in a mixture.

Where only the α-ketoamide form is indicated in the following formulae and descriptions, it is intended to include also the hydrate and mixtures thereof with the α-ketoamide form unless indicated otherwise. Hydrates and α-ketoamide forms are equally suitable as calpain inhibitors.

The carboxamide compounds of the invention of the formula I are also able to form tautomers which are equally suitable as calpain inhibitors. Particular examples of tautomers to be mentioned are the compounds of the formula I-T:

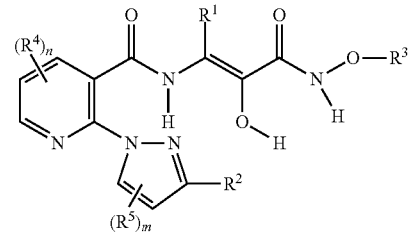

(I-T)

$R^1$, $R^2$, $R^3$, $R^4$, $R^5$, m and n in formula I-T have the aforementioned meanings.

The carboxamide compounds of the invention of the formula I can also form hemiacetals, hemiketals, acetals or ketals with alkanols. These compounds are equally suitable as calpain inhibitors as they are prodrugs of the compounds I. Accordingly, compounds where one or both of the geminal hydroxy groups shown in formula I-H are a radical derived from an alkanol, and especially $C_1$-$C_6$-alkoxy, can also be used according to the invention.

The term prodrug, as used herein and in the claims refers to a compound which is transformed under metabolic conditions into a compound of the formula I. Apart from the aforementioned hemiacetals, hemiketals, acetals and ketals prodrugs of the compounds I include the compounds of the formula I, wherein the oxygen atom of the keto group in α-position to the amide moiety is replaced with a group O-Alk-O, S-Alk-O or S-Alk-S, where Alk is linear $C_2$-$C_5$-alkandiyl, which may be unsubstituted or substituted with 1, 2, 3 or 4 radicals selected from $C_1$-$C_4$-alkyl or halogen, examples for such groups including $O(CH_2)_2O$, $O(CH_2)_5O$, $O(CH_2)_4O$, $S(CH_2)_2O$, $S(CH_2)_5O$, $S(CH_2)_4O$, etc. Further prodrugs or the compounds I include the compounds of the formula I, wherein the keto group in α-position to the amide moiety is replaced with a group C=$NR^6$, where $R^6$ is selected from H, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkyl-$C_1$-$C_4$-alkyl, $C_2$-$C_6$-alkenyloxy, $C_3$-$C_6$-cycloalkyloxy, $C_3$-$C_6$-cycloalkyl-$C_1$-$C_4$-alkyloxy. Under metabolic conditions, the aforementioned prodrugs are transformed into the corresponding α-ketoamide compounds of the formula I or into the corresponding hydrates of formula I-H. Therefore, said prodrugs and their pharmaceutically acceptable salts are also part of the invention.

It is equally possible to use pharmaceutically suitable salts of the carboxamide compounds of the formula I, of their tautomers, their hydrates or of their prodrugs, especially acid addition salts with physiologically tolerated organic or inorganic acids. Examples of suitable physiologically tolerated organic and inorganic acids are hydrochloric acid, hydrobromic acid, phosphoric acid, nitric acid, sulfuric acid, organic sulfonic acids having 1 to 12 carbon atoms, e.g. $C_1$-$C_4$-alkyl-sulfonic acids such as methanesulfonic acid, cycloaliphatic sulfonic acids such as S-(+)-10-camphorsulfonic acids, and aromatic sulfonic acids such as benzenesulfonic acid and toluenesulfonic acid, di- and tricarboxylic acids and hydroxy carboxylic acids having 2 to 10 carbon atoms, such as oxalic acid, malonic acid, maleic acid, fumaric acid, mucic acid, lactic acid, tartaric acid, citric acid, glycolic acid and adipic acid, as well as cis- and trans-cinnamic acid, furan-2-carboxylic acid and benzoic acid. Further suitable acids are described in Fortschritte der Arzneimittelforschung, Volume 10, pages 224 et seq., Birkhäuser Verlag, Basel and Stuttgart, 1966. The physiologically tolerated salts of the compounds of the formula I may be in the form of mono-, di-, tri- or tetras-alts, meaning that they may comprise 1, 2, 3 or 4 of the aforementioned acid molecules per molecule of the formula I. The acid molecules may be present in their acidic form or as anion.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

In the context of the present description, unless stated otherwise, the terms "alkyl", "alkoxy", "alkylthio", "haloalkyl", "haloalkoxy", "haloalkylthio", "alkenyl", "alkynyl", "alkylene" and radicals derived therefrom always include both unbranched and branched "alkyl", "alkoxy", "alkylthio", "haloalkyl", "haloalkoxy", "haloalkylthio", "alkenyl", "alkynyl" and "alkylene", respectively.

The prefix $C_n$-$C_m$-indicates the respective number of carbons in the hydrocarbon unit. Unless indicated otherwise, halogenated substituents preferably have one to five identical or different halogen atoms, especially fluorine atoms or chlorine atoms. $C_0$-Alkylene or $(CH_2)_0$ or similar expressions in the context of the description designate, unless indicated otherwise, a single bond.

The term "halogen" designates in each case, fluorine, bromine, chlorine or iodine, specifically fluorine, chlorine or bromine.

Examples of other meanings are:

Alkyl, and the alkyl moieties for example in alkoxy, alkylthio, arylalkyl, hetarylalkyl, cycloalkylalkyl or alkoxyalkyl: saturated, straight-chain or branched hydrocarbon radicals having one or more C atoms, e.g. 1 to 4, 1 to 6 or 1 to 10 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment of the invention, alkyl stands for small alkyl groups such as $C_1$-$C_4$-alkyl. In another embodiment of the invention, alkyl stands for larger alkyl groups such as $C_5$-$C_{10}$-alkyl.

Haloalkyl: an alkyl radical having ordinarily 1 to 6 or 1 to 4 C atoms as mentioned above, whose hydrogen atoms are partly or completely replaced by halogen atoms such as fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl, and the cycloalkyl moieties for example in cycloalkoxy or cycloalkyl-$C_1$-$C_6$-alkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl.

Alkenyl, and alkenyl moieties for example in aryl-($C_2$-$C_6$)-alkenyl: monounsaturated, straight-chain or branched hydrocarbon radicals having two or more C atoms, e.g. 2 to 4, 2 to 6 or 2 to 10 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Alkynyl: straight-chain or branched hydrocarbon groups having two or more C atoms, e.g. 2 to 4, 2 to 6 or 2 to 10 carbon atoms and one or two triple bonds in any position but nonadjacent, e.g. $C_2$-$C_6$-alkynyl such as ethynyl, 1-propynyl, 2-propynyl, 1-butynyl, 2-butynyl, 3-butynyl, 1-methyl-2- propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy or alkoxy moieties for example in alkoxyalkyl:

Alkyl as defined above having preferably 1 to 6 or 1 to 4 C atoms, which is linked via an O atom: e.g. methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Haloalkoxy: alkoxy as described above, in which the hydrogen atoms of these groups are partly or completely replaced by halogen atoms, i.e. for example $C_1$-$C_6$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, specifically chloromethoxy, fluoromethoxy, difluoromethoxy, trifluoromethoxy, 2-fluoroethoxy, 2-chloroethoxy or 2,2,2-trifluoroethoxy.

Alkoxyalkyl: an alkyl radical ordinarily having 1 to 4 C atoms, in which one hydrogen atom is replaced by an alkoxy radical ordinarily having 1 to 6 or 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkylthio: alkyl as defined above preferably having 1 to 6 or 1 to 4 C atoms, which is linked via an S atom, e.g. methylthio, ethylthio, n-propylthio and the like.

Haloalkylthio: haloalkyl as defined above preferably having 1 to 6 or 1 to 4 C atoms, which is linked via an S atom, e.g. fluoromethylthio, difluoromethylthio, trifluoromethylthio, 2-fluoroethylthio, 2,2-difluoroethylthio, 2,2,2-trifluoroethylthio, pentafluoroethylthio, 2-fluoropropylthio, 3-fluoropropylthio, 2,2-difluoropropylthio, 2,3-difluoropropylthio, and heptafluoropropylthio.

Aryl: a mono-, bi- or tricyclic aromatic hydrocarbon radical such as phenyl or naphthyl, especially phenyl.

Heterocyclyl: a heterocyclic radical which may be saturated or partly unsaturated or aromatic and which ordinarily has 3, 4, 5, 6, 7 or 8 ring atoms, where ordinarily 1, 2, 3 or 4, in particular 1, 2 or 3, of the ring atoms are heteroatoms such as N, S or O, besides carbon atoms as ring members.

Examples of saturated heterocycles are in particular:

Heterocycloalkyl: i.e. a saturated heterocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3-4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:
piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heterocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6- dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:
1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heterocyclic radical which ordinarily has 1, 2, 3 or 4 nitrogen atoms or a heteroatom selected from oxygen and sulfur and, if appropriate, 1, 2 or 3 nitrogen atoms as ring members besides carbon atoms as ring members: for example C-bonded, 5-membered heteroaromatic radicals having 1, 2, 3 or 4 nitrogen atoms or a heteroatom selected from oxygen and sulfur and, if appropriate, having 1, 2 or 3 nitrogen atoms as ring members, such as:
2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered heteroaromatic radicals having 1, 2, 3 or 4 nitrogen atoms as ring members, such as:
pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:
pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles which have one of the aforementioned 5- or 6-membered heterocyclic rings and a further saturated, unsaturated or aromatic carbocycle fused thereto, for example a benzene, cyclohexane, cyclohexene or cyclohexadiene ring, or a further 5- or 6-membered heterocyclic ring fused thereto, where the latter may likewise be saturated, unsaturated or aromatic. These bicyclic heterocycles include for example quinolinyl, isoquinolinyl, indolyl, indolizynyl, isoindolyl, indazolyl, benzofuryl, benzothienyl, benzo[b]thiazolyl, benzoxazolyl, benzthiazolyl and benzimidazolyl. Examples of 5- to 6-membered non-aromatic heterocyclic radicals comprising a fused benzene ring include dihydroindolyl, dihydroindolizynyl, dihydroisoindolyl, dihydroquinolinyl, dihydroisoquinolinyl, chromenyl and chromanyl.

Arylalkyl: an aryl radical as defined above which is linked via an alkylene group, in particular via a methylene, 1,1-ethylene or 1,2-ethylene group, e.g. benzyl, 1-phenyl-ethyl and 2-phenylethyl(=phenethyl).

Arylalkenyl: an aryl radical as defined above, which is linked via an alkenylene group, in particular via a 1,1-ethenyl, 1,2-ethenyl or 1,3-propenyl group, e.g. 2-phenylethen-1-yl and 1-phenylethen-1-yl.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Heterocyclylalkyl and hetarylalkyl: a heterocyclyl or hetaryl radical as defined above which is linked via an alkylene group, in particular via a methylene, 1,1-ethylene or 1,2-ethylene group.

The expression "optionally substituted" means in the context of the present invention that the respective moiety is substituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In relation to their use as calpain inhibitors, the variables $R^1$, $R^2$, $R^3$, $R^4$, $R^5$, m and n preferably have the following meanings, where these represent, both considered on their own and in combination with at least one other or all, special configurations of the compounds of the formula I:

$R^1$ is $C_1$-$C_{10}$-alkyl, preferably $C_3$-$C_8$-alkyl, which may be partly or completely halogenated and/or have 1, 2 or 3 substituents $R^{1a}$, in particular unsubstituted $C_1$-$C_{10}$-alkyl, specifically unsubstituted $C_3$-$C_8$-alkyl, $C_3$-$C_7$-cycloalkyl-$C_1$-$C_4$-alkyl, specifically $C_3$-$C_7$-cycloalkylmethyl, 1-($C_3$-$C_7$-cycloalkyl)ethyl or 2-($C_3$-$C_7$-cycloalkyl)ethyl, where the cycloalkyl moiety may have 1, 2, 3 or 4 radicals $R^{1b}$, very specifically cyclohexylmethyl, phenyl-$C_1$-$C_4$-alkyl or hetaryl-$C_1$-$C_4$-alkyl, in particular benzyl, 1-phenylethyl, 2-phenylethyl, hetarylmethyl, 1-hetarylethyl, 2-hetarylethyl such as thienylmethyl, pyridinylmethyl, where phenyl and hetaryl in the last radicals mentioned may be unsubstituted or carry 1, 2, 3 or 4 identical or different radicals $R^{1c}$.

More preferably $R^1$ is phenyl-$C_1$-$C_2$-alkyl or hetaryl-$C_1$-$C_2$-alkyl, where phenyl and hetaryl may be unsubstituted or carry 1 or 2 identical or different radicals $R^{1c}$ as defined herein, where $R^{1c}$ is in particular selected from halogen, specifically fluorine and chlorine, $C_1$-$C_2$-alkyl and $C_1$-$C_4$-alkoxy. In particular, $R^1$ is benzyl, where the phenyl group of benzyl may be unsubstituted or carry 1 or 2 identical or different radicals $R^{1c}$ as defined herein, where $R^{1c}$ is in particular selected from fluorine, chlorine, methyl and methoxy.

In this connection, $R^{1a}$, $R^{1b}$ and $R^{1c}$ where present have the aforementioned meanings. In particular:

$R^{1a}$ is $C_1$-$C_4$-alkoxy or $C_1$-$C_4$-haloalkoxy;

$R^{1b}$ is halogen, $C_1$-$C_4$-alkyl, $C_1$-$C_4$-haloalkyl, $C_1$-$C_4$-alkoxy or $C_1$-$C_4$-haloalkoxy; and $R^{1c}$ is halogen, $C_1$-$C_4$-alkyl, OH, SH, CN, $C_1$-$C_4$-haloalkyl, $C_1$-$C_4$-haloalkoxy, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —$(CH_2)_p$—$NR^{c6}R^{c7}$ with p=0, 1, 2, 3, 4, 5 or 6, in particular 0, and —O—$(CH_2)_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded, are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{1c}$ is in particular selected from halogen, $C_1$-$C_4$-alkyl, $C_1$-$C_4$-alkoxy, $CF_3$, $CHF_2$, $CH_2F$, O—$CHF_2$, O—$CH_2F$ $OCF_3$ and —$(CH_2)_p$—$NR^{c6}R^{c7}$ with p=0, 1 or 2, where $R^{c6}$ is selected from the group consisting of H and $C_1$-$C_4$-alkyl and.

$R^{c7}$ is selected from the group consisting of H and $C_1$-$C_4$-alkyl or the two radicals $R^{c6}$ and $R^{c7}$ form together with the N atom a 5, 6 or 7-membered, saturated nitrogen heterocycle which may optionally have further different or identical heteroatom from the group of O, N and S as ring member and where the nitrogen heterocycle is unsubstituted or carries 1, 2 or 3 substituents selected from $C_1$-$C_4$-alkyl.

$R^{1c}$ is in particular halogen, $C_1$-$C_4$-alkyl, $CF_3$, $CHF_2$, $CH_2F$, $C_1$-$C_4$-alkoxy, O—$CF_3$, O—$CHF_2$ or O—$CH_2F$.

$R^2$ is $C_3$-$C_7$-cycloalkyl-$C_1$-$C_4$-alkyl, specifically $C_3$-$C_7$-cycloalkylmethyl, 1-($C_3$-$C_7$-cycloalkyl)ethyl or 2-($C_3$-$C_7$-cycloalkyl)ethyl, where the cycloalkyl moiety may have 1, 2, 3 or 4 radicals $R^{2b}$, aryl or hetaryl, where aryl and hetaryl in the last 2 radicals mentioned may be unsubstituted or carry 1, 2, 3 or 4 identical or different radicals $R^{2c}$, aryl-$C_1$-$C_6$-alkyl, aryl-$C_2$-$C_6$-alkenyl or hetaryl-$C_1$-$C_4$-alkyl, where aryl and hetaryl in the last 3 radicals mentioned may be unsubstituted or carry 1, 2, 3 or 4 identical or different radicals $R^{2c}$.

More preferably $R^2$ is aryl, hetaryl, aryl-$C_1$-$C_6$-alkyl, aryl-$C_2$-$C_6$-alkenyl or hetaryl-$C_1$-$C_4$-alkyl, in particular aryl or hetaryl, and specifically phenyl, thienyl or pyridyl, where aryl and hetaryl (or phenyl, thienyl and pyridyl) may be unsubstituted or carry 1, 2, 3 or 4, in particular 1 or 2, identical or different radicals $R^{2c}$.

In particular, $R^2$ is phenyl, which may be unsubstituted or carry 1 or 2 radicals $R^{2c}$ as defined herein, with particular preference given to compounds where $R^{2c}$ is selected from the group consisting of halogen, $C_1$-$C_4$-alkyl, $C_1$-$C_4$-alkoxy, $CF_3$, $OCF_3$ and —$(CH_2)_p$—$NR^{c6}R^{c7}$ with p=0, 1 or 2, where $R^{c6}$ is selected from the group consisting of H and $C_1$-$C_4$-alkyl and.

$R^{c7}$ is selected from the group consisting of H and $C_1$-$C_4$-alkyl or the two radicals $R^{c6}$ and $R^{c7}$ form together with the N atom a 5, 6 or 7-membered, saturated nitrogen heterocycle which may optionally have further different or identical heteroatom from the group of O, N and S as ring member and where the nitrogen heterocycle is unsubstituted or carries 1, 2 or 3 substituents selected from $C_1$-$C_4$-alkyl.

More preferably $R^2$ is phenyl, which may be unsubstituted or carry 1 or 2 identical or different radicals selected from halogen, $C_1$-$C_2$-alkyl, $C_1$-$C_2$-alkoxy and —$(CH_2)_p$—$NR^{c6}R^{c7}$ with p=0, 1 or 2, where $R^{c6}$ is selected from the group consisting of H and $C_1$-$C_4$-alkyl and.

$R^{c7}$ is selected from the group consisting of H and $C_1$-$C_4$-alkyl or the two radicals $R^{c6}$ and $R^{c7}$ form together with the N atom a 5, 6 or 7-membered, saturated nitrogen heterocycle which may optionally have further different or identical heteroatom from the group of O, N and S as ring member and where the nitrogen heterocycle is unsubstituted or carries 1, 2 or 3 substituents selected from $C_1$-$C_4$-alkyl.

In particular embodiment, $R^2$ is phenyl, which may be unsubstituted or carry 1 radical selected from fluorine, chlorine, methyl and methoxy.

In this connection $R^{2b}$ and $R^{2c}$ where present have the aforementioned meanings. In particular:

$R^{2b}$ is halogen, $C_1$-$C_4$-alkyl, OH, CN, $CF_3$, O—$CF_3$, COOH, O—$CH_2$—COOH, $C_1$-$C_6$-alkoxy, $C_1$-$C_6$-alkylthio, COO—$C_1$-$C_6$-alkyl, $CONH_2$, CONH—$C_1$-$C_6$-alkyl, $SO_2NH$—$C_1$-$C_6$-alkyl, CONH-phenyl, $SO_2NH$-phenyl, CONH-hetaryl, $SO_2NH$-hetaryl, CON—$(C_1$-$C_6$-alkyl$)_2$, $SO_2N$—$(C_1$-$C_6$-alkyl$)_2$, NH—$SO_2$—$C_1$-$C_6$-alkyl, NH—CO—$C_1$-$C_6$-alkyl, $SO_2$—$C_1$-$C_6$-alkyl, $SO_2$-phenyl, NH—$SO_2$-phenyl, NH—CO-phenyl, NH—$SO_2$-hetaryl, NH—CO-hetaryl or $NR^{b6}R^{b7}$, where $R^{b6}$, $R^{b7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy; and $R^{2c}$ is halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —$(CH_2)_p$—$NR^{c6}R^{c7}$ with p=0, 1, 2, 3, 4, 5 or 6, in particular 0, and —O—$(CH_2)_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy, $R^{2c}$ is in particular selected from halogen, $C_1$-$C_4$-alkyl, $C_1$-$C_4$-alkoxy, $CF_3$, $OCF_3$ and —$(CH_2)_p$—$NR^{c6}R^{c7}$ with p=0, 1 or 2, where $R^{c6}$ is selected from the group consisting of H and $C_1$-$C_4$-alkyl and.

$R^{c7}$ is selected from the group consisting of H and $C_1$-$C_4$-alkyl or the two radicals $R^{c6}$ and $R^{c7}$ form together with the N atom a 5, 6 or 7-membered, saturated nitrogen heterocycle which may optionally have further different or identical heteroatom from the group of O, N and S as ring member and where the nitrogen heterocycle is unsubstituted or carries 1, 2 or 3 substituents selected from $C_1$-$C_4$-alkyl;

$R^3$ is selected from the group consisting of $C_1$-$C_6$-alkyl, $C_1$-$C_3$-haloalkyl, $C_3$-$C_5$-alkenyl, $C_3$-$C_5$-alkynyl, $C_3$-$C_6$-cycloalkyl, $C_3$-$C_6$-cycloalkyl-$C_1$-$C_2$-alkyl, $C_3$-$C_6$-heterocycloalkyl-$C_1$-$C_2$-alkyl, $C_1$-$C_2$-alkoxy-$C_1$-$C_2$-alkyl, in particular, where alkyl, alkenyl, alkoxy, cycloalkyl, heterocycloalkyl in the last 6 radicals mentioned are unsubstituted or have 1, 2 or 3 substituents $R^{xa}$, aryl, aryl-$C_1$-$C_4$-alkyl, hetaryl and hetaryl-$C_1$-$C_4$-alkyl, where aryl and hetaryl in the last 4 radicals mentioned are unsubstituted or have 1, 2 or 3 substituents $R^{xd}$, where $R^{xa}$ and $R^{xd}$ have the aforementioned meanings and in particular:

$R^{xa}$ is CN, $C_1$-$C_2$-alkoxy or $C_1$-$C_2$-haloalkoxy; and $R^{xd}$ is CN, $NO_2$, halogen, $C_1$-$C_4$-alkyl, $C_1$-$C_4$-haloalkyl, $C_1$-$C_4$-alkoxy or $C_1$-$C_4$-haloalkoxy.

$R^3$ is in particular selected from the group consisting of $C_1$-$C_4$-alkyl, $C_1$-$C_3$-haloalkyl, $C_3$-$C_5$-alkenyl, $C_3$-$C_5$-alkynyl, $C_3$-$C_6$-cycloalkyl, $C_3$-$C_6$-cycloalkyl-$C_1$-$C_2$-alkyl, $C_3$-$C_6$-heterocycloalkyl-$C_1$-$C_2$-alkyl and $C_1$-$C_2$-alkoxy-$C_1$-$C_2$-alkyl.

More preferably $R^3$ is $C_1$-$C_3$-alkyl, specifically methyl, ethyl, n-propyl or isopropyl, $C_1$-$C_3$-haloalkyl, $C_2$-$C_4$-alkenyl, specifically prop-2-en-1-yl(=allyl), but-2-enyl or but-3-enyl, $C_3$-$C_6$-cycloalkyl, specifically cyclopropyl or cyclobutyl or cyclopentyl, $C_3$-$C_6$-cycloalkyl-$C_1$-$C_2$-alkyl, specifically cyclopropylmethyl, $C_3$-$C_6$-heterocycloalkyl-$C_1$-$C_2$-alkyl, specifically 2-(4-morpholinyl)ethyl or phenyl-$C_1$-$C_3$-alkyl, specifically benzyl or 2-phenyl-ethyl.

$R^4$ and $R^5$ are independently of one another halogen, $CF_3$, $CHF_2$, $CH_2F$, $C_1$-$C_2$-alkyl or $C_1$-$C_2$-alkoxy.

More preferably $R^4$ and $R^5$ are independently of one another fluorine, chlorine, methyl, ethyl, or methoxy, and specifically fluorine, chlorine or methyl.

m and n are independently of one another 0 or 1 and specifically 0.

Otherwise, the radicals $R^{1d}$, $R^{a1}$, $R^{b1}$, $R^{c1}$, $R^{a2}$, $R^{b2}$, $R^{c2}$, $R^{a3}$, $R^{b3}$, $R^{c3}$, $R^{a4}$, $R^{b4}$, $R^{c4}$, $R^{a5}$, $R^{b5}$, $R^{c5}$, $R^{a6}$, $R^{b6}$, $R^{c6}$, $R^{a7}$, $R^{b7}$, $R^{c7}$, R and R' have, unless otherwise indicated, independently of one another preferably one of the following meanings:

$R^{1d}$: halogen, $C_1$-$C_4$-alkyl, $C_1$-$C_4$-haloalkyl, $C_1$-$C_4$-alkoxy and $C_1$-$C_4$-haloalkoxy.

$R^{a1}$, $R^{b1}$, $R^{c1}$ independently of one another: hydrogen, $C_1$-$C_6$-alkyl, $C_1$-$C_6$-haloalkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a2}$, $R^{b2}$, $R^{c2}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a3}$, $R^{b3}$, $R^{c3}$ independently of one another: hydrogen or $C_1$-$C_6$-alkyl, or $R^{a2}$ with $R^{a3}$ (and likewise $R^{b2}$ with $R^{b3}$ and $R^{c2}$ with $R^{c3}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{a4}$, $R^{b4}$, $R^{c4}$ independently of one another: $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a5}$, $R^{b5}$, $R^{c5}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a6}$, $R^{b6}$, $R^{c6}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a7}$, $R^{b7}$, $R^{c7}$ independently of one another: hydrogen or $C_1$-$C_6$-alkyl, or $R^{a6}$ with $R^{a7}$ (and likewise $R^{b6}$ with $R^{b7}$ and $R^{c6}$ with $R^{c7}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

R and R' independently of one another: hydrogen, methyl or ethyl.

According to a preferred embodiment of the invention the compounds of the formula I are predominately in the S-configuration at the carbon atom carrying the radical $R^1$, and according to a particular preferred embodiment the compounds I are completely S-configurated at said position.

According to one aspect of the invention the hydrogen atom linked to the carbon atom carrying the radical $R^1$ of a compound I is replaced by a deuterium atom, as shown in formula I-D below. $R^1$, $R^2$, $R^3$, $R^4$, $R^5$, m and n in formula I-H have the aforementioned meanings.

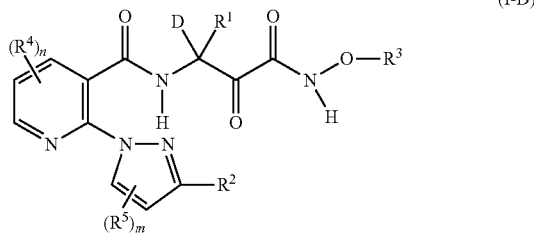

(I-D)

The degree of deuteration at said position usually exceeds 80%, preferably exceeds 90% and in particular exceeds 95%. The deuterated diasteromers of formula I-D often show a markedly higher stability against racematisation than their counterparts of formula I, probably due to a kinetic isotope effect (see F. Maltais et al. J. Med. Chem, DOI 10.1021/jm901023f). Thus, it is generally possible to stabilize the S-configuration at the carbon atom carrying radical $R^1$ of compounds I according to the aforementioned preferred embodiments of the invention, by introducing a deuterium at that carbon atom.

The compounds of the general formulae I and I-H which are indicated in Tables 1 to 35 below, and their tautomers, prodrugs and pharmaceutically acceptable salts, represent per se preferred embodiments of the present invention. The meanings for $R^2$, $R^3$, m and $R^5$ indicated in Table A below represent embodiments of the invention which are likewise preferred independently of one another and especially in combination.

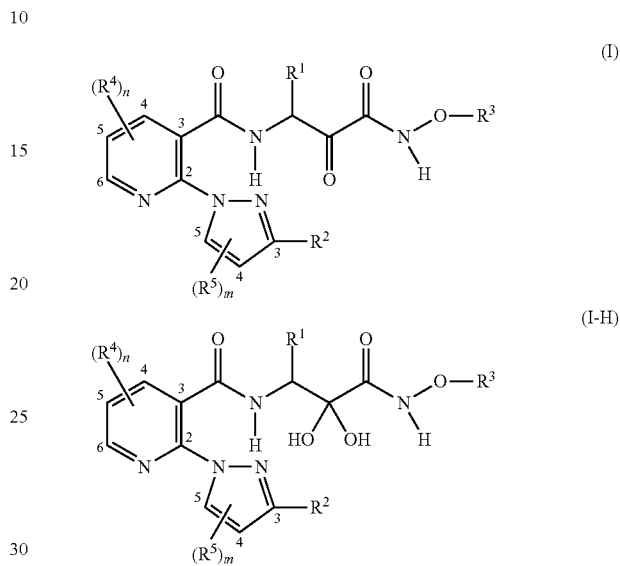

Table 1

Compounds of the formulae I and I-H in which $R^1$ is benzyl, n=0, i.e. $(R^4)_n$ is absent, and the combination of $R^2$, $R^3$, m and $R^5$ for a compound in each case corresponds to one line of Table A.

Table 2

Compounds of the formulae I and I-H in which $R^1$ is 3-fluoro-benzyl, n=0, i.e. $(R^4)_n$ is absent, and the combination of $R^2$, $R^3$, m and $R^5$ for a compound in each case corresponds to one line of Table A.

Table 3

Compounds of the formulae I and I-H in which $R^1$ is 4-fluoro-benzyl, n=0, i.e. $(R^4)_n$ is absent, and the combination of $R^2$, $R^3$, m and $R^5$ for a compound in each case corresponds to one line of Table A.

Table 4

Compounds of the formulae I and I-H in which $R^1$ is 3-chloro-benzyl, n=0, i.e. $(R^4)_n$ is absent, and the combination of $R^2$, $R^3$, m and $R^5$ for a compound in each case corresponds to one line of Table A.

Table 5

Compounds of the formulae I and I-H in which $R^1$ is 4-chloro-benzyl, n=0, i.e. $(R^4)_n$ is absent, and the combination of $R^2$, $R^3$, m and $R^5$ for a compound in each case corresponds to one line of Table A.

Table 6

Compounds of the formulae I and I-H in which $R^1$ is 4-methoxy-benzyl, n=0, i.e. $(R^4)_n$ is absent, and the combination of $R^2$, $R^3$, m and $R^5$ for a compound in each case corresponds to one line of Table A.

Table 7

Compounds of the formulae I and I-H in which $R^1$ is benzyl, $(R^4)_n$ is 4-F, and the combination of $R^2$, $R^3$, m and $R^5$ for a compound in each case corresponds to one line of Table A.

Table 8
Compounds of the formulae I and I-H in which $R^1$ is 3-fluoro-benzyl, $(R^4)_n$ is 4-F, and the combination of $R^2$, $R^3$, m and $R^5$ for a compound in each case corresponds to one line of Table A.

Table 9
Compounds of the formulae I and I-H in which $R^1$ is 4-fluoro-benzyl, $(R^4)_n$ is 4-F, and the combination of $R^2$, $R^3$, m and $R^5$ for a compound in each case corresponds to one line of Table A.

Table 10
Compounds of the formulae I and I-H in which $R^1$ is 3-chloro-benzyl, $(R^4)_n$ is 4-F, and the combination of $R^2$, $R^3$, m and $R^5$ for a compound in each case corresponds to one line of Table A.

Table 11
Compounds of the formulae I and I-H in which $R^1$ is 4-chloro-benzyl, $(R^4)_n$ is 4-F, and the combination of $R^2$, $R^3$, m and $R^5$ for a compound in each case corresponds to one line of Table A.

Table 12
Compounds of the formulae I and I-H in which $R^1$ is 4-methoxy-benzyl, $(R^4)_n$ is 4-F, and the combination of $R^2$, $R^3$, m and $R^5$ for a compound in each case corresponds to one line of Table A.

Table 13
Compounds of the formulae I and I-H in which $R^1$ is benzyl, $(R^4)_n$ is 5-F, and the combination of $R^2$, $R^3$, m and $R^5$ for a compound in each case corresponds to one line of Table A.

Table 14
Compounds of the formulae I and I-H in which $R^1$ is 3-fluoro-benzyl, $(R^4)_n$ is 5-F, and the combination of $R^2$, $R^3$, m and $R^5$ for a compound in each case corresponds to one line of Table A.

Table 15
Compounds of the formulae I and I-H in which $R^1$ is 4-fluoro-benzyl, $(R^4)_n$ is 5-F, and the combination of $R^2$, $R^3$, m and $R^5$ for a compound in each case corresponds to one line of Table A.

Table 16
Compounds of the formulae I and I-H in which $R^1$ is 3-chloro-benzyl, $(R^4)_n$ is 5-F, and the combination of $R^2$, $R^3$, m and $R^5$ for a compound in each case corresponds to one line of Table A.

Table 17
Compounds of the formulae I and I-H in which $R^1$ is 4-chloro-benzyl, $(R^4)_n$ is 5-F, and the combination of $R^2$, $R^3$, m and $R^5$ for a compound in each case corresponds to one line of Table A.

Table 18
Compounds of the formulae I and I-H in which $R^1$ is 4-methoxy-benzyl, $(R^4)_n$ is 5-F, and the combination of $R^2$, $R^3$, m and $R^5$ for a compound in each case corresponds to one line of Table A.

Table 19
Compounds of the formulae I and I-H in which $R^1$ is benzyl, $(R^4)_n$ is 6-F, and the combination of $R^2$, $R^3$, m and $R^5$ for a compound in each case corresponds to one line of Table A.

Table 20
Compounds of the formulae I and I-H in which $R^1$ is 3-fluoro-benzyl, $(R^4)_n$ is 6-F, and the combination of $R^2$, $R^3$, m and $R^5$ for a compound in each case corresponds to one line of Table A.

Table 21
Compounds of the formulae I and I-H in which $R^1$ is 4-fluoro-benzyl, $(R^4)_n$ is 6-F, and the combination of $R^2$, $R^3$, m and $R^5$ for a compound in each case corresponds to one line of Table A.

Table 22
Compounds of the formulae I and I-H in which $R^1$ is 3-chloro-benzyl, $(R^4)_n$ is 6-F, and the combination of $R^2$, $R^3$, m and $R^5$ for a compound in each case corresponds to one line of Table A.

Table 23
Compounds of the formulae I and I-H in which $R^1$ is 4-chloro-benzyl, $(R^4)_n$ is 6-F, and the combination of $R^2$, $R^3$, m and $R^5$ for a compound in each case corresponds to one line of Table A.

Table 24
Compounds of the formulae I and I-H in which $R^1$ is 4-methoxy-benzyl, $(R^4)_n$ is 6-F, and the combination of $R^2$, $R^3$, m and $R^5$ for a compound in each case corresponds to one line of Table A.

Table 25
Compounds of the formulae I and I-H in which $R^1$ is benzyl, $(R^4)_n$ is 4-Cl, and the combination of $R^2$, $R^3$, m and $R^5$ for a compound in each case corresponds to one line of Table A.

Table 26
Compounds of the formulae I and I-H in which $R^1$ is 3-fluoro-benzyl, $(R^4)_n$ is 4-Cl, and the combination of $R^2$, $R^3$, m and $R^5$ for a compound in each case corresponds to one line of Table A.

Table 27
Compounds of the formulae I and I-H in which $R^1$ is 4-fluoro-benzyl, $(R^4)_n$ is 4-Cl, and the combination of $R^2$, $R^3$, m and $R^5$ for a compound in each case corresponds to one line of Table A.

Table 28
Compounds of the formulae I and I-H in which $R^1$ is 3-chloro-benzyl, $(R^4)_n$ is 4-Cl, and the combination of $R^2$, $R^3$, m and $R^5$ for a compound in each case corresponds to one line of Table A.

Table 29
Compounds of the formulae I and I-H in which $R^1$ is 4-chloro-benzyl, $(R^4)_n$ is 4-Cl, and the combination of $R^2$, $R^3$, m and $R^5$ for a compound in each case corresponds to one line of Table A.

Table 30
Compounds of the formulae I and I-H in which $R^1$ is 4-methoxy-benzyl, $(R^4)_n$ is 4-Cl, and the combination of $R^2$, $R^3$, m and $R^5$ for a compound in each case corresponds to one line of Table A.

Table 31
Compounds of the formulae I and I-H in which $R^1$ is benzyl, $(R^4)_n$ is 5-Cl, and the combination of $R^2$, $R^3$, m and $R^5$ for a compound in each case corresponds to one line of Table A.

Table 32
Compounds of the formulae I and I-H in which $R^1$ is 3-fluoro-benzyl, $(R^4)_n$ is 5-Cl, and the combination of $R^2$, $R^3$, m and $R^5$ for a compound in each case corresponds to one line of Table A.

Table 33
Compounds of the formulae I and I-H in which $R^1$ is 4-fluoro-benzyl, $(R^4)_n$ is 5-Cl, and the combination of $R^2$, $R^3$, m and $R^5$ for a compound in each case corresponds to one line of Table A.

Table 34

Compounds of the formulae I and I-H in which $R^1$ is 3-chloro-benzyl, $(R^4)_n$ is 5-Cl, and the combination of $R^2$, $R^3$, m and $R^5$ for a compound in each case corresponds to one line of Table A.

Table 35

Compounds of the formulae I and I-H in which $R^1$ is 4-chloro-benzyl, $(R^4)_n$ is 5-Cl, and the combination of $R^2$, $R^3$, m and $R^5$ for a compound in each case corresponds to one line of Table A.

Table 36

Compounds of the formulae I and I-H in which $R^1$ is 4-methoxy-benzyl, $(R^4)_n$ is 5-Cl, and the combination of $R^2$, $R^3$, m and $R^5$ for a compound in each case corresponds to one line of Table A.

Table 37

Compounds of the formulae I and I-H in which $R^1$ is benzyl, $(R^4)_n$ is 6-Cl, and the combination of $R^2$, $R^3$, m and $R^5$ for a compound in each case corresponds to one line of Table A.

Table 38

Compounds of the formulae I and I-H in which $R^1$ is 3-fluoro-benzyl, $(R^4)_n$ is 6-Cl, and the combination of $R^2$, $R^3$, m and $R^5$ for a compound in each case corresponds to one line of Table A.

Table 39

Compounds of the formulae I and I-H in which $R^1$ is 4-fluoro-benzyl, $(R^4)_n$ is 6-Cl, and the combination of $R^2$, $R^3$, m and $R^5$ for a compound in each case corresponds to one line of Table A.

Table 40

Compounds of the formulae I and I-H in which $R^1$ is 3-chloro-benzyl, $(R^4)_n$ is 6-Cl, and the combination of $R^2$, $R^3$, m and $R^5$ for a compound in each case corresponds to one line of Table A.

Table 41

Compounds of the formulae I and I-H in which $R^1$ is 4-chloro-benzyl, $(R^4)_n$ is 6-Cl, and the combination of $R^2$, $R^3$, m and $R^5$ for a compound in each case corresponds to one line of Table A.

Table 42

Compounds of the formulae I and I-H in which $R^1$ is 4-methoxy-benzyl, $(R^4)_n$ is 6-Cl, and the combination of $R^2$, $R^3$, m and $R^5$ for a compound in each case corresponds to one line of Table A.

TABLE A

| No. | $R^2$ | $R^3$ | m | $R^5$ |
|---|---|---|---|---|
| A-1 | Phenyl | Methyl | 0 | — |
| A-2 | 2-Methylphenyl | Methyl | 0 | — |
| A-3 | 2-Methoxyphenyl | Methyl | 0 | — |
| A-4 | 2-Chlorophenyl | Methyl | 0 | — |
| A-5 | 2-Fluorophenyl | Methyl | 0 | — |
| A-6 | 3-Methylphenyl | Methyl | 0 | — |
| A-7 | 3-Methoxyphenyl | Methyl | 0 | — |
| A-8 | 3-Chlorophenyl | Methyl | 0 | — |
| A-9 | 3-Fluorophenyl | Methyl | 0 | — |
| A-10 | 4-Methylphenyl | Methyl | 0 | — |
| A-11 | 4-Methoxyphenyl | Methyl | 0 | — |
| A-12 | 4-Chlorophenyl | Methyl | 0 | — |
| A-13 | 4-Fluorophenyl | Methyl | 0 | — |
| A-14 | 2,4-Difluorophenyl | Methyl | 0 | — |
| A-15 | 2,6-Difluorophenyl | Methyl | 0 | — |
| A-16 | 3,5-Difluorophenyl | Methyl | 0 | — |
| A-17 | 2,4-Dichlorophenyl | Methyl | 0 | — |
| A-18 | 2,6-Dichlorophenyl | Methyl | 0 | — |
| A-19 | 3,5-Dichlorophenyl | Methyl | 0 | — |
| A-20 | 2-Chloro-4-fluorophenyl | Methyl | 0 | — |
| A-21 | Pyridin-2-yl | Methyl | 0 | — |
| A-22 | Pyridin-4-yl | Methyl | 0 | — |
| A-23 | Thien-2-yl | Methyl | 0 | — |
| A-24 | 3-Trifluoromethylphenyl | Methyl | 0 | — |
| A-25 | 4-(Diethylaminomethyl)phenyl | Methyl | 0 | — |
| A-26 | 4-(Morpholin-4-ylmethyl)phenyl | Methyl | 0 | — |
| A-27 | 4-(Morpholin-4-yl)phenyl | Methyl | 0 | — |
| A-28 | Phenyl | Ethyl | 0 | — |
| A-29 | 2-Methylphenyl | Ethyl | 0 | — |
| A-30 | 2-Methoxyphenyl | Ethyl | 0 | — |
| A-31 | 2-Chlorophenyl | Ethyl | 0 | — |
| A-32 | 2-Fluorophenyl | Ethyl | 0 | — |
| A-33 | 3-Methylphenyl | Ethyl | 0 | — |
| A-34 | 3-Methoxyphenyl | Ethyl | 0 | — |
| A-35 | 3-Chlorophenyl | Ethyl | 0 | — |
| A-36 | 3-Fluorophenyl | Ethyl | 0 | — |
| A-37 | 4-Methylphenyl | Ethyl | 0 | — |
| A-38 | 4-Methoxyphenyl | Ethyl | 0 | — |
| A-39 | 4-Chlorophenyl | Ethyl | 0 | — |
| A-40 | 4-Fluorophenyl | Ethyl | 0 | — |
| A-41 | 2,4-Difluorophenyl | Ethyl | 0 | — |
| A-42 | 2,6-Difluorophenyl | Ethyl | 0 | — |
| A-43 | 3,5-Difluorophenyl | Ethyl | 0 | — |
| A-44 | 2,4-Dichlorophenyl | Ethyl | 0 | — |
| A-45 | 2,6-Dichlorophenyl | Ethyl | 0 | — |
| A-46 | 3,5-Dichlorophenyl | Ethyl | 0 | — |
| A-47 | 2-Chloro-4-fluorophenyl | Ethyl | 0 | — |
| A-48 | Pyridin-2-yl | Ethyl | 0 | — |
| A-49 | Pyridin-4-yl | Ethyl | 0 | — |
| A-50 | Thien-2-yl | Ethyl | 0 | — |
| A-51 | 3-Trifluoromethylphenyl | Ethyl | 0 | — |
| A-52 | 4-(Diethylaminomethyl)phenyl | Ethyl | 0 | — |
| A-53 | 4-(Morpholin-4-ylmethyl)phenyl | Ehyl | 0 | — |
| A-54 | 4-(Morpholin-4-yl)phenyl | Ethyl | 0 | — |
| A-55 | Phenyl | Allyl | 0 | — |
| A-56 | 2-Methylphenyl | Allyl | 0 | — |
| A-57 | 2-Methoxyphenyl | Allyl | 0 | — |
| A-58 | 2-Chlorophenyl | Allyl | 0 | — |
| A-59 | 2-Fluorophenyl | Allyl | 0 | — |
| A-60 | 3-Methylphenyl | Allyl | 0 | — |
| A-61 | 3-Methoxyphenyl | Allyl | 0 | — |
| A-62 | 3-Chlorophenyl | Allyl | 0 | — |
| A-63 | 3-Fluorophenyl | Allyl | 0 | — |
| A-64 | 4-Methylphenyl | Allyl | 0 | — |
| A-65 | 4-Methoxyphenyl | Allyl | 0 | — |
| A-66 | 4-Chlorophenyl | Allyl | 0 | — |
| A-67 | 4-Fluorophenyl | Allyl | 0 | — |
| A-68 | 2,4-Difluorophenyl | Allyl | 0 | — |
| A-69 | 2,6-Difluorophenyl | Allyl | 0 | — |
| A-70 | 3,5-Difluorophenyl | Allyl | 0 | — |
| A-71 | 2,4-Dichlorophenyl | Allyl | 0 | — |
| A-72 | 2,6-Dichlorophenyl | Allyl | 0 | — |
| A-73 | 3,5-Dichlorophenyl | Allyl | 0 | — |
| A-74 | 2-Chloro-4-fluorophenyl | Allyl | 0 | — |
| A-75 | Pyridin-2-yl | Allyl | 0 | — |
| A-76 | Pyridin-4-yl | Allyl | 0 | — |
| A-77 | Thien-2-yl | Allyl | 0 | — |
| A-78 | 3-Trifluoromethylphenyl | Allyl | 0 | — |
| A-79 | 4-(Diethylaminomethyl)phenyl | Allyl | 0 | — |
| A-80 | 4-(Morpholin-4-ylmethyl)phenyl | Allyl | 0 | — |
| A-81 | 4-(Morpholin-4-yl)phenyl | Allyl | 0 | — |
| A-82 | Phenyl | Cyclopropyl | 0 | — |
| A-83 | 2-Methylphenyl | Cyclopropyl | 0 | — |
| A-84 | 2-Methoxyphenyl | Cyclopropyl | 0 | — |
| A-85 | 2-Chlorophenyl | Cyclopropyl | 0 | — |
| A-86 | 2-Fluorophenyl | Cyclopropyl | 0 | — |
| A-87 | 3-Methylphenyl | Cyclopropyl | 0 | — |
| A-88 | 3-Methoxyphenyl | Cyclopropyl | 0 | — |
| A-89 | 3-Chlorophenyl | Cyclopropyl | 0 | — |

TABLE A-continued

| No. | R² | R³ | m | R⁵ |
|---|---|---|---|---|
| A-90 | 3-Fluorophenyl | Cyclopropyl | 0 | — |
| A-91 | 4-Methylphenyl | Cyclopropyl | 0 | — |
| A-92 | 4-Methoxyphenyl | Cyclopropyl | 0 | — |
| A-93 | 4-Chlorophenyl | Cyclopropyl | 0 | — |
| A-94 | 4-Fluorophenyl | Cyclopropyl | 0 | — |
| A-95 | 2,4-Difluorophenyl | Cyclopropyl | 0 | — |
| A-96 | 2,6-Difluorophenyl | Cyclopropyl | 0 | — |
| A-97 | 3,5-Difluorophenyl | Cyclopropyl | 0 | — |
| A-98 | 2,4-Dichlorophenyl | Cyclopropyl | 0 | — |
| A-99 | 2,6-Dichlorophenyl | Cyclopropyl | 0 | — |
| A-100 | 3,5-Dichlorophenyl | Cyclopropyl | 0 | — |
| A-101 | 2-Chloro-4-fluorophenyl | Cyclopropyl | 0 | — |
| A-102 | Pyridin-2-yl | Cyclopropyl | 0 | — |
| A-103 | Pyridin-4-yl | Cyclopropyl | 0 | — |
| A-104 | Thien-2-yl | Cyclopropyl | 0 | — |
| A-105 | 3-Trifluoromethylphenyl | Cyclopropyl | 0 | — |
| A-106 | 4-(Diethylaminomethyl)phenyl | Cyclopropyl | 0 | — |
| A-107 | 4-(Morpholin-4-ylmethyl)phenyl | Cyclopropyl | 0 | — |
| A-108 | 4-(Morpholin-4-yl)phenyl | Cyclopropyl | 0 | — |
| A-109 | Phenyl | Propyl | 0 | — |
| A-110 | 2-Methylphenyl | Propyl | 0 | — |
| A-111 | 2-Methoxyphenyl | Propyl | 0 | — |
| A-112 | 2-Chlorophenyl | Propyl | 0 | — |
| A-113 | 2-Fluorophenyl | Propyl | 0 | — |
| A-114 | 3-Methylphenyl | Propyl | 0 | — |
| A-115 | 3-Methoxyphenyl | Propyl | 0 | — |
| A-116 | 3-Chlorophenyl | Propyl | 0 | — |
| A-117 | 3-Fluorophenyl | Propyl | 0 | — |
| A-118 | 4-Methylphenyl | Propyl | 0 | — |
| A-119 | 4-Methoxyphenyl | Propyl | 0 | — |
| A-120 | 4-Chlorophenyl | Propyl | 0 | — |
| A-121 | 4-Fluorophenyl | Propyl | 0 | — |
| A-122 | 2,4-Difluorophenyl | Propyl | 0 | — |
| A-123 | 2,6-Difluorophenyl | Propyl | 0 | — |
| A-124 | 3,5-Difluorophenyl | Propyl | 0 | — |
| A-125 | 2,4-Dichlorophenyl | Propyl | 0 | — |
| A-126 | 2,6-Dichlorophenyl | Propyl | 0 | — |
| A-127 | 3,5-Dichlorophenyl | Propyl | 0 | — |
| A-128 | 2-Chloro-4-fluorophenyl | Propyl | 0 | — |
| A-129 | Pyridin-2-yl | Propyl | 0 | — |
| A-130 | Pyridin-4-yl | Propyl | 0 | — |
| A-131 | Thien-2-yl | Propyl | 0 | — |
| A-132 | 3-Trifluoromethylphenyl | Propyl | 0 | — |
| A-133 | 4-(Diethylaminomethyl)phenyl | Propyl | 0 | — |
| A-134 | 4-(Morpholin-4-ylmethyl)phenyl | Propyl | 0 | — |
| A-135 | 4-(Morpholin-4-yl)phenyl | Propyl | 0 | — |
| A-136 | Phenyl | Isopropyl | 0 | — |
| A-137 | 2-Methylphenyl | Isopropyl | 0 | — |
| A-138 | 2-Methoxyphenyl | Isopropyl | 0 | — |
| A-139 | 2-Chlorophenyl | Isopropyl | 0 | — |
| A-140 | 2-Fluorophenyl | Isopropyl | 0 | — |
| A-141 | 3-Methylphenyl | Isopropyl | 0 | — |
| A-142 | 3-Methoxyphenyl | Isopropyl | 0 | — |
| A-143 | 3-Chlorophenyl | Isopropyl | 0 | — |
| A-144 | 3-Fluorophenyl | Isopropyl | 0 | — |
| A-145 | 4-Methylphenyl | Isopropyl | 0 | — |
| A-146 | 4-Methoxyphenyl | Isopropyl | 0 | — |
| A-147 | 4-Chlorophenyl | Isopropyl | 0 | — |
| A-148 | 4-Fluorophenyl | Isopropyl | 0 | — |
| A-149 | 2,4-Difluorophenyl | Isopropyl | 0 | — |
| A-150 | 2,6-Difluorophenyl | Isopropyl | 0 | — |
| A-151 | 3,5-Difluorophenyl | Isopropyl | 0 | — |
| A-152 | 2,4-Dichlorophenyl | Isopropyl | 0 | — |
| A-153 | 2,6-Dichlorophenyl | Isopropyl | 0 | — |
| A-154 | 3,5-Dichlorophenyl | Isopropyl | 0 | — |
| A-155 | 2-Chloro-4-fluorophenyl | Isopropyl | 0 | — |
| A-156 | Pyridin-2-yl | Isopropyl | 0 | — |
| A-157 | Pyridin-4-yl | Isopropyl | 0 | — |
| A-158 | Thien-2-yl | Isopropyl | 0 | — |
| A-159 | 3-Trifluoromethylphenyl | Isopropyl | 0 | — |
| A-160 | 4-(Diethylaminomethyl)phenyl | Isopropyl | 0 | — |
| A-161 | 4-(Morpholin-4-ylmethyl)phenyl | Isopropyl | 0 | — |
| A-162 | 4-(Morpholin-4-yl)phenyl | Isopropyl | 0 | — |
| A-163 | Phenyl | Tert.butyl | 0 | — |
| A-164 | 2-Methylphenyl | Tert.butyl | 0 | — |
| A-165 | 2-Methoxyphenyl | Tert.butyl | 0 | — |
| A-166 | 2-Chlorophenyl | Tert.butyl | 0 | — |
| A-167 | 2-Fluorophenyl | Tert.butyl | 0 | — |
| A-168 | 3-Methylphenyl | Tert.butyl | 0 | — |
| A-169 | 3-Methoxyphenyl | Tert.butyl | 0 | — |
| A-170 | 3-Chlorophenyl | Tert.butyl | 0 | — |
| A-171 | 3-Fluorophenyl | Tert.butyl | 0 | — |
| A-172 | 4-Methylphenyl | Tert.butyl | 0 | — |
| A-173 | 4-Methoxyphenyl | Tert.butyl | 0 | — |
| A-174 | 4-Chlorophenyl | Tert.butyl | 0 | — |
| A-175 | 4-Fluorophenyl | Tert.butyl | 0 | — |
| A-176 | 2,4-Difluorophenyl | Tert.butyl | 0 | — |
| A-177 | 2,6-Difluorophenyl | Tert.butyl | 0 | — |
| A-178 | 3,5-Difluorophenyl | Tert.butyl | 0 | — |
| A-179 | 2,4-Dichlorophenyl | Tert.butyl | 0 | — |
| A-180 | 2,6-Dichlorophenyl | Tert.butyl | 0 | — |
| A-181 | 3,5-Dichlorophenyl | Tert.butyl | 0 | — |
| A-182 | 2-Chloro-4-fluorophenyl | Tert.butyl | 0 | — |
| A-183 | Pyridin-2-yl | Tert.butyl | 0 | — |
| A-184 | Pyridin-4-yl | Tert.butyl | 0 | — |
| A-185 | Thien-2-yl | Tert.butyl | 0 | — |
| A-186 | 3-Trifluoromethylphenyl | Tert.butyl | 0 | — |
| A-187 | 4-(Diethylaminomethyl)phenyl | Tert.butyl | 0 | — |
| A-188 | 4-(Morpholin-4-ylmethyl)phenyl | Tert.butyl | 0 | — |
| A-189 | 4-(Morpholin-4-yl)phenyl | Tert.butyl | 0 | — |
| A-190 | Phenyl | Cyclobutyl | 0 | — |
| A-191 | 2-Methylphenyl | Cyclobutyl | 0 | — |
| A-192 | 2-Methoxyphenyl | Cyclobutyl | 0 | — |
| A-193 | 2-Chlorophenyl | Cyclobutyl | 0 | — |
| A-194 | 2-Fluorophenyl | Cyclobutyl | 0 | — |
| A-195 | 3-Methylphenyl | Cyclobutyl | 0 | — |
| A-196 | 3-Methoxyphenyl | Cyclobutyl | 0 | — |
| A-197 | 3-Chlorophenyl | Cyclobutyl | 0 | — |
| A-198 | 3-Fluorophenyl | Cyclobutyl | 0 | — |
| A-199 | 4-Methylphenyl | Cyclobutyl | 0 | — |
| A-200 | 4-Methoxyphenyl | Cyclobutyl | 0 | — |
| A-201 | 4-Chlorophenyl | Cyclobutyl | 0 | — |
| A-202 | 4-Fluorophenyl | Cyclobutyl | 0 | — |
| A-203 | 2,4-Difluorophenyl | Cyclobutyl | 0 | — |
| A-204 | 2,6-Difluorophenyl | Cyclobutyl | 0 | — |
| A-205 | 3,5-Difluorophenyl | Cyclobutyl | 0 | — |
| A-206 | 2,4-Dichlorophenyl | Cyclobutyl | 0 | — |
| A-207 | 2,6-Dichlorophenyl | Cyclobutyl | 0 | — |
| A-208 | 3,5-Dichlorophenyl | Cyclobutyl | 0 | — |
| A-209 | 2-Chloro-4-fluorophenyl | Cyclobutyl | 0 | — |
| A-210 | Pyridin-2-yl | Cyclobutyl | 0 | — |
| A-211 | Pyridin-4-yl | Cyclobutyl | 0 | — |
| A-212 | Thien-2-yl | Cyclobutyl | 0 | — |
| A-213 | 3-Trifluoromethylphenyl | Cyclobutyl | 0 | — |
| A-214 | 4-(Diethylaminomethyl)phenyl | Cyclobutyl | 0 | — |
| A-215 | 4-(Morpholin-4-ylmethyl)phenyl | Cyclobutyl | 0 | — |
| A-216 | 4-(Morpholin-4-yl)phenyl | Cyclobutyl | 0 | — |
| A-217 | Phenyl | Cyclopentyl | 0 | — |
| A-218 | 2-Methylphenyl | Cyclopentyl | 0 | — |
| A-219 | 2-Methoxyphenyl | Cyclopentyl | 0 | — |
| A-220 | 2-Chlorophenyl | Cyclopentyl | 0 | — |
| A-221 | 2-Fluorophenyl | Cyclopentyl | 0 | — |
| A-222 | 3-Methylphenyl | Cyclopentyl | 0 | — |
| A-223 | 3-Methoxyphenyl | Cyclopentyl | 0 | — |
| A-224 | 3-Chlorophenyl | Cyclopentyl | 0 | — |
| A-225 | 3-Fluorophenyl | Cyclopentyl | 0 | — |
| A-226 | 4-Methylphenyl | Cyclopentyl | 0 | — |
| A-227 | 4-Methoxyphenyl | Cyclopentyl | 0 | — |
| A-228 | 4-Chlorophenyl | Cyclopentyl | 0 | — |
| A-229 | 4-Fluorophenyl | Cyclopentyl | 0 | — |
| A-230 | 2,4-Difluorophenyl | Cyclopentyl | 0 | — |

TABLE A-continued

| No. | R² | R³ | m | R⁵ |
|---|---|---|---|---|
| A-231 | 2,6-Difluorophenyl | Cyclopentyl | 0 | — |
| A-232 | 3,5-Difluorophenyl | Cyclopentyl | 0 | — |
| A-233 | 2,4-Dichlorophenyl | Cyclopentyl | 0 | — |
| A-234 | 2,6-Dichlorophenyl | Cyclopentyl | 0 | — |
| A-235 | 3,5-Dichlorophenyl | Cyclopentyl | 0 | — |
| A-236 | 2-Chloro-4-fluorophenyl | Cyclopentyl | 0 | — |
| A-237 | Pyridin-2-yl | Cyclopentyl | 0 | — |
| A-238 | Pyridin-4-yl | Cyclopentyl | 0 | — |
| A-239 | Thien-2-yl | Cyclopentyl | 0 | — |
| A-240 | 3-Trifluoromethylphenyl | Cyclopentyl | 0 | — |
| A-241 | 4-(Diethylamino-methyl)phenyl | Cyclopentyl | 0 | — |
| A-242 | 4-(Morpholin-4-ylmethyl)phenyl | Cyclopentyl | 0 | — |
| A-243 | 4-(Morpholin-4-yl)phenyl | Cyclopentyl | 0 | — |
| A-244 | Phenyl | Cyclopropylmethyl | 0 | — |
| A-245 | 2-Methylphenyl | Cyclopropylmethyl | 0 | — |
| A-246 | 2-Methoxyphenyl | Cyclopropylmethyl | 0 | — |
| A-247 | 2-Chlorophenyl | Cyclopropylmethyl | 0 | — |
| A-248 | 2-Fluorophenyl | Cyclopropylmethyl | 0 | — |
| A-249 | 3-Methylphenyl | Cyclopropylmethyl | 0 | — |
| A-250 | 3-Methoxyphenyl | Cyclopropylmethyl | 0 | — |
| A-251 | 3-Chlorophenyl | Cyclopropylmethyl | 0 | — |
| A-252 | 3-Fluorophenyl | Cyclopropylmethyl | 0 | — |
| A-253 | 4-Methylphenyl | Cyclopropylmethyl | 0 | — |
| A-254 | 4-Methoxyphenyl | Cyclopropylmethyl | 0 | — |
| A-255 | 4-Chlorophenyl | Cyclopropylmethyl | 0 | — |
| A-256 | 4-Fluorophenyl | Cyclopropylmethyl | 0 | — |
| A-257 | 2,4-Difluorophenyl | Cyclopropylmethyl | 0 | — |
| A-258 | 2,6-Difluorophenyl | Cyclopropylmethyl | 0 | — |
| A-259 | 3,5-Difluorophenyl | Cyclopropylmethyl | 0 | — |
| A-260 | 2,4-Dichlorophenyl | Cyclopropylmethyl | 0 | — |
| A-261 | 2,6-Dichlorophenyl | Cyclopropylmethyl | 0 | — |
| A-262 | 3,5-Dichlorophenyl | Cyclopropylmethyl | 0 | — |
| A-263 | 2-Chloro-4-fluorophenyl | Cyclopropylmethyl | 0 | — |
| A-264 | Pyridin-2-yl | Cyclopropylmethyl | 0 | — |
| A-265 | Pyridin-4-yl | Cyclopropylmethyl | 0 | — |
| A-266 | Thien-2-yl | Cyclopropylmethyl | 0 | — |
| A-267 | 3-Trifluoromethylphenyl | Cyclopropylmethyl | 0 | — |
| A-268 | 4-(Diethylamino-methyl)phenyl | Cyclopropylmethyl | 0 | — |
| A-269 | 4-(Morpholin-4-ylmethyl)phenyl | Cyclopropylmethyl | 0 | — |
| A-270 | 4-(Morpholin-4-yl)phenyl | Cyclopropylmethyl | 0 | — |
| A-271 | Phenyl | 2-(Morpholin-4-yl)ethyl | 0 | — |
| A-272 | 2-Methylphenyl | 2-(Morpholin-4-yl)ethyl | 0 | — |
| A-273 | 2-Methoxyphenyl | 2-(Morpholin-4-yl)ethyl | 0 | — |
| A-274 | 2-Chlorophenyl | 2-(Morpholin-4-yl)ethyl | 0 | — |
| A-275 | 2-Fluorophenyl | 2-(Morpholin-4-yl)ethyl | 0 | — |
| A-276 | 3-Methylphenyl | 2-(Morpholin-4-yl)ethyl | 0 | — |
| A-277 | 3-Methoxyphenyl | 2-(Morpholin-4-yl)ethyl | 0 | — |
| A-278 | 3-Chlorophenyl | 2-(Morpholin-4-yl)ethyl | 0 | — |
| A-279 | 3-Fluorophenyl | 2-(Morpholin-4-yl)ethyl | 0 | — |
| A-280 | 4-Methylphenyl | 2-(Morpholin-4-yl)ethyl | 0 | — |
| A-281 | 4-Methoxyphenyl | 2-(Morpholin-4-yl)ethyl | 0 | — |
| A-282 | 4-Chlorophenyl | 2-(Morpholin-4-yl)ethyl | 0 | — |
| A-283 | 4-Fluorophenyl | 2-(Morpholin-4-yl)ethyl | 0 | — |
| A-284 | 2,4-Difluorophenyl | 2-(Morpholin-4-yl)ethyl | 0 | — |
| A-285 | 2,6-Difluorophenyl | 2-(Morpholin-4-yl)ethyl | 0 | — |
| A-286 | 3,5-Difluorophenyl | 2-(Morpholin-4-yl)ethyl | 0 | — |
| A-287 | 2,4-Dichlorophenyl | 2-(Morpholin-4-yl)ethyl | 0 | — |
| A-288 | 2,6-Dichlorophenyl | 2-(Morpholin-4-yl)ethyl | 0 | — |
| A-289 | 3,5-Dichlorophenyl | 2-(Morpholin-4-yl)ethyl | 0 | — |
| A-290 | 2-Chloro-4-fluorophenyl | 2-(Morpholin-4-yl)ethyl | 0 | — |
| A-291 | Pyridin-2-yl | 2-(Morpholin-4-yl)ethyl | 0 | — |
| A-292 | Pyridin-4-yl | 2-(Morpholin-4-yl)ethyl | 0 | — |
| A-293 | Thien-2-yl | 2-(Morpholin-4-yl)ethyl | 0 | — |
| A-294 | 3-Trifluoromethylphenyl | 2-(Morpholin-4-yl)ethyl | 0 | — |
| A-295 | 4-(Diethylamino-methyl)phenyl | 2-(Morpholin-4-yl)ethyl | 0 | — |
| A-296 | 4-(Morpholin-4-ylmethyl)phenyl | 2-(Morpholin-4-yl)ethyl | 0 | — |
| A-297 | 4-(Morpholin-4-yl)phenyl | 2-(Morpholin-4-yl)ethyl | 0 | — |
| A-298 | Phenyl | Benzyl | 0 | — |
| A-299 | 2-Methylphenyl | Benzyl | 0 | — |
| A-300 | 2-Methoxyphenyl | Benzyl | 0 | — |
| A-301 | 2-Chlorophenyl | Benzyl | 0 | — |
| A-302 | 2-Fluorophenyl | Benzyl | 0 | — |
| A-303 | 3-Methylphenyl | Benzyl | 0 | — |
| A-304 | 3-Methoxyphenyl | Benzyl | 0 | — |
| A-305 | 3-Chlorophenyl | Benzyl | 0 | — |
| A-306 | 3-Fluorophenyl | Benzyl | 0 | — |
| A-307 | 4-Methylphenyl | Benzyl | 0 | — |
| A-308 | 4-Methoxyphenyl | Benzyl | 0 | — |
| A-309 | 4-Chlorophenyl | Benzyl | 0 | — |
| A-310 | 4-Fluorophenyl | Benzyl | 0 | — |
| A-311 | 2,4-Difluorophenyl | Benzyl | 0 | — |
| A-312 | 2,6-Difluorophenyl | Benzyl | 0 | — |
| A-313 | 3,5-Difluorophenyl | Benzyl | 0 | — |
| A-314 | 2,4-Dichlorophenyl | Benzyl | 0 | — |
| A-315 | 2,6-Dichlorophenyl | Benzyl | 0 | — |
| A-316 | 3,5-Dichlorophenyl | Benzyl | 0 | — |
| A-317 | 2-Chloro-4-fluorophenyl | Benzyl | 0 | — |
| A-318 | Pyridin-2-yl | Benzyl | 0 | — |
| A-319 | Pyridin-4-yl | Benzyl | 0 | — |
| A-320 | Thien-2-yl | Benzyl | 0 | — |
| A-321 | 3-Trifluoromethylphenyl | Benzyl | 0 | — |
| A-322 | 4-(Diethylamino-methyl)phenyl | Benzyl | 0 | — |
| A-323 | 4-(Morpholin-4-ylmethyl)phenyl | Benzyl | 0 | — |
| A-324 | 4-(Morpholin-4-yl)phenyl | Benzyl | 0 | — |
| A-325 | Phenyl | Pyridin-2-yl-methyl | 0 | — |
| A-326 | 2-Methylphenyl | Pyridin-2-yl-methyl | 0 | — |
| A-327 | 2-Methoxyphenyl | Pyridin-2-yl-methyl | 0 | — |
| A-328 | 2-Chlorophenyl | Pyridin-2-yl-methyl | 0 | — |
| A-329 | 2-Fluorophenyl | Pyridin-2-yl-methyl | 0 | — |
| A-330 | 3-Methylphenyl | Pyridin-2-yl-methyl | 0 | — |
| A-331 | 3-Methoxyphenyl | Pyridin-2-yl-methyl | 0 | — |
| A-332 | 3-Chlorophenyl | Pyridin-2-yl-methyl | 0 | — |
| A-333 | 3-Fluorophenyl | Pyridin-2-yl-methyl | 0 | — |
| A-334 | 4-Methylphenyl | Pyridin-2-yl-methyl | 0 | — |
| A-335 | 4-Methoxyphenyl | Pyridin-2-yl-methyl | 0 | — |
| A-336 | 4-Chlorophenyl | Pyridin-2-yl-methyl | 0 | — |
| A-337 | 4-Fluorophenyl | Pyridin-2-yl-methyl | 0 | — |
| A-338 | 2,4-Difluorophenyl | Pyridin-2-yl-methyl | 0 | — |
| A-339 | 2,6-Difluorophenyl | Pyridin-2-yl-methyl | 0 | — |
| A-340 | 3,5-Difluorophenyl | Pyridin-2-yl-methyl | 0 | — |
| A-341 | 2,4-Dichlorophenyl | Pyridin-2-yl-methyl | 0 | — |
| A-342 | 2,6-Dichlorophenyl | Pyridin-2-yl-methyl | 0 | — |
| A-343 | 3,5-Dichlorophenyl | Pyridin-2-yl-methyl | 0 | — |
| A-344 | 2-Chloro-4-fluorophenyl | Pyridin-2-yl-methyl | 0 | — |
| A-345 | Pyridin-2-yl | Pyridin-2-yl-methyl | 0 | — |
| A-346 | Pyridin-4-yl | Pyridin-2-yl-methyl | 0 | — |
| A-347 | Thien-2-yl | Pyridin-2-yl-methyl | 0 | — |
| A-348 | 3-Trifluoromethylphenyl | Pyridin-2-yl-methyl | 0 | — |
| A-349 | 4-(Diethylamino-methyl)phenyl | Pyridin-2-yl-methyl | 0 | — |
| A-350 | 4-(Morpholin-4-ylmethyl)phenyl | Pyridin-2-yl-methyl | 0 | — |
| A-351 | 4-(Morpholin-4-yl)phenyl | Pyridin-2-yl-methyl | 0 | — |
| A-352 | Cyclopropyl | Methyl | 0 | — |
| A-353 | Cyclopropyl | Ethyl | 0 | — |
| A-354 | Cyclopropyl | Allyl | 0 | — |
| A-355 | Cyclopropyl | Cyclopropyl | 0 | — |
| A-356 | Cyclopropyl | Propyl | 0 | — |
| A-357 | Cyclopropyl | Isopropyl | 0 | — |
| A-358 | Cyclopropyl | Tert.-Butyl | 0 | — |
| A-359 | Cyclopropyl | Cyclobutyl | 0 | — |
| A-360 | Cyclopropyl | Cyclopentyl | 0 | — |
| A-361 | Cyclopropyl | Cyclopropylmethyl | 0 | — |
| A-362 | Cyclopropyl | 2-(Morpholin-4-yl)ethyl | 0 | — |
| A-363 | Cyclopropyl | Benzyl | 0 | — |
| A-364 | Cyclopropyl | Pyridin-2-yl-methyl | 0 | — |
| A-365 | Phenyl | Methyl | 1 | 4-F |
| A-366 | 2-Methylphenyl | Methyl | 1 | 4-F |
| A-367 | 2-Methoxyphenyl | Methyl | 1 | 4-F |
| A-368 | 2-Chlorophenyl | Methyl | 1 | 4-F |
| A-369 | 2-Fluorophenyl | Methyl | 1 | 4-F |
| A-370 | 3-Methylphenyl | Methyl | 1 | 4-F |
| A-371 | 3-Methoxyphenyl | Methyl | 1 | 4-F |

TABLE A-continued

| No. | R² | R³ | m | R⁵ |
|---|---|---|---|---|
| A-372 | 3-Chlorophenyl | Methyl | 1 | 4-F |
| A-373 | 3-Fluorophenyl | Methyl | 1 | 4-F |
| A-374 | 4-Methylphenyl | Methyl | 1 | 4-F |
| A-375 | 4-Methoxyphenyl | Methyl | 1 | 4-F |
| A-376 | 4-Chlorophenyl | Methyl | 1 | 4-F |
| A-377 | 4-Fluorophenyl | Methyl | 1 | 4-F |
| A-378 | 2,4-Difluorophenyl | Methyl | 1 | 4-F |
| A-379 | 2,6-Difluorophenyl | Methyl | 1 | 4-F |
| A-380 | 3,5-Difluorophenyl | Methyl | 1 | 4-F |
| A-381 | 2,4-Dichlorophenyl | Methyl | 1 | 4-F |
| A-382 | 2,6-Dichlorophenyl | Methyl | 1 | 4-F |
| A-383 | 3,5-Dichlorophenyl | Methyl | 1 | 4-F |
| A-384 | 2-Chloro-4-fluorophenyl | Methyl | 1 | 4-F |
| A-385 | Pyridin-2-yl | Methyl | 1 | 4-F |
| A-386 | Pyridin-4-yl | Methyl | 1 | 4-F |
| A-387 | Thien-2-yl | Methyl | 1 | 4-F |
| A-388 | 3-Trifluoromethylphenyl | Methyl | 1 | 4-F |
| A-389 | 4-(Diethylamino-methyl)phenyl | Methyl | | |
| A-390 | 4-(Morpholin-4-ylmethyl)phenyl | Methyl | 1 | 4-F |
| A-391 | 4-(Morpholin-4-yl)phenyl | Methyl | 1 | 4-F |
| A-392 | Phenyl | Ethyl | 1 | 4-F |
| A-393 | 2-Methylphenyl | Ethyl | 1 | 4-F |
| A-394 | 2-Methoxyphenyl | Ethyl | 1 | 4-F |
| A-395 | 2-Chlorophenyl | Ethyl | 1 | 4-F |
| A-396 | 2-Fluorophenyl | Ethyl | 1 | 4-F |
| A-397 | 3-Methylphenyl | Ethyl | 1 | 4-F |
| A-398 | 3-Methoxyphenyl | Ethyl | 1 | 4-F |
| A-399 | 3-Chlorophenyl | Ethyl | 1 | 4-F |
| A-400 | 3-Fluorophenyl | Ethyl | 1 | 4-F |
| A-401 | 4-Methylphenyl | Ethyl | 1 | 4-F |
| A-402 | 4-Methoxyphenyl | Ethyl | 1 | 4-F |
| A-403 | 4-Chlorophenyl | Ethyl | 1 | 4-F |
| A-404 | 4-Fluorophenyl | Ethyl | 1 | 4-F |
| A-405 | 2,4-Difluorophenyl | Ethyl | 1 | 4-F |
| A-406 | 2,6-Difluorophenyl | Ethyl | 1 | 4-F |
| A-407 | 3,5-Difluorophenyl | Ethyl | 1 | 4-F |
| A-408 | 2,4-Dichlorophenyl | Ethyl | 1 | 4-F |
| A-409 | 2,6-Dichlorophenyl | Ethyl | 1 | 4-F |
| A-410 | 3,5-Dichlorophenyl | Ethyl | 1 | 4-F |
| A-411 | 2-Chloro-4-fluorophenyl | Ethyl | 1 | 4-F |
| A-412 | Pyridin-2-yl | Ethyl | 1 | 4-F |
| A-413 | Pyridin-4-yl | Ethyl | 1 | 4-F |
| A-414 | Thien-2-yl | Ethyl | 1 | 4-F |
| A-415 | 3-Trifluoromethylphenyl | Ethyl | 1 | 4-F |
| A-416 | 4-(Diethylamino-methyl)phenyl | Ethyl | 1 | 4-F |
| A-417 | 4-(Morpholin-4-ylmethyl)phenyl | Ethyl | 1 | 4-F |
| A-418 | 4-(Morpholin-4-yl)phenyl | Ethyl | 1 | 4-F |
| A-419 | Phenyl | Allyl | 1 | 4-F |
| A-420 | 2-Methylphenyl | Allyl | 1 | 4-F |
| A-421 | 2-Methoxyphenyl | Allyl | 1 | 4-F |
| A-422 | 2-Chlorophenyl | Allyl | 1 | 4-F |
| A-423 | 2-Fluorophenyl | Allyl | 1 | 4-F |
| A-424 | 3-Methylphenyl | Allyl | 1 | 4-F |
| A-425 | 3-Methoxyphenyl | Allyl | 1 | 4-F |
| A-426 | 3-Chlorophenyl | Allyl | 1 | 4-F |
| A-427 | 3-Fluorophenyl | Allyl | 1 | 4-F |
| A-428 | 4-Methylphenyl | Allyl | 1 | 4-F |
| A-429 | 4-Methoxyphenyl | Allyl | 1 | 4-F |
| A-430 | 4-Chlorophenyl | Allyl | 1 | 4-F |
| A-431 | 4-Fluorophenyl | Allyl | 1 | 4-F |
| A-432 | 2,4-Difluorophenyl | Allyl | 1 | 4-F |
| A-433 | 2,6-Difluorophenyl | Allyl | 1 | 4-F |
| A-434 | 3,5-Difluorophenyl | Allyl | 1 | 4-F |
| A-435 | 2,4-Dichlorophenyl | Allyl | 1 | 4-F |
| A-436 | 2,6-Dichlorophenyl | Allyl | 1 | 4-F |
| A-437 | 3,5-Dichlorophenyl | Allyl | 1 | 4-F |
| A-438 | 2-Chloro-4-fluorophenyl | Allyl | 1 | 4-F |
| A-439 | Pyridin-2-yl | Allyl | 1 | 4-F |
| A-440 | Pyridin-4-yl | Allyl | 1 | 4-F |
| A-441 | Thien-2-yl | Allyl | 1 | 4-F |
| A-442 | 3-Trifluoromethylphenyl | Allyl | 1 | 4-F |
| A-443 | 4-(Diethylamino-methyl)phenyl | Allyl | 1 | 4-F |
| A-444 | 4-(Morpholin-4-ylmethyl)phenyl | Allyl | 1 | 4-F |
| A-445 | 4-(Morpholin-4-yl)phenyl | Allyl | 1 | 4-F |
| A-446 | Phenyl | Cyclopropyl | 1 | 4-F |
| A-447 | 2-Methylphenyl | Cyclopropyl | 1 | 4-F |
| A-448 | 2-Methoxyphenyl | Cyclopropyl | 1 | 4-F |
| A-449 | 2-Chlorophenyl | Cyclopropyl | 1 | 4-F |
| A-450 | 2-Fluorophenyl | Cyclopropyl | 1 | 4-F |
| A-451 | 3-Methylphenyl | Cyclopropyl | 1 | 4-F |
| A-452 | 3-Methoxyphenyl | Cyclopropyl | 1 | 4-F |
| A-453 | 3-Chlorophenyl | Cyclopropyl | 1 | 4-F |
| A-454 | 3-Fluorophenyl | Cyclopropyl | 1 | 4-F |
| A-455 | 4-Methylphenyl | Cyclopropyl | 1 | 4-F |
| A-456 | 4-Methoxyphenyl | Cyclopropyl | 1 | 4-F |
| A-457 | 4-Chlorophenyl | Cyclopropyl | 1 | 4-F |
| A-458 | 4-Fluorophenyl | Cyclopropyl | 1 | 4-F |
| A-459 | 2,4-Difluorophenyl | Cyclopropyl | 1 | 4-F |
| A-460 | 2,6-Difluorophenyl | Cyclopropyl | 1 | 4-F |
| A-461 | 3,5-Difluorophenyl | Cyclopropyl | 1 | 4-F |
| A-462 | 2,4-Dichlorophenyl | Cyclopropyl | 1 | 4-F |
| A-463 | 2,6-Dichlorophenyl | Cyclopropyl | 1 | 4-F |
| A-464 | 3,5-Dichlorophenyl | Cyclopropyl | 1 | 4-F |
| A-465 | 2-Chloro-4-fluorophenyl | Cyclopropyl | 1 | 4-F |
| A-466 | Pyridin-2-yl | Cyclopropyl | 1 | 4-F |
| A-467 | Pyridin-4-yl | Cyclopropyl | 1 | 4-F |
| A-468 | Thien-2-yl | Cyclopropyl | 1 | 4-F |
| A-469 | 3-Trifluoromethylphenyl | Cyclopropyl | 1 | 4-F |
| A-470 | 4-(Diethylamino-methyl)phenyl | Cyclopropyl | | |
| A-471 | 4-(Morpholin-4-ylmethyl)phenyl | Cyclopropyl | 1 | 4-F |
| A-472 | 4-(Morpholin-4-yl)phenyl | Cyclopropyl | 1 | 4-F |
| A-473 | Phenyl | Propyl | 1 | 4-F |
| A-474 | 2-Methylphenyl | Propyl | 1 | 4-F |
| A-475 | 2-Methoxyphenyl | Propyl | 1 | 4-F |
| A-476 | 2-Chlorophenyl | Propyl | 1 | 4-F |
| A-477 | 2-Fluorophenyl | Propyl | 1 | 4-F |
| A-478 | 3-Methylphenyl | Propyl | 1 | 4-F |
| A-479 | 3-Methoxyphenyl | Propyl | 1 | 4-F |
| A-480 | 3-Chlorophenyl | Propyl | 1 | 4-F |
| A-481 | 3-Fluorophenyl | Propyl | 1 | 4-F |
| A-482 | 4-Methylphenyl | Propyl | 1 | 4-F |
| A-483 | 4-Methoxyphenyl | Propyl | 1 | 4-F |
| A-484 | 4-Chlorophenyl | Propyl | 1 | 4-F |
| A-485 | 4-Fluorophenyl | Propyl | 1 | 4-F |
| A-486 | 2,4-Difluorophenyl | Propyl | 1 | 4-F |
| A-487 | 2,6-Difluorophenyl | Propyl | 1 | 4-F |
| A-488 | 3,5-Difluorophenyl | Propyl | 1 | 4-F |
| A-489 | 2,4-Dichlorophenyl | Propyl | 1 | 4-F |
| A-490 | 2,6-Dichlorophenyl | Propyl | 1 | 4-F |
| A-491 | 3,5-Dichlorophenyl | Propyl | 1 | 4-F |
| A-492 | 2-Chloro-4-fluorophenyl | Propyl | 1 | 4-F |
| A-493 | Pyridin-2-yl | Propyl | 1 | 4-F |
| A-494 | Pyridin-4-yl | Propyl | 1 | 4-F |
| A-495 | Thien-2-yl | Propyl | 1 | 4-F |
| A-496 | 3-Trifluoromethylphenyl | Propyl | 1 | 4-F |
| A-497 | 4-(Diethylamino-methyl)phenyl | Propyl | 1 | 4-F |
| A-498 | 4-(Morpholin-4-ylmethyl)phenyl | Propyl | 1 | 4-F |
| A-499 | 4-(Morpholin-4-yl)phenyl | Propyl | 1 | 4-F |
| A-500 | Phenyl | Isopropyl | 1 | 4-F |
| A-501 | 2-Methylphenyl | Isopropyl | 1 | 4-F |
| A-502 | 2-Methoxyphenyl | Isopropyl | 1 | 4-F |
| A-503 | 2-Chlorophenyl | Isopropyl | 1 | 4-F |
| A-504 | 2-Fluorophenyl | Isopropyl | 1 | 4-F |
| A-505 | 3-Methylphenyl | Isopropyl | 1 | 4-F |
| A-506 | 3-Methoxyphenyl | Isopropyl | 1 | 4-F |
| A-507 | 3-Chlorophenyl | Isopropyl | 1 | 4-F |
| A-508 | 3-Fluorophenyl | Isopropyl | 1 | 4-F |
| A-509 | 4-Methylphenyl | Isopropyl | 1 | 4-F |
| A-510 | 4-Methoxyphenyl | Isopropyl | 1 | 4-F |

TABLE A-continued

| No. | R² | R³ | m | R⁵ |
|---|---|---|---|---|
| A-511 | 4-Chlorophenyl | Isopropyl | 1 | 4-F |
| A-512 | 4-Fluorophenyl | Isopropyl | 1 | 4-F |
| A-513 | 2,4-Difluorophenyl | Isopropyl | 1 | 4-F |
| A-514 | 2,6-Difluorophenyl | Isopropyl | 1 | 4-F |
| A-515 | 3,5-Difluorophenyl | Isopropyl | 1 | 4-F |
| A-516 | 2,4-Dichlorophenyl | Isopropyl | 1 | 4-F |
| A-517 | 2,6-Dichlorophenyl | Isopropyl | 1 | 4-F |
| A-518 | 3,5-Dichlorophenyl | Isopropyl | 1 | 4-F |
| A-519 | 2-Chloro-4-fluorophenyl | Isopropyl | 1 | 4-F |
| A-520 | Pyridin-2-yl | Isopropyl | 1 | 4-F |
| A-521 | Pyridin-4-yl | Isopropyl | 1 | 4-F |
| A-522 | Thien-2-yl | Isopropyl | 1 | 4-F |
| A-523 | 3-Trifluoromethylphenyl | Isopropyl | 1 | 4-F |
| A-524 | 4-(Diethylamino-methyl)phenyl | Isopropyl | 1 | 4-F |
| A-525 | 4-(Morpholin-4-ylmethyl)phenyl | Isopropyl | 1 | 4-F |
| A-526 | 4-(Morpholin-4-yl)phenyl | Isopropyl | 1 | 4-F |
| A-527 | Phenyl | Tert.butyl | 1 | 4-F |
| A-528 | 2-Methylphenyl | Tert.butyl | 1 | 4-F |
| A-529 | 2-Methoxyphenyl | Tert.butyl | 1 | 4-F |
| A-530 | 2-Chlorophenyl | Tert.butyl | 1 | 4-F |
| A-531 | 2-Fluorophenyl | Tert.butyl | 1 | 4-F |
| A-532 | 3-Methylphenyl | Tert.butyl | 1 | 4-F |
| A-533 | 3-Methoxyphenyl | Tert.butyl | 1 | 4-F |
| A-534 | 3-Chlorophenyl | Tert.butyl | 1 | 4-F |
| A-535 | 3-Fluorophenyl | Tert.butyl | 1 | 4-F |
| A-536 | 4-Methylphenyl | Tert.butyl | 1 | 4-F |
| A-537 | 4-Methoxyphenyl | Tert.butyl | 1 | 4-F |
| A-538 | 4-Chlorophenyl | Tert.butyl | 1 | 4-F |
| A-539 | 4-Fluorophenyl | Tert.butyl | 1 | 4-F |
| A-540 | 2,4-Difluorophenyl | Tert.butyl | 1 | 4-F |
| A-541 | 2,6-Difluorophenyl | Tert.butyl | 1 | 4-F |
| A-542 | 3,5-Difluorophenyl | Tert.butyl | 1 | 4-F |
| A-543 | 2,4-Dichlorophenyl | Tert.butyl | 1 | 4-F |
| A-544 | 2,6-Dichlorophenyl | Tert.butyl | 1 | 4-F |
| A-545 | 3,5-Dichlorophenyl | Tert.butyl | 1 | 4-F |
| A-546 | 2-Chloro-4-fluorophenyl | Tert.butyl | 1 | 4-F |
| A-547 | Pyridin-2-yl | Tert.butyl | 1 | 4-F |
| A-548 | Pyridin-4-yl | Tert.butyl | 1 | 4-F |
| A-549 | Thien-2-yl | Tert.butyl | 1 | 4-F |
| A-550 | 3-Trifluoromethylphenyl | Tert.butyl | 1 | 4-F |
| A-551 | 4-(Diethylamino-methyl)phenyl | Tert.butyl | 1 | 4-F |
| A-552 | 4-(Morpholin-4-ylmethyl)phenyl | Tert.butyl | 1 | 4-F |
| A-553 | 4-(Morpholin-4-yl)phenyl | Tert.butyl | 1 | 4-F |
| A-554 | Phenyl | Cyclobutyl | 1 | 4-F |
| A-555 | 2-Methylphenyl | Cyclobutyl | 1 | 4-F |
| A-556 | 2-Methoxyphenyl | Cyclobutyl | 1 | 4-F |
| A-557 | 2-Chlorophenyl | Cyclobutyl | 1 | 4-F |
| A-558 | 2-Fluorophenyl | Cyclobutyl | 1 | 4-F |
| A-559 | 3-Methylphenyl | Cyclobutyl | 1 | 4-F |
| A-560 | 3-Methoxyphenyl | Cyclobutyl | 1 | 4-F |
| A-561 | 3-Chlorophenyl | Cyclobutyl | 1 | 4-F |
| A-562 | 3-Fluorophenyl | Cyclobutyl | 1 | 4-F |
| A-563 | 4-Methylphenyl | Cyclobutyl | 1 | 4-F |
| A-564 | 4-Methoxyphenyl | Cyclobutyl | 1 | 4-F |
| A-565 | 4-Chlorophenyl | Cyclobutyl | 1 | 4-F |
| A-566 | 4-Fluorophenyl | Cyclobutyl | 1 | 4-F |
| A-567 | 2,4-Difluorophenyl | Cyclobutyl | 1 | 4-F |
| A-568 | 2,6-Difluorophenyl | Cyclobutyl | 1 | 4-F |
| A-569 | 3,5-Difluorophenyl | Cyclobutyl | 1 | 4-F |
| A-570 | 2,4-Dichlorophenyl | Cyclobutyl | 1 | 4-F |
| A-571 | 2,6-Dichlorophenyl | Cyclobutyl | 1 | 4-F |
| A-572 | 3,5-Dichlorophenyl | Cyclobutyl | 1 | 4-F |
| A-573 | 2-Chloro-4-fluorophenyl | Cyclobutyl | 1 | 4-F |
| A-574 | Pyridin-2-yl | Cyclobutyl | 1 | 4-F |
| A-575 | Pyridin-4-yl | Cyclobutyl | 1 | 4-F |
| A-576 | Thien-2-yl | Cyclobutyl | 1 | 4-F |
| A-577 | 3-Trifluoromethylphenyl | Cyclobutyl | 1 | 4-F |
| A-578 | 4-(Diethylamino-methyl)phenyl | Cyclobutyl | 1 | 4-F |
| A-579 | 4-(Morpholin-4-ylmethyl)phenyl | Cyclobutyl | 1 | 4-F |
| A-580 | 4-(Morpholin-4-yl)phenyl | Cyclobutyl | 1 | 4-F |
| A-581 | Phenyl | Cyclopentyl | 1 | 4-F |
| A-582 | 2-Methylphenyl | Cyclopentyl | 1 | 4-F |
| A-583 | 2-Methoxyphenyl | Cyclopentyl | 1 | 4-F |
| A-584 | 2-Chlorophenyl | Cyclopentyl | 1 | 4-F |
| A-585 | 2-Fluorophenyl | Cyclopentyl | 1 | 4-F |
| A-586 | 3-Methylphenyl | Cyclopentyl | 1 | 4-F |
| A-587 | 3-Methoxyphenyl | Cyclopentyl | 1 | 4-F |
| A-588 | 3-Chlorophenyl | Cyclopentyl | 1 | 4-F |
| A-589 | 3-Fluorophenyl | Cyclopentyl | 1 | 4-F |
| A-590 | 4-Methylphenyl | Cyclopentyl | 1 | 4-F |
| A-591 | 4-Methoxyphenyl | Cyclopentyl | 1 | 4-F |
| A-592 | 4-Chlorophenyl | Cyclopentyl | 1 | 4-F |
| A-593 | 4-Fluorophenyl | Cyclopentyl | 1 | 4-F |
| A-594 | 2,4-Difluorophenyl | Cyclopentyl | 1 | 4-F |
| A-595 | 2,6-Difluorophenyl | Cyclopentyl | 1 | 4-F |
| A-596 | 3,5-Difluorophenyl | Cyclopentyl | 1 | 4-F |
| A-597 | 2,4-Dichlorophenyl | Cyclopentyl | 1 | 4-F |
| A-598 | 2,6-Dichlorophenyl | Cyclopentyl | 1 | 4-F |
| A-599 | 3,5-Dichlorophenyl | Cyclopentyl | 1 | 4-F |
| A-600 | 2-Chloro-4-fluorophenyl | Cyclopentyl | 1 | 4-F |
| A-601 | Pyridin-2-yl | Cyclopentyl | 1 | 4-F |
| A-602 | Pyridin-4-yl | Cyclopentyl | 1 | 4-F |
| A-603 | Thien-2-yl | Cyclopentyl | 1 | 4-F |
| A-604 | 3-Trifluoromethylphenyl | Cyclopentyl | 1 | 4-F |
| A-605 | 4-(Diethylamino-methyl)phenyl | Cyclopentyl | 1 | 4-F |
| A-606 | 4-(Morpholin-4-ylmethyl)phenyl | Cyclopentyl | 1 | 4-F |
| A-607 | 4-(Morpholin-4-yl)phenyl | Cyclopentyl | 1 | 4-F |
| A-608 | Phenyl | Cyclopropylmethyl | 1 | 4-F |
| A-609 | 2-Methylphenyl | Cyclopropylmethyl | 1 | 4-F |
| A-610 | 2-Methoxyphenyl | Cyclopropylmethyl | 1 | 4-F |
| A-611 | 2-Chlorophenyl | Cyclopropylmethyl | 1 | 4-F |
| A-612 | 2-Fluorophenyl | Cyclopropylmethyl | 1 | 4-F |
| A-613 | 3-Methylphenyl | Cyclopropylmethyl | 1 | 4-F |
| A-614 | 3-Methoxyphenyl | Cyclopropylmethyl | 1 | 4-F |
| A-615 | 3-Chlorophenyl | Cyclopropylmethyl | 1 | 4-F |
| A-616 | 3-Fluorophenyl | Cyclopropylmethyl | 1 | 4-F |
| A-617 | 4-Methylphenyl | Cyclopropylmethyl | 1 | 4-F |
| A-618 | 4-Methoxyphenyl | Cyclopropylmethyl | 1 | 4-F |
| A-619 | 4-Chlorophenyl | Cyclopropylmethyl | 1 | 4-F |
| A-620 | 4-Fluorophenyl | Cyclopropylmethyl | 1 | 4-F |
| A-621 | 2,4-Difluorophenyl | Cyclopropylmethyl | 1 | 4-F |
| A-622 | 2,6-Difluorophenyl | Cyclopropylmethyl | 1 | 4-F |
| A-623 | 3,5-Difluorophenyl | Cyclopropylmethyl | 1 | 4-F |
| A-624 | 2,4-Dichlorophenyl | Cyclopropylmethyl | 1 | 4-F |
| A-625 | 2,6-Dichlorophenyl | Cyclopropylmethyl | 1 | 4-F |
| A-626 | 3,5-Dichlorophenyl | Cyclopropylmethyl | 1 | 4-F |
| A-627 | 2-Chloro-4-fluorophenyl | Cyclopropylmethyl | 1 | 4-F |
| A-628 | Pyridin-2-yl | Cyclopropylmethyl | 1 | 4-F |
| A-629 | Pyridin-4-yl | Cyclopropylmethyl | 1 | 4-F |
| A-630 | Thien-2-yl | Cyclopropylmethyl | 1 | 4-F |
| A-631 | 3-Trifluoromethylphenyl | Cyclopropylmethyl | 1 | 4-F |
| A-632 | 4-(Diethylamino-methyl)phenyl | Cyclopropylmethyl | 1 | 4-F |
| A-633 | 4-(Morpholin-4-ylmethyl)phenyl | Cyclopropylmethyl | 1 | 4-F |
| A-634 | 4-(Morpholin-4-yl)phenyl | Cyclopropylmethyl | 1 | 4-F |
| A-635 | Phenyl | 2-(Morpholin-4-yl)ethyl | 1 | 4-F |
| A-636 | 2-Methylphenyl | 2-(Morpholin-4-yl)ethyl | 1 | 4-F |
| A-637 | 2-Methoxyphenyl | 2-(Morpholin-4-yl)ethyl | 1 | 4-F |
| A-638 | 2-Chlorophenyl | 2-(Morpholin-4-yl)ethyl | 1 | 4-F |
| A-639 | 2-Fluorophenyl | 2-(Morpholin-4-yl)ethyl | 1 | 4-F |
| A-640 | 3-Methylphenyl | 2-(Morpholin-4-yl)ethyl | 1 | 4-F |
| A-641 | 3-Methoxyphenyl | 2-(Morpholin-4-yl)ethyl | 1 | 4-F |
| A-642 | 3-Chlorophenyl | 2-(Morpholin-4-yl)ethyl | 1 | 4-F |
| A-643 | 3-Fluorophenyl | 2-(Morpholin-4-yl)ethyl | 1 | 4-F |
| A-644 | 4-Methylphenyl | 2-(Morpholin-4-yl)ethyl | 1 | 4-F |
| A-645 | 4-Methoxyphenyl | 2-(Morpholin-4-yl)ethyl | 1 | 4-F |
| A-646 | 4-Chlorophenyl | 2-(Morpholin-4-yl)ethyl | 1 | 4-F |
| A-647 | 4-Fluorophenyl | 2-(Morpholin-4-yl)ethyl | 1 | 4-F |
| A-648 | 2,4-Difluorophenyl | 2-(Morpholin-4-yl)ethyl | 1 | 4-F |
| A-649 | 2,6-Difluorophenyl | 2-(Morpholin-4-yl)ethyl | 1 | 4-F |
| A-650 | 3,5-Difluorophenyl | 2-(Morpholin-4-yl)ethyl | 1 | 4-F |

TABLE A-continued

| No. | R² | R³ | m | R⁵ |
|---|---|---|---|---|
| A-651 | 2,4-Dichlorophenyl | 2-(Morpholin-4-yl)ethyl | 1 | 4-F |
| A-652 | 2,6-Dichlorophenyl | 2-(Morpholin-4-yl)ethyl | 1 | 4-F |
| A-653 | 3,5-Dichlorophenyl | 2-(Morpholin-4-yl)ethyl | 1 | 4-F |
| A-654 | 2-Chloro-4-fluorophenyl | 2-(Morpholin-4-yl)ethyl | 1 | 4-F |
| A-655 | Pyridin-2-yl | 2-(Morpholin-4-yl)ethyl | 1 | 4-F |
| A-656 | Pyridin-4-yl | 2-(Morpholin-4-yl)ethyl | 1 | 4-F |
| A-657 | Thien-2-yl | 2-(Morpholin-4-yl)ethyl | 1 | 4-F |
| A-658 | 3-Trifluoromethylphenyl | 2-(Morpholin-4-yl)ethyl | 1 | 4-F |
| A-659 | 4-(Diethylamino-methyl)phenyl | 2-(Morpholin-4-yl)ethyl | 1 | 4-F |
| A-660 | 4-(Morpholin-4-ylmethyl)phenyl | 2-(Morpholin-4-yl)ethyl | 1 | 4-F |
| A-661 | 4-(Morpholin-4-yl)phenyl | 2-(Morpholin-4-yl)ethyl | 1 | 4-F |
| A-662 | Phenyl | Benzyl | 1 | 4-F |
| A-663 | 2-Methylphenyl | Benzyl | 1 | 4-F |
| A-664 | 2-Methoxyphenyl | Benzyl | 1 | 4-F |
| A-665 | 2-Chlorophenyl | Benzyl | 1 | 4-F |
| A-666 | 2-Fluorophenyl | Benzyl | 1 | 4-F |
| A-667 | 3-Methylphenyl | Benzyl | 1 | 4-F |
| A-668 | 3-Methoxyphenyl | Benzyl | 1 | 4-F |
| A-669 | 3-Chlorophenyl | Benzyl | 1 | 4-F |
| A-670 | 3-Fluorophenyl | Benzyl | 1 | 4-F |
| A-671 | 4-Methylphenyl | Benzyl | 1 | 4-F |
| A-672 | 4-Methoxyphenyl | Benzyl | 1 | 4-F |
| A-673 | 4-Chlorophenyl | Benzyl | 1 | 4-F |
| A-674 | 4-Fluorophenyl | Benzyl | 1 | 4-F |
| A-675 | 2,4-Difluorophenyl | Benzyl | 1 | 4-F |
| A-676 | 2,6-Difluorophenyl | Benzyl | 1 | 4-F |
| A-677 | 3,5-Difluorophenyl | Benzyl | 1 | 4-F |
| A-678 | 2,4-Dichlorophenyl | Benzyl | 1 | 4-F |
| A-679 | 2,6-Dichlorophenyl | Benzyl | 1 | 4-F |
| A-680 | 3,5-Dichlorophenyl | Benzyl | 1 | 4-F |
| A-681 | 2-Chloro-4-fluorophenyl | Benzyl | 1 | 4-F |
| A-682 | Pyridin-2-yl | Benzyl | 1 | 4-F |
| A-683 | Pyridin-4-yl | Benzyl | 1 | 4-F |
| A-684 | Thien-2-yl | Benzyl | 1 | 4-F |
| A-685 | 3-Trifluoromethylphenyl | Benzyl | 1 | 4-F |
| A-686 | 4-(Diethylamino-methyl)phenyl | Benzyl | 1 | 4-F |
| A-687 | 4-(Morpholin-4-ylmethyl)phenyl | Benzyl | 1 | 4-F |
| A-688 | 4-(Morpholin-4-yl)phenyl | Benzyl | 1 | 4-F |
| A-689 | Phenyl | Pyridin-2-yl-methyl | 1 | 4-F |
| A-690 | 2-Methylphenyl | Pyridin-2-yl-methyl | 1 | 4-F |
| A-691 | 2-Methoxyphenyl | Pyridin-2-yl-methyl | 1 | 4-F |
| A-692 | 2-Chlorophenyl | Pyridin-2-yl-methyl | 1 | 4-F |
| A-693 | 2-Fluorophenyl | Pyridin-2-yl-methyl | 1 | 4-F |
| A-694 | 3-Methylphenyl | Pyridin-2-yl-methyl | 1 | 4-F |
| A-695 | 3-Methoxyphenyl | Pyridin-2-yl-methyl | 1 | 4-F |
| A-696 | 3-Chlorophenyl | Pyridin-2-yl-methyl | 1 | 4-F |
| A-697 | 3-Fluorophenyl | Pyridin-2-yl-methyl | 1 | 4-F |
| A-698 | 4-Methylphenyl | Pyridin-2-yl-methyl | 1 | 4-F |
| A-699 | 4-Methoxyphenyl | Pyridin-2-yl-methyl | 1 | 4-F |
| A-700 | 4-Chlorophenyl | Pyridin-2-yl-methyl | 1 | 4-F |
| A-701 | 4-Fluorophenyl | Pyridin-2-yl-methyl | 1 | 4-F |
| A-702 | 2,4-Difluorophenyl | Pyridin-2-yl-methyl | 1 | 4-F |
| A-703 | 2,6-Difluorophenyl | Pyridin-2-yl-methyl | 1 | 4-F |
| A-704 | 3,5-Difluorophenyl | Pyridin-2-yl-methyl | 1 | 4-F |
| A-705 | 2,4-Dichlorophenyl | Pyridin-2-yl-methyl | 1 | 4-F |
| A-706 | 2,6-Dichlorophenyl | Pyridin-2-yl-methyl | 1 | 4-F |
| A-707 | 3,5-Dichlorophenyl | Pyridin-2-yl-methyl | 1 | 4-F |
| A-708 | 2-Chloro-4-fluorophenyl | Pyridin-2-yl-methyl | 1 | 4-F |
| A-709 | Pyridin-2-yl | Pyridin-2-yl-methyl | 1 | 4-F |
| A-710 | Pyridin-4-yl | Pyridin-2-yl-methyl | 1 | 4-F |
| A-711 | Thien-2-yl | Pyridin-2-yl-methyl | 1 | 4-F |
| A-712 | 3-Trifluoromethylphenyl | Pyridin-2-yl-methyl | 1 | 4-F |
| A-713 | 4-(Diethylamino-methyl)phenyl | Pyridin-2-yl-methyl | 1 | 4-F |
| A-714 | 4-(Morpholin-4-ylmethyl)phenyl | Pyridin-2-yl-methyl | 1 | 4-F |
| A-715 | 4-(Morpholin-4-yl)phenyl | Pyridin-2-yl-methyl | 1 | 4-F |
| A-716 | Cyclopropyl | Methyl | 1 | 4-F |
| A-717 | Cyclopropyl | Ethyl | 1 | 4-F |
| A-718 | Cyclopropyl | Allyl | 1 | 4-F |
| A-719 | Cyclopropyl | Cyclopropyl | 1 | 4-F |
| A-720 | Cyclopropyl | Propyl | 1 | 4-F |
| A-721 | Cyclopropyl | Isopropyl | 1 | 4-F |
| A-722 | Cyclopropyl | Tert.-Butyl | 1 | 4-F |
| A-723 | Cyclopropyl | Cyclobutyl | 1 | 4-F |
| A-724 | Cyclopropyl | Cyclopentyl | 1 | 4-F |
| A-725 | Cyclopropyl | Cyclopropylmethyl | 1 | 4-F |
| A-726 | Cyclopropyl | 2-(Morpholin-4-yl)ethyl | 1 | 4-F |
| A-727 | Cyclopropyl | Benzyl | 1 | 4-F |
| A-728 | Cyclopropyl | Pyridin-2-yl-methyl | 1 | 4-F |
| A-729 | Phenyl | Methyl | 1 | 5-F |
| A-730 | 2-Methylphenyl | Methyl | 1 | 5-F |
| A-731 | 2-Methoxyphenyl | Methyl | 1 | 5-F |
| A-732 | 2-Chlorophenyl | Methyl | 1 | 5-F |
| A-733 | 2-Fluorophenyl | Methyl | 1 | 5-F |
| A-734 | 3-Methylphenyl | Methyl | 1 | 5-F |
| A-735 | 3-Methoxyphenyl | Methyl | 1 | 5-F |
| A-736 | 3-Chlorophenyl | Methyl | 1 | 5-F |
| A-737 | 3-Fluorophenyl | Methyl | 1 | 5-F |
| A-738 | 4-Methylphenyl | Methyl | 1 | 5-F |
| A-739 | 4-Methoxyphenyl | Methyl | 1 | 5-F |
| A-740 | 4-Chlorophenyl | Methyl | 1 | 5-F |
| A-741 | 4-Fluorophenyl | Methyl | 1 | 5-F |
| A-742 | 2,4-Difluorophenyl | Methyl | 1 | 5-F |
| A-743 | 2,6-Difluorophenyl | Methyl | 1 | 5-F |
| A-744 | 3,5-Difluorophenyl | Methyl | 1 | 5-F |
| A-745 | 2,4-Dichlorophenyl | Methyl | 1 | 5-F |
| A-746 | 2,6-Dichlorophenyl | Methyl | 1 | 5-F |
| A-747 | 3,5-Dichlorophenyl | Methyl | 1 | 5-F |
| A-748 | 2-Chloro-4-fluorophenyl | Methyl | 1 | 5-F |
| A-749 | Pyridin-2-yl | Methyl | 1 | 5-F |
| A-750 | Pyridin-4-yl | Methyl | 1 | 5-F |
| A-751 | Thien-2-yl | Methyl | 1 | 5-F |
| A-752 | 3-Trifluoromethylphenyl | Methyl | 1 | 5-F |
| A-753 | 4-(Diethylamino-methyl)phenyl | Methyl | 1 | 5-F |
| A-754 | 4-(Morpholin-4-ylmethyl)phenyl | Methyl | | |
| A-755 | 4-(Morpholin-4-yl)phenyl | Methyl | 1 | 5-F |
| A-756 | Phenyl | Ethyl | 1 | 5-F |
| A-757 | 2-Methylphenyl | Ethyl | 1 | 5-F |
| A-758 | 2-Methoxyphenyl | Ethyl | 1 | 5-F |
| A-759 | 2-Chlorophenyl | Ethyl | 1 | 5-F |
| A-760 | 2-Fluorophenyl | Ethyl | 1 | 5-F |
| A-761 | 3-Methylphenyl | Ethyl | 1 | 5-F |
| A-762 | 3-Methoxyphenyl | Ethyl | 1 | 5-F |
| A-763 | 3-Chlorophenyl | Ethyl | 1 | 5-F |
| A-764 | 3-Fluorophenyl | Ethyl | 1 | 5-F |
| A-765 | 4-Methylphenyl | Ethyl | 1 | 5-F |
| A-766 | 4-Methoxyphenyl | Ethyl | 1 | 5-F |
| A-767 | 4-Chlorophenyl | Ethyl | 1 | 5-F |
| A-768 | 4-Fluorophenyl | Ethyl | 1 | 5-F |
| A-769 | 2,4-Difluorophenyl | Ethyl | 1 | 5-F |
| A-770 | 2,6-Difluorophenyl | Ethyl | 1 | 5-F |
| A-771 | 3,5-Difluorophenyl | Ethyl | 1 | 5-F |
| A-772 | 2,4-Dichlorophenyl | Ethyl | 1 | 5-F |
| A-773 | 2,6-Dichlorophenyl | Ethyl | 1 | 5-F |
| A-774 | 3,5-Dichlorophenyl | Ethyl | 1 | 5-F |
| A-775 | 2-Chloro-4-fluorophenyl | Ethyl | 1 | 5-F |
| A-776 | Pyridin-2-yl | Ethyl | 1 | 5-F |
| A-777 | Pyridin-4-yl | Ethyl | 1 | 5-F |
| A-778 | Thien-2-yl | Ethyl | 1 | 5-F |
| A-779 | 3-Trifluoromethylphenyl | Ethyl | 1 | 5-F |
| A-780 | 4-(Diethylamino-methyl)phenyl | Ethyl | 1 | 5-F |
| A-781 | 4-(Morpholin-4-ylmethyl)phenyl | Ethyl | | |
| A-782 | 4-(Morpholin-4-yl)phenyl | Ethyl | 1 | 5-F |
| A-783 | Phenyl | Allyl | 1 | 5-F |
| A-784 | 2-Methylphenyl | Allyl | 1 | 5-F |
| A-785 | 2-Methoxyphenyl | Allyl | 1 | 5-F |
| A-786 | 2-Chlorophenyl | Allyl | 1 | 5-F |
| A-787 | 2-Fluorophenyl | Allyl | 1 | 5-F |
| A-788 | 3-Methylphenyl | Allyl | 1 | 5-F |
| A-789 | 3-Methoxyphenyl | Allyl | 1 | 5-F |
| A-790 | 3-Chlorophenyl | Allyl | 1 | 5-F |
| A-791 | 3-Fluorophenyl | Allyl | 1 | 5-F |

TABLE A-continued

| No. | R² | R³ | m | R⁵ |
|---|---|---|---|---|
| A-792 | 4-Methylphenyl | Allyl | 1 | 5-F |
| A-793 | 4-Methoxyphenyl | Allyl | 1 | 5-F |
| A-794 | 4-Chlorophenyl | Allyl | 1 | 5-F |
| A-795 | 4-Fluorophenyl | Allyl | 1 | 5-F |
| A-796 | 2,4-Difluorophenyl | Allyl | 1 | 5-F |
| A-797 | 2,6-Difluorophenyl | Allyl | 1 | 5-F |
| A-798 | 3,5-Difluorophenyl | Allyl | 1 | 5-F |
| A-799 | 2,4-Dichlorophenyl | Allyl | 1 | 5-F |
| A-800 | 2,6-Dichlorophenyl | Allyl | 1 | 5-F |
| A-801 | 3,5-Dichlorophenyl | Allyl | 1 | 5-F |
| A-802 | 2-Chloro-4-fluorophenyl | Allyl | 1 | 5-F |
| A-803 | Pyridin-2-yl | Allyl | 1 | 5-F |
| A-804 | Pyridin-4-yl | Allyl | 1 | 5-F |
| A-805 | Thien-2-yl | Allyl | 1 | 5-F |
| A-806 | 3-Trifluoromethylphenyl | Allyl | 1 | 5-F |
| A-807 | 4-(Diethylamino-methyl)phenyl | Allyl | 1 | 5-F |
| A-808 | 4-(Morpholin-4-ylmethyl)phenyl | Allyl | 1 | 5-F |
| A-809 | 4-(Morpholin-4-yl)phenyl | Allyl | 1 | 5-F |
| A-810 | Phenyl | Cyclopropyl | 1 | 5-F |
| A-811 | 2-Methylphenyl | Cyclopropyl | 1 | 5-F |
| A-812 | 2-Methoxyphenyl | Cyclopropyl | 1 | 5-F |
| A-813 | 2-Chlorophenyl | Cyclopropyl | 1 | 5-F |
| A-814 | 2-Fluorophenyl | Cyclopropyl | 1 | 5-F |
| A-815 | 3-Methylphenyl | Cyclopropyl | 1 | 5-F |
| A-816 | 3-Methoxyphenyl | Cyclopropyl | 1 | 5-F |
| A-817 | 3-Chlorophenyl | Cyclopropyl | 1 | 5-F |
| A-818 | 3-Fluorophenyl | Cyclopropyl | 1 | 5-F |
| A-819 | 4-Methylphenyl | Cyclopropyl | 1 | 5-F |
| A-820 | 4-Methoxyphenyl | Cyclopropyl | 1 | 5-F |
| A-821 | 4-Chlorophenyl | Cyclopropyl | 1 | 5-F |
| A-822 | 4-Fluorophenyl | Cyclopropyl | 1 | 5-F |
| A-823 | 2,4-Difluorophenyl | Cyclopropyl | 1 | 5-F |
| A-824 | 2,6-Difluorophenyl | Cyclopropyl | 1 | 5-F |
| A-825 | 3,5-Difluorophenyl | Cyclopropyl | 1 | 5-F |
| A-826 | 2,4-Dichlorophenyl | Cyclopropyl | 1 | 5-F |
| A-827 | 2,6-Dichlorophenyl | Cyclopropyl | 1 | 5-F |
| A-828 | 3,5-Dichlorophenyl | Cyclopropyl | 1 | 5-F |
| A-829 | 2-Chloro-4-fluorophenyl | Cyclopropyl | 1 | 5-F |
| A-830 | Pyridin-2-yl | Cyclopropyl | 1 | 5-F |
| A-831 | Pyridin-4-yl | Cyclopropyl | 1 | 5-F |
| A-832 | Thien-2-yl | Cyclopropyl | 1 | 5-F |
| A-833 | 3-Trifluoromethylphenyl | Cyclopropyl | 1 | 5-F |
| A-834 | 4-(Diethylamino-methyl)phenyl | Cyclopropyl | 1 | 5-F |
| A-835 | 4-(Morpholin-4-ylmethyl)phenyl | Cyclopropyl | 1 | 5-F |
| A-836 | 4-(Morpholin-4-yl)phenyl | Cyclopropyl | 1 | 5-F |
| A-837 | Phenyl | Propyl | 1 | 5-F |
| A-838 | 2-Methylphenyl | Propyl | 1 | 5-F |
| A-839 | 2-Methoxyphenyl | Propyl | 1 | 5-F |
| A-840 | 2-Chlorophenyl | Propyl | 1 | 5-F |
| A-841 | 2-Fluorophenyl | Propyl | 1 | 5-F |
| A-842 | 3-Methylphenyl | Propyl | 1 | 5-F |
| A-843 | 3-Methoxyphenyl | Propyl | 1 | 5-F |
| A-844 | 3-Chlorophenyl | Propyl | 1 | 5-F |
| A-845 | 3-Fluorophenyl | Propyl | 1 | 5-F |
| A-846 | 4-Methylphenyl | Propyl | 1 | 5-F |
| A-847 | 4-Methoxyphenyl | Propyl | 1 | 5-F |
| A-848 | 4-Chlorophenyl | Propyl | 1 | 5-F |
| A-849 | 4-Fluorophenyl | Propyl | 1 | 5-F |
| A-850 | 2,4-Difluorophenyl | Propyl | 1 | 5-F |
| A-851 | 2,6-Difluorophenyl | Propyl | 1 | 5-F |
| A-852 | 3,5-Difluorophenyl | Propyl | 1 | 5-F |
| A-853 | 2,4-Dichlorophenyl | Propyl | 1 | 5-F |
| A-854 | 2,6-Dichlorophenyl | Propyl | 1 | 5-F |
| A-855 | 3,5-Dichlorophenyl | Propyl | 1 | 5-F |
| A-856 | 2-Chloro-4-fluorophenyl | Propyl | 1 | 5-F |
| A-857 | Pyridin-2-yl | Propyl | 1 | 5-F |
| A-858 | Pyridin-4-yl | Propyl | 1 | 5-F |
| A-859 | Thien-2-yl | Propyl | 1 | 5-F |
| A-860 | 3-Trifluoromethylphenyl | Propyl | 1 | 5-F |
| A-861 | 4-(Diethylamino-methyl)phenyl | Propyl | 1 | 5-F |
| A-862 | 4-(Morpholin-4-ylmethyl)phenyl | Propyl | 1 | 5-F |
| A-863 | 4-(Morpholin-4-yl)phenyl | Propyl | 1 | 5-F |
| A-864 | Phenyl | Isopropyl | 1 | 5-F |
| A-865 | 2-Methylphenyl | Isopropyl | 1 | 5-F |
| A-866 | 2-Methoxyphenyl | Isopropyl | 1 | 5-F |
| A-867 | 2-Chlorophenyl | Isopropyl | 1 | 5-F |
| A-868 | 2-Fluorophenyl | Isopropyl | 1 | 5-F |
| A-869 | 3-Methylphenyl | Isopropyl | 1 | 5-F |
| A-870 | 3-Methoxyphenyl | Isopropyl | 1 | 5-F |
| A-871 | 3-Chlorophenyl | Isopropyl | 1 | 5-F |
| A-872 | 3-Fluorophenyl | Isopropyl | 1 | 5-F |
| A-873 | 4-Methylphenyl | Isopropyl | 1 | 5-F |
| A-874 | 4-Methoxyphenyl | Isopropyl | 1 | 5-F |
| A-875 | 4-Chlorophenyl | Isopropyl | 1 | 5-F |
| A-876 | 4-Fluorophenyl | Isopropyl | 1 | 5-F |
| A-877 | 2,4-Difluorophenyl | Isopropyl | 1 | 5-F |
| A-878 | 2,6-Difluorophenyl | Isopropyl | 1 | 5-F |
| A-879 | 3,5-Difluorophenyl | Isopropyl | 1 | 5-F |
| A-880 | 2,4-Dichlorophenyl | Isopropyl | 1 | 5-F |
| A-881 | 2,6-Dichlorophenyl | Isopropyl | 1 | 5-F |
| A-882 | 3,5-Dichlorophenyl | Isopropyl | 1 | 5-F |
| A-883 | 2-Chloro-4-fluorophenyl | Isopropyl | 1 | 5-F |
| A-884 | Pyridin-2-yl | Isopropyl | 1 | 5-F |
| A-885 | Pyridin-4-yl | Isopropyl | 1 | 5-F |
| A-886 | Thien-2-yl | Isopropyl | 1 | 5-F |
| A-887 | 3-Trifluoromethylphenyl | Isopropyl | 1 | 5-F |
| A-888 | 4-(Diethylamino-methyl)phenyl | Isopropyl | 1 | 5-F |
| A-889 | 4-(Morpholin-4-ylmethyl)phenyl | Isopropyl | 1 | 5-F |
| A-890 | 4-(Morpholin-4-yl)phenyl | Isopropyl | 1 | 5-F |
| A-891 | Phenyl | Tert.butyl | 1 | 5-F |
| A-892 | 2-Methylphenyl | Tert.butyl | 1 | 5-F |
| A-893 | 2-Methoxyphenyl | Tert.butyl | 1 | 5-F |
| A-894 | 2-Chlorophenyl | Tert.butyl | 1 | 5-F |
| A-895 | 2-Fluorophenyl | Tert.butyl | 1 | 5-F |
| A-896 | 3-Methylphenyl | Tert.butyl | 1 | 5-F |
| A-897 | 3-Methoxyphenyl | Tert.butyl | 1 | 5-F |
| A-898 | 3-Chlorophenyl | Tert.butyl | 1 | 5-F |
| A-899 | 3-Fluorophenyl | Tert.butyl | 1 | 5-F |
| A-900 | 4-Methylphenyl | Tert.butyl | 1 | 5-F |
| A-901 | 4-Methoxyphenyl | Tert.butyl | 1 | 5-F |
| A-902 | 4-Chlorophenyl | Tert.butyl | 1 | 5-F |
| A-903 | 4-Fluorophenyl | Tert.butyl | 1 | 5-F |
| A-904 | 2,4-Difluorophenyl | Tert.butyl | 1 | 5-F |
| A-905 | 2,6-Difluorophenyl | Tert.butyl | 1 | 5-F |
| A-906 | 3,5-Difluorophenyl | Tert.butyl | 1 | 5-F |
| A-907 | 2,4-Dichlorophenyl | Tert.butyl | 1 | 5-F |
| A-908 | 2,6-Dichlorophenyl | Tert.butyl | 1 | 5-F |
| A-909 | 3,5-Dichlorophenyl | Tert.butyl | 1 | 5-F |
| A-910 | 2-Chloro-4-fluorophenyl | Tert.butyl | 1 | 5-F |
| A-911 | Pyridin-2-yl | Tert.butyl | 1 | 5-F |
| A-912 | Pyridin-4-yl | Tert.butyl | 1 | 5-F |
| A-913 | Thien-2-yl | Tert.butyl | 1 | 5-F |
| A-914 | 3-Trifluoromethylphenyl | Tert.butyl | 1 | 5-F |
| A-915 | 4-(Diethylamino-methyl)phenyl | Tert.butyl | 1 | 5-F |
| A-916 | 4-(Morpholin-4-ylmethyl)phenyl | Tert.butyl | 1 | 5-F |
| A-917 | 4-(Morpholin-4-yl)phenyl | Tert.butyl | 1 | 5-F |
| A-918 | Phenyl | Cyclobutyl | 1 | 5-F |
| A-919 | 2-Methylphenyl | Cyclobutyl | 1 | 5-F |
| A-920 | 2-Methoxyphenyl | Cyclobutyl | 1 | 5-F |
| A-921 | 2-Chlorophenyl | Cyclobutyl | 1 | 5-F |
| A-922 | 2-Fluorophenyl | Cyclobutyl | 1 | 5-F |
| A-923 | 3-Methylphenyl | Cyclobutyl | 1 | 5-F |
| A-924 | 3-Methoxyphenyl | Cyclobutyl | 1 | 5-F |
| A-925 | 3-Chlorophenyl | Cyclobutyl | 1 | 5-F |
| A-926 | 3-Fluorophenyl | Cyclobutyl | 1 | 5-F |
| A-927 | 4-Methylphenyl | Cyclobutyl | 1 | 5-F |
| A-928 | 4-Methoxyphenyl | Cyclobutyl | 1 | 5-F |
| A-929 | 4-Chlorophenyl | Cyclobutyl | 1 | 5-F |
| A-930 | 4-Fluorophenyl | Cyclobutyl | 1 | 5-F |
| A-931 | 2,4-Difluorophenyl | Cyclobutyl | 1 | 5-F |

TABLE A-continued

| No. | R² | R³ | m | R⁵ |
|---|---|---|---|---|
| A-932 | 2,6-Difluorophenyl | Cyclobutyl | 1 | 5-F |
| A-933 | 3,5-Difluorophenyl | Cyclobutyl | 1 | 5-F |
| A-934 | 2,4-Dichlorophenyl | Cyclobutyl | 1 | 5-F |
| A-935 | 2,6-Dichlorophenyl | Cyclobutyl | 1 | 5-F |
| A-936 | 3,5-Dichlorophenyl | Cyclobutyl | 1 | 5-F |
| A-937 | 2-Chloro-4-fluorophenyl | Cyclobutyl | 1 | 5-F |
| A-938 | Pyridin-2-yl | Cyclobutyl | 1 | 5-F |
| A-939 | Pyridin-4-yl | Cyclobutyl | 1 | 5-F |
| A-940 | Thien-2-yl | Cyclobutyl | 1 | 5-F |
| A-941 | 3-Trifluoromethylphenyl | Cyclobutyl | 1 | 5-F |
| A-942 | 4-(Diethylamino-methyl)phenyl | Cyclobutyl | 1 | 5-F |
| A-943 | 4-(Morpholin-4-ylmethyl)phenyl | Cyclobutyl | 1 | 5-F |
| A-944 | 4-(Morpholin-4-yl)phenyl | Cyclobutyl | 1 | 5-F |
| A-945 | Phenyl | Cyclopentyl | 1 | 5-F |
| A-946 | 2-Methylphenyl | Cyclopentyl | 1 | 5-F |
| A-947 | 2-Methoxyphenyl | Cyclopentyl | 1 | 5-F |
| A-948 | 2-Chlorophenyl | Cyclopentyl | 1 | 5-F |
| A-949 | 2-Fluorophenyl | Cyclopentyl | 1 | 5-F |
| A-950 | 3-Methylphenyl | Cyclopentyl | 1 | 5-F |
| A-951 | 3-Methoxyphenyl | Cyclopentyl | 1 | 5-F |
| A-952 | 3-Chlorophenyl | Cyclopentyl | 1 | 5-F |
| A-953 | 3-Fluorophenyl | Cyclopentyl | 1 | 5-F |
| A-954 | 4-Methylphenyl | Cyclopentyl | 1 | 5-F |
| A-955 | 4-Methoxyphenyl | Cyclopentyl | 1 | 5-F |
| A-956 | 4-Chlorophenyl | Cyclopentyl | 1 | 5-F |
| A-957 | 4-Fluorophenyl | Cyclopentyl | 1 | 5-F |
| A-958 | 2,4-Difluorophenyl | Cyclopentyl | 1 | 5-F |
| A-959 | 2,6-Difluorophenyl | Cyclopentyl | 1 | 5-F |
| A-960 | 3,5-Difluorophenyl | Cyclopentyl | 1 | 5-F |
| A-961 | 2,4-Dichlorophenyl | Cyclopentyl | 1 | 5-F |
| A-962 | 2,6-Dichlorophenyl | Cyclopentyl | 1 | 5-F |
| A-963 | 3,5-Dichlorophenyl | Cyclopentyl | 1 | 5-F |
| A-964 | 2-Chloro-4-fluorophenyl | Cyclopentyl | 1 | 5-F |
| A-965 | Pyridin-2-yl | Cyclopentyl | 1 | 5-F |
| A-966 | Pyridin-4-yl | Cyclopentyl | 1 | 5-F |
| A-967 | Thien-2-yl | Cyclopentyl | 1 | 5-F |
| A-968 | 3-Trifluoromethylphenyl | Cyclopentyl | 1 | 5-F |
| A-969 | 4-(Diethylamino-methyl)phenyl | Cyclopentyl | 1 | 5-F |
| A-970 | 4-(Morpholin-4-ylmethyl)phenyl | Cyclopentyl | 1 | 5-F |
| A-971 | 4-(Morpholin-4-yl)phenyl | Cyclopentyl | 1 | 5-F |
| A-972 | Phenyl | Cyclopropylmethyl | 1 | 5-F |
| A-973 | 2-Methylphenyl | Cyclopropylmethyl | 1 | 5-F |
| A-974 | 2-Methoxyphenyl | Cyclopropylmethyl | 1 | 5-F |
| A-975 | 2-Chlorophenyl | Cyclopropylmethyl | 1 | 5-F |
| A-976 | 2-Fluorophenyl | Cyclopropylmethyl | 1 | 5-F |
| A-977 | 3-Methylphenyl | Cyclopropylmethyl | 1 | 5-F |
| A-978 | 3-Methoxyphenyl | Cyclopropylmethyl | 1 | 5-F |
| A-979 | 3-Chlorophenyl | Cyclopropylmethyl | 1 | 5-F |
| A-980 | 3-Fluorophenyl | Cyclopropylmethyl | 1 | 5-F |
| A-981 | 4-Methylphenyl | Cyclopropylmethyl | 1 | 5-F |
| A-982 | 4-Methoxyphenyl | Cyclopropylmethyl | 1 | 5-F |
| A-983 | 4-Chlorophenyl | Cyclopropylmethyl | 1 | 5-F |
| A-984 | 4-Fluorophenyl | Cyclopropylmethyl | 1 | 5-F |
| A-985 | 2,4-Difluorophenyl | Cyclopropylmethyl | 1 | 5-F |
| A-986 | 2,6-Difluorophenyl | Cyclopropylmethyl | 1 | 5-F |
| A-987 | 3,5-Difluorophenyl | Cyclopropylmethyl | 1 | 5-F |
| A-988 | 2,4-Dichlorophenyl | Cyclopropylmethyl | 1 | 5-F |
| A-989 | 2,6-Dichlorophenyl | Cyclopropylmethyl | 1 | 5-F |
| A-990 | 3,5-Dichlorophenyl | Cyclopropylmethyl | 1 | 5-F |
| A-991 | 2-Chloro-4-fluorophenyl | Cyclopropylmethyl | 1 | 5-F |
| A-992 | Pyridin-2-yl | Cyclopropylmethyl | 1 | 5-F |
| A-993 | Pyridin-4-yl | Cyclopropylmethyl | 1 | 5-F |
| A-994 | Thien-2-yl | Cyclopropylmethyl | 1 | 5-F |
| A-995 | 3-Trifluoromethylphenyl | Cyclopropylmethyl | 1 | 5-F |
| A-996 | 4-(Diethylamino-methyl)phenyl | Cyclopropylmethyl | 1 | 5-F |
| A-997 | 4-(Morpholin-4-ylmethyl)phenyl | Cyclopropylmethyl | 1 | 5-F |
| A-998 | 4-(Morpholin-4-yl)phenyl | Cyclopropylmethyl | 1 | 5-F |
| A-999 | Phenyl | 2-(Morpholin-4-yl)ethyl | 1 | 5-F |
| A-1000 | 2-Methylphenyl | 2-(Morpholin-4-yl)ethyl | 1 | 5-F |
| A-1001 | 2-Methoxyphenyl | 2-(Morpholin-4-yl)ethyl | 1 | 5-F |
| A-1002 | 2-Chlorophenyl | 2-(Morpholin-4-yl)ethyl | 1 | 5-F |
| A-1003 | 2-Fluorophenyl | 2-(Morpholin-4-yl)ethyl | 1 | 5-F |
| A-1004 | 3-Methylphenyl | 2-(Morpholin-4-yl)ethyl | 1 | 5-F |
| A-1005 | 3-Methoxyphenyl | 2-(Morpholin-4-yl)ethyl | 1 | 5-F |
| A-1006 | 3-Chlorophenyl | 2-(Morpholin-4-yl)ethyl | 1 | 5-F |
| A-1007 | 3-Fluorophenyl | 2-(Morpholin-4-yl)ethyl | 1 | 5-F |
| A-1008 | 4-Methylphenyl | 2-(Morpholin-4-yl)ethyl | 1 | 5-F |
| A-1009 | 4-Methoxyphenyl | 2-(Morpholin-4-yl)ethyl | 1 | 5-F |
| A-1010 | 4-Chlorophenyl | 2-(Morpholin-4-yl)ethyl | 1 | 5-F |
| A-1011 | 4-Fluorophenyl | 2-(Morpholin-4-yl)ethyl | 1 | 5-F |
| A-1012 | 2,4-Difluorophenyl | 2-(Morpholin-4-yl)ethyl | 1 | 5-F |
| A-1013 | 2,6-Difluorophenyl | 2-(Morpholin-4-yl)ethyl | 1 | 5-F |
| A-1014 | 3,5-Difluorophenyl | 2-(Morpholin-4-yl)ethyl | 1 | 5-F |
| A-1015 | 2,4-Dichlorophenyl | 2-(Morpholin-4-yl)ethyl | 1 | 5-F |
| A-1016 | 2,6-Dichlorophenyl | 2-(Morpholin-4-yl)ethyl | 1 | 5-F |
| A-1017 | 3,5-Dichlorophenyl | 2-(Morpholin-4-yl)ethyl | 1 | 5-F |
| A-1018 | 2-Chloro-4-fluorophenyl | 2-(Morpholin-4-yl)ethyl | 1 | 5-F |
| A-1019 | Pyridin-2-yl | 2-(Morpholin-4-yl)ethyl | 1 | 5-F |
| A-1020 | Pyridin-4-yl | 2-(Morpholin-4-yl)ethyl | 1 | 5-F |
| A-1021 | Thien-2-yl | 2-(Morpholin-4-yl)ethyl | 1 | 5-F |
| A-1022 | 3-Trifluoromethylphenyl | 2-(Morpholin-4-yl)ethyl | 1 | 5-F |
| A-1023 | 4-(Diethylamino-methyl)phenyl | 2-(Morpholin-4-yl)ethyl | 1 | 5-F |
| A-1024 | 4-(Morpholin-4-ylmethyl)phenyl | 2-(Morpholin-4-yl)ethyl | 1 | 5-F |
| A-1025 | 4-(Morpholin-4-yl)phenyl | 2-(Morpholin-4-yl)ethyl | 1 | 5-F |
| A-1026 | Phenyl | Benzyl | 1 | 5-F |
| A-1027 | 2-Methylphenyl | Benzyl | 1 | 5-F |
| A-1028 | 2-Methoxyphenyl | Benzyl | 1 | 5-F |
| A-1029 | 2-Chlorophenyl | Benzyl | 1 | 5-F |
| A-1030 | 2-Fluorophenyl | Benzyl | 1 | 5-F |
| A-1031 | 3-Methylphenyl | Benzyl | 1 | 5-F |
| A-1032 | 3-Methoxyphenyl | Benzyl | 1 | 5-F |
| A-1033 | 3-Chlorophenyl | Benzyl | 1 | 5-F |
| A-1034 | 3-Fluorophenyl | Benzyl | 1 | 5-F |
| A-1035 | 4-Methylphenyl | Benzyl | 1 | 5-F |
| A-1036 | 4-Methoxyphenyl | Benzyl | 1 | 5-F |
| A-1037 | 4-Chlorophenyl | Benzyl | 1 | 5-F |
| A-1038 | 4-Fluorophenyl | Benzyl | 1 | 5-F |
| A-1039 | 2,4-Difluorophenyl | Benzyl | 1 | 5-F |
| A-1040 | 2,6-Difluorophenyl | Benzyl | 1 | 5-F |
| A-1041 | 3,5-Difluorophenyl | Benzyl | 1 | 5-F |
| A-1042 | 2,4-Dichlorophenyl | Benzyl | 1 | 5-F |
| A-1043 | 2,6-Dichlorophenyl | Benzyl | 1 | 5-F |
| A-1044 | 3,5-Dichlorophenyl | Benzyl | 1 | 5-F |
| A-1045 | 2-Chloro-4-fluorophenyl | Benzyl | 1 | 5-F |
| A-1046 | Pyridin-2-yl | Benzyl | 1 | 5-F |
| A-1047 | Pyridin-4-yl | Benzyl | 1 | 5-F |
| A-1048 | Thien-2-yl | Benzyl | 1 | 5-F |
| A-1049 | 3-Trifluoromethylphenyl | Benzyl | 1 | 5-F |
| A-1050 | 4-(Diethylamino-methyl)phenyl | Benzyl | 1 | 5-F |
| A-1051 | 4-(Morpholin-4-ylmethyl)phenyl | Benzyl | 1 | 5-F |
| A-1052 | 4-(Morpholin-4-yl)phenyl | Benzyl | 1 | 5-F |
| A-1053 | Phenyl | Pyridin-2-yl-methyl | 1 | 5-F |
| A-1054 | 2-Methylphenyl | Pyridin-2-yl-methyl | 1 | 5-F |
| A-1055 | 2-Methoxyphenyl | Pyridin-2-yl-methyl | 1 | 5-F |
| A-1056 | 2-Chlorophenyl | Pyridin-2-yl-methyl | 1 | 5-F |
| A-1057 | 2-Fluorophenyl | Pyridin-2-yl-methyl | 1 | 5-F |
| A-1058 | 3-Methylphenyl | Pyridin-2-yl-methyl | 1 | 5-F |
| A-1059 | 3-Methoxyphenyl | Pyridin-2-yl-methyl | 1 | 5-F |
| A-1060 | 3-Chlorophenyl | Pyridin-2-yl-methyl | 1 | 5-F |
| A-1061 | 3-Fluorophenyl | Pyridin-2-yl-methyl | 1 | 5-F |
| A-1062 | 4-Methylphenyl | Pyridin-2-yl-methyl | 1 | 5-F |
| A-1063 | 4-Methoxyphenyl | Pyridin-2-yl-methyl | 1 | 5-F |
| A-1064 | 4-Chlorophenyl | Pyridin-2-yl-methyl | 1 | 5-F |
| A-1065 | 4-Fluorophenyl | Pyridin-2-yl-methyl | 1 | 5-F |
| A-1066 | 2,4-Difluorophenyl | Pyridin-2-yl-methyl | 1 | 5-F |
| A-1067 | 2,6-Difluorophenyl | Pyridin-2-yl-methyl | 1 | 5-F |
| A-1068 | 3,5-Difluorophenyl | Pyridin-2-yl-methyl | 1 | 5-F |
| A-1069 | 2,4-Dichlorophenyl | Pyridin-2-yl-methyl | 1 | 5-F |
| A-1070 | 2,6-Dichlorophenyl | Pyridin-2-yl-methyl | 1 | 5-F |
| A-1071 | 3,5-Dichlorophenyl | Pyridin-2-yl-methyl | 1 | 5-F |
| A-1072 | 2-Chloro-4-fluorophenyl | Pyridin-2-yl-methyl | 1 | 5-F |

TABLE A-continued

| No. | R² | R³ | m | R⁵ |
|---|---|---|---|---|
| A-1073 | Pyridin-2-yl | Pyridin-2-yl-methyl | 1 | 5-F |
| A-1074 | Pyridin-4-yl | Pyridin-2-yl-methyl | 1 | 5-F |
| A-1075 | Thien-2-yl | Pyridin-2-yl-methyl | 1 | 5-F |
| A-1076 | 3-Trifluoromethylphenyl | Pyridin-2-yl-methyl | 1 | 5-F |
| A-1077 | 4-(Diethylamino-methyl)phenyl | Pyridin-2-yl-methyl | 1 | 5-F |
| A-1078 | 4-(Morpholin-4-ylmethyl)phenyl | Pyridin-2-yl-methyl | 1 | 5-F |
| A-1079 | 4-(Morpholin-4-yl)phenyl | Pyridin-2-yl-methyl | 1 | 5-F |
| A-1080 | Cyclopropyl | Methyl | 1 | 5-F |
| A-1081 | Cyclopropyl | Ethyl | 1 | 5-F |
| A-1082 | Cyclopropyl | Allyl | 1 | 5-F |
| A-1083 | Cyclopropyl | Cyclopropyl | 1 | 5-F |
| A-1084 | Cyclopropyl | Propyl | 1 | 5-F |
| A-1085 | Cyclopropyl | Isopropyl | 1 | 5-F |
| A-1086 | Cyclopropyl | Tert.-Butyl | 1 | 5-F |
| A-1087 | Cyclopropyl | Cyclobutyl | 1 | 5-F |
| A-1088 | Cyclopropyl | Cyclopentyl | 1 | 5-F |
| A-1089 | Cyclopropyl | Cyclopropylmethyl | 1 | 5-F |
| A-1090 | Cyclopropyl | 2-(Morpholin-4-yl)ethyl | 1 | 5-F |
| A-1091 | Cyclopropyl | Benzyl | 1 | 5-F |
| A-1092 | Cyclopropyl | Pyridin-2-yl-methyl | 1 | 5-F |
| A-1093 | Phenyl | Methyl | 1 | 4-Cl |
| A-1094 | 2-Methylphenyl | Methyl | 1 | 4-Cl |
| A-1095 | 2-Methoxyphenyl | Methyl | 1 | 4-Cl |
| A-1096 | 2-Chlorophenyl | Methyl | 1 | 4-Cl |
| A-1097 | 2-Fluorophenyl | Methyl | 1 | 4-Cl |
| A-1098 | 3-Methylphenyl | Methyl | 1 | 4-Cl |
| A-1099 | 3-Methoxyphenyl | Methyl | 1 | 4-Cl |
| A-1100 | 3-Chlorophenyl | Methyl | 1 | 4-Cl |
| A-1101 | 3-Fluorophenyl | Methyl | 1 | 4-Cl |
| A-1102 | 4-Methylphenyl | Methyl | 1 | 4-Cl |
| A-1103 | 4-Methoxyphenyl | Methyl | 1 | 4-Cl |
| A-1104 | 4-Chlorophenyl | Methyl | 1 | 4-Cl |
| A-1105 | 4-Fluorophenyl | Methyl | 1 | 4-Cl |
| A-1106 | 2,4-Difluorophenyl | Methyl | 1 | 4-Cl |
| A-1107 | 2,6-Difluorophenyl | Methyl | 1 | 4-Cl |
| A-1108 | 3,5-Difluorophenyl | Methyl | 1 | 4-Cl |
| A-1109 | 2,4-Dichlorophenyl | Methyl | 1 | 4-Cl |
| A-1110 | 2,6-Dichlorophenyl | Methyl | 1 | 4-Cl |
| A-1111 | 3,5-Dichlorophenyl | Methyl | 1 | 4-Cl |
| A-1112 | 2-Chloro-4-fluorophenyl | Methyl | 1 | 4-Cl |
| A-1113 | Pyridin-2-yl | Methyl | 1 | 4-Cl |
| A-1114 | Pyridin-4-yl | Methyl | 1 | 4-Cl |
| A-1115 | Thien-2-yl | Methyl | 1 | 4-Cl |
| A-1116 | 3-Trifluoromethylphenyl | Methyl | 1 | 4-Cl |
| A-1117 | 4-(Diethylamino-methyl)phenyl | Methyl | 1 | 4-Cl |
| A-1118 | 4-(Morpholin-4-ylmethyl)phenyl | Methyl | 1 | 4-Cl |
| A-1119 | 4-(Morpholin-4-yl)phenyl | Methyl | 1 | 4-Cl |
| A-1120 | Phenyl | Ethyl | 1 | 4-Cl |
| A-1121 | 2-Methylphenyl | Ethyl | 1 | 4-Cl |
| A-1122 | 2-Methoxyphenyl | Ethyl | 1 | 4-Cl |
| A-1123 | 2-Chlorophenyl | Ethyl | 1 | 4-Cl |
| A-1124 | 2-Fluorophenyl | Ethyl | 1 | 4-Cl |
| A-1125 | 3-Methylphenyl | Ethyl | 1 | 4-Cl |
| A-1126 | 3-Methoxyphenyl | Ethyl | 1 | 4-Cl |
| A-1127 | 3-Chlorophenyl | Ethyl | 1 | 4-Cl |
| A-1128 | 3-Fluorophenyl | Ethyl | 1 | 4-Cl |
| A-1129 | 4-Methylphenyl | Ethyl | 1 | 4-Cl |
| A-1130 | 4-Methoxyphenyl | Ethyl | 1 | 4-Cl |
| A-1131 | 4-Chlorophenyl | Ethyl | 1 | 4-Cl |
| A-1132 | 4-Fluorophenyl | Ethyl | 1 | 4-Cl |
| A-1133 | 2,4-Difluorophenyl | Ethyl | 1 | 4-Cl |
| A-1134 | 2,6-Difluorophenyl | Ethyl | 1 | 4-Cl |
| A-1135 | 3,5-Difluorophenyl | Ethyl | 1 | 4-Cl |
| A-1136 | 2,4-Dichlorophenyl | Ethyl | 1 | 4-Cl |
| A-1137 | 2,6-Dichlorophenyl | Ethyl | 1 | 4-Cl |
| A-1138 | 3,5-Dichlorophenyl | Ethyl | 1 | 4-Cl |
| A-1139 | 2-Chloro-4-fluorophenyl | Ethyl | 1 | 4-Cl |
| A-1140 | Pyridin-2-yl | Ethyl | 1 | 4-Cl |
| A-1141 | Pyridin-4-yl | Ethyl | 1 | 4-Cl |
| A-1142 | Thien-2-yl | Ethyl | 1 | 4-Cl |
| A-1143 | 3-Trifluoromethylphenyl | Ethyl | 1 | 4-Cl |
| A-1144 | 4-(Diethylamino-methyl)phenyl | Ethyl | 1 | 4-Cl |
| A-1145 | 4-(Morpholin-4-ylmethyl)phenyl | Ethyl | 1 | 4-Cl |
| A-1146 | 4-(Morpholin-4-yl)phenyl | Ethyl | 1 | 4-Cl |
| A-1147 | Phenyl | Allyl | 1 | 4-Cl |
| A-1148 | 2-Methylphenyl | Allyl | 1 | 4-Cl |
| A-1149 | 2-Methoxyphenyl | Allyl | 1 | 4-Cl |
| A-1150 | 2-Chlorophenyl | Allyl | 1 | 4-Cl |
| A-1151 | 2-Fluorophenyl | Allyl | 1 | 4-Cl |
| A-1152 | 3-Methylphenyl | Allyl | 1 | 4-Cl |
| A-1153 | 3-Methoxyphenyl | Allyl | 1 | 4-Cl |
| A-1154 | 3-Chlorophenyl | Allyl | 1 | 4-Cl |
| A-1155 | 3-Fluorophenyl | Allyl | 1 | 4-Cl |
| A-1156 | 4-Methylphenyl | Allyl | 1 | 4-Cl |
| A-1157 | 4-Methoxyphenyl | Allyl | 1 | 4-Cl |
| A-1158 | 4-Chlorophenyl | Allyl | 1 | 4-Cl |
| A-1159 | 4-Fluorophenyl | Allyl | 1 | 4-Cl |
| A-1160 | 2,4-Difluorophenyl | Allyl | 1 | 4-Cl |
| A-1161 | 2,6-Difluorophenyl | Allyl | 1 | 4-Cl |
| A-1162 | 3,5-Difluorophenyl | Allyl | 1 | 4-Cl |
| A-1163 | 2,4-Dichlorophenyl | Allyl | 1 | 4-Cl |
| A-1164 | 2,6-Dichlorophenyl | Allyl | 1 | 4-Cl |
| A-1165 | 3,5-Dichlorophenyl | Allyl | 1 | 4-Cl |
| A-1166 | 2-Chloro-4-fluorophenyl | Allyl | 1 | 4-Cl |
| A-1167 | Pyridin-2-yl | Allyl | 1 | 4-Cl |
| A-1168 | Pyridin-4-yl | Allyl | 1 | 4-Cl |
| A-1169 | Thien-2-yl | Allyl | 1 | 4-Cl |
| A-1170 | 3-Trifluoromethylphenyl | Allyl | 1 | 4-Cl |
| A-1171 | 4-(Diethylamino-methyl)phenyl | Allyl | 1 | 4-Cl |
| A-1172 | 4-(Morpholin-4-ylmethyl)phenyl | Allyl | 1 | 4-Cl |
| A-1173 | 4-(Morpholin-4-yl)phenyl | Allyl | 1 | 4-Cl |
| A-1174 | Phenyl | Cyclopropyl | 1 | 4-Cl |
| A-1175 | 2-Methylphenyl | Cyclopropyl | 1 | 4-Cl |
| A-1176 | 2-Methoxyphenyl | Cyclopropyl | 1 | 4-Cl |
| A-1177 | 2-Chlorophenyl | Cyclopropyl | 1 | 4-Cl |
| A-1178 | 2-Fluorophenyl | Cyclopropyl | 1 | 4-Cl |
| A-1179 | 3-Methylphenyl | Cyclopropyl | 1 | 4-Cl |
| A-1180 | 3-Methoxyphenyl | Cyclopropyl | 1 | 4-Cl |
| A-1181 | 3-Chlorophenyl | Cyclopropyl | 1 | 4-Cl |
| A-1182 | 3-Fluorophenyl | Cyclopropyl | 1 | 4-Cl |
| A-1183 | 4-Methylphenyl | Cyclopropyl | 1 | 4-Cl |
| A-1184 | 4-Methoxyphenyl | Cyclopropyl | 1 | 4-Cl |
| A-1185 | 4-Chlorophenyl | Cyclopropyl | 1 | 4-Cl |
| A-1186 | 4-Fluorophenyl | Cyclopropyl | 1 | 4-Cl |
| A-1187 | 2,4-Difluorophenyl | Cyclopropyl | 1 | 4-Cl |
| A-1188 | 2,6-Difluorophenyl | Cyclopropyl | 1 | 4-Cl |
| A-1189 | 3,5-Difluorophenyl | Cyclopropyl | 1 | 4-Cl |
| A-1190 | 2,4-Dichlorophenyl | Cyclopropyl | 1 | 4-Cl |
| A-1191 | 2,6-Dichlorophenyl | Cyclopropyl | 1 | 4-Cl |
| A-1192 | 3,5-Dichlorophenyl | Cyclopropyl | 1 | 4-Cl |
| A-1193 | 2-Chloro-4-fluorophenyl | Cyclopropyl | 1 | 4-Cl |
| A-1194 | Pyridin-2-yl | Cyclopropyl | 1 | 4-Cl |
| A-1195 | Pyridin-4-yl | Cyclopropyl | 1 | 4-Cl |
| A-1196 | Thien-2-yl | Cyclopropyl | 1 | 4-Cl |
| A-1197 | 3-Trifluoromethylphenyl | Cyclopropyl | 1 | 4-Cl |
| A-1198 | 4-(Diethylamino-methyl)phenyl | Cyclopropyl | 1 | 4-Cl |
| A-1199 | 4-(Morpholin-4-ylmethyl)phenyl | Cyclopropyl | 1 | 4-Cl |
| A-1200 | 4-(Morpholin-4-yl)phenyl | Cyclopropyl | 1 | 4-Cl |
| A-1201 | Phenyl | Propyl | 1 | 4-Cl |
| A-1202 | 2-Methylphenyl | Propyl | 1 | 4-Cl |
| A-1203 | 2-Methoxyphenyl | Propyl | 1 | 4-Cl |
| A-1204 | 2-Chlorophenyl | Propyl | 1 | 4-Cl |
| A-1205 | 2-Fluorophenyl | Propyl | 1 | 4-Cl |
| A-1206 | 3-Methylphenyl | Propyl | 1 | 4-Cl |
| A-1207 | 3-Methoxyphenyl | Propyl | 1 | 4-Cl |
| A-1208 | 3-Chlorophenyl | Propyl | 1 | 4-Cl |
| A-1209 | 3-Fluorophenyl | Propyl | 1 | 4-Cl |
| A-1210 | 4-Methylphenyl | Propyl | 1 | 4-Cl |
| A-1211 | 4-Methoxyphenyl | Propyl | 1 | 4-Cl |

TABLE A-continued

| No. | R² | R³ | m | R⁵ |
|---|---|---|---|---|
| A-1212 | 4-Chlorophenyl | Propyl | 1 | 4-Cl |
| A-1213 | 4-Fluorophenyl | Propyl | 1 | 4-Cl |
| A-1214 | 2,4-Difluorophenyl | Propyl | 1 | 4-Cl |
| A-1215 | 2,6-Difluorophenyl | Propyl | 1 | 4-Cl |
| A-1216 | 3,5-Difluorophenyl | Propyl | 1 | 4-Cl |
| A-1217 | 2,4-Dichlorophenyl | Propyl | 1 | 4-Cl |
| A-1218 | 2,6-Dichlorophenyl | Propyl | 1 | 4-Cl |
| A-1219 | 3,5-Dichlorophenyl | Propyl | 1 | 4-Cl |
| A-1220 | 2-Chloro-4-fluorophenyl | Propyl | 1 | 4-Cl |
| A-1221 | Pyridin-2-yl | Propyl | 1 | 4-Cl |
| A-1222 | Pyridin-4-yl | Propyl | 1 | 4-Cl |
| A-1223 | Thien-2-yl | Propyl | 1 | 4-Cl |
| A-1224 | 3-Trifluoromethylphenyl | Propyl | 1 | 4-Cl |
| A-1225 | 4-(Diethylamino-methyl)phenyl | Propyl | 1 | 4-Cl |
| A-1226 | 4-(Morpholin-4-ylmethyl)phenyl | Propyl | 1 | 4-Cl |
| A-1227 | 4-(Morpholin-4-yl)phenyl | Propyl | 1 | 4-Cl |
| A-1228 | Phenyl | Isopropyl | 1 | 4-Cl |
| A-1229 | 2-Methylphenyl | Isopropyl | 1 | 4-Cl |
| A-1230 | 2-Methoxyphenyl | Isopropyl | 1 | 4-Cl |
| A-1231 | 2-Chlorophenyl | Isopropyl | 1 | 4-Cl |
| A-1232 | 2-Fluorophenyl | Isopropyl | 1 | 4-Cl |
| A-1233 | 3-Methylphenyl | Isopropyl | 1 | 4-Cl |
| A-1234 | 3-Methoxyphenyl | Isopropyl | 1 | 4-Cl |
| A-1235 | 3-Chlorophenyl | Isopropyl | 1 | 4-Cl |
| A-1236 | 3-Fluorophenyl | Isopropyl | 1 | 4-Cl |
| A-1237 | 4-Methylphenyl | Isopropyl | 1 | 4-Cl |
| A-1238 | 4-Methoxyphenyl | Isopropyl | 1 | 4-Cl |
| A-1239 | 4-Chlorophenyl | Isopropyl | 1 | 4-Cl |
| A-1240 | 4-Fluorophenyl | Isopropyl | 1 | 4-Cl |
| A-1241 | 2,4-Difluorophenyl | Isopropyl | 1 | 4-Cl |
| A-1242 | 2,6-Difluorophenyl | Isopropyl | 1 | 4-Cl |
| A-1243 | 3,5-Difluorophenyl | Isopropyl | 1 | 4-Cl |
| A-1244 | 2,4-Dichlorophenyl | Isopropyl | 1 | 4-Cl |
| A-1245 | 2,6-Dichlorophenyl | Isopropyl | 1 | 4-Cl |
| A-1246 | 3,5-Dichlorophenyl | Isopropyl | 1 | 4-Cl |
| A-1247 | 2-Chloro-4-fluorophenyl | Isopropyl | 1 | 4-Cl |
| A-1248 | Pyridin-2-yl | Isopropyl | 1 | 4-Cl |
| A-1249 | Pyridin-4-yl | Isopropyl | 1 | 4-Cl |
| A-1250 | Thien-2-yl | Isopropyl | 1 | 4-Cl |
| A-1251 | 3-Trifluoromethylphenyl | Isopropyl | 1 | 4-Cl |
| A-1252 | 4-(Diethylamino-methyl)phenyl | Isopropyl | 1 | 4-Cl |
| A-1253 | 4-(Morpholin-4-ylmethyl)phenyl | Isopropyl | 1 | 4-Cl |
| A-1254 | 4-(Morpholin-4-yl)phenyl | Isopropyl | 1 | 4-Cl |
| A-1255 | Phenyl | Tert.butyl | 1 | 4-Cl |
| A-1256 | 2-Methylphenyl | Tert.butyl | 1 | 4-Cl |
| A-1257 | 2-Methoxyphenyl | Tert.butyl | 1 | 4-Cl |
| A-1258 | 2-Chlorophenyl | Tert.butyl | 1 | 4-Cl |
| A-1259 | 2-Fluorophenyl | Tert.butyl | 1 | 4-Cl |
| A-1260 | 3-Methylphenyl | Tert.butyl | 1 | 4-Cl |
| A-1261 | 3-Methoxyphenyl | Tert.butyl | 1 | 4-Cl |
| A-1262 | 3-Chlorophenyl | Tert.butyl | 1 | 4-Cl |
| A-1263 | 3-Fluorophenyl | Tert.butyl | 1 | 4-Cl |
| A-1264 | 4-Methylphenyl | Tert.butyl | 1 | 4-Cl |
| A-1265 | 4-Methoxyphenyl | Tert.butyl | 1 | 4-Cl |
| A-1266 | 4-Chlorophenyl | Tert.butyl | 1 | 4-Cl |
| A-1267 | 4-Fluorophenyl | Tert.butyl | 1 | 4-Cl |
| A-1268 | 2,4-Difluorophenyl | Tert.butyl | 1 | 4-Cl |
| A-1269 | 2,6-Difluorophenyl | Tert.butyl | 1 | 4-Cl |
| A-1270 | 3,5-Difluorophenyl | Tert.butyl | 1 | 4-Cl |
| A-1271 | 2,4-Dichlorophenyl | Tert.butyl | 1 | 4-Cl |
| A-1272 | 2,6-Dichlorophenyl | Tert.butyl | 1 | 4-Cl |
| A-1273 | 3,5-Dichlorophenyl | Tert.butyl | 1 | 4-Cl |
| A-1274 | 2-Chloro-4-fluorophenyl | Tert.butyl | 1 | 4-Cl |
| A-1275 | Pyridin-2-yl | Tert.butyl | 1 | 4-Cl |
| A-1276 | Pyridin-4-yl | Tert.butyl | 1 | 4-Cl |
| A-1277 | Thien-2-yl | Tert.butyl | 1 | 4-Cl |
| A-1278 | 3-Trifluoromethylphenyl | Tert.butyl | 1 | 4-Cl |
| A-1279 | 4-(Diethylamino-methyl)phenyl | Tert.butyl | 1 | 4-Cl |
| A-1280 | 4-(Morpholin-4-ylmethyl)phenyl | Tert.butyl | 1 | 4-Cl |
| A-1281 | 4-(Morpholin-4-yl)phenyl | Tert.butyl | 1 | 4-Cl |
| A-1282 | Phenyl | Cyclobutyl | 1 | 4-Cl |
| A-1283 | 2-Methylphenyl | Cyclobutyl | 1 | 4-Cl |
| A-1284 | 2-Methoxyphenyl | Cyclobutyl | 1 | 4-Cl |
| A-1285 | 2-Chlorophenyl | Cyclobutyl | 1 | 4-Cl |
| A-1286 | 2-Fluorophenyl | Cyclobutyl | 1 | 4-Cl |
| A-1287 | 3-Methylphenyl | Cyclobutyl | 1 | 4-Cl |
| A-1288 | 3-Methoxyphenyl | Cyclobutyl | 1 | 4-Cl |
| A-1289 | 3-Chlorophenyl | Cyclobutyl | 1 | 4-Cl |
| A-1290 | 3-Fluorophenyl | Cyclobutyl | 1 | 4-Cl |
| A-1291 | 4-Methylphenyl | Cyclobutyl | 1 | 4-Cl |
| A-1292 | 4-Methoxyphenyl | Cyclobutyl | 1 | 4-Cl |
| A-1293 | 4-Chlorophenyl | Cyclobutyl | 1 | 4-Cl |
| A-1294 | 4-Fluorophenyl | Cyclobutyl | 1 | 4-Cl |
| A-1295 | 2,4-Difluorophenyl | Cyclobutyl | 1 | 4-Cl |
| A-1296 | 2,6-Difluorophenyl | Cyclobutyl | 1 | 4-Cl |
| A-1297 | 3,5-Difluorophenyl | Cyclobutyl | 1 | 4-Cl |
| A-1298 | 2,4-Dichlorophenyl | Cyclobutyl | 1 | 4-Cl |
| A-1299 | 2,6-Dichlorophenyl | Cyclobutyl | 1 | 4-Cl |
| A-1300 | 3,5-Dichlorophenyl | Cyclobutyl | 1 | 4-Cl |
| A-1301 | 2-Chloro-4-fluorophenyl | Cyclobutyl | 1 | 4-Cl |
| A-1302 | Pyridin-2-yl | Cyclobutyl | 1 | 4-Cl |
| A-1303 | Pyridin-4-yl | Cyclobutyl | 1 | 4-Cl |
| A-1304 | Thien-2-yl | Cyclobutyl | 1 | 4-Cl |
| A-1305 | 3-Trifluoromethylphenyl | Cyclobutyl | 1 | 4-Cl |
| A-1306 | 4-(Diethylamino-methyl)phenyl | Cyclobutyl | 1 | 4-Cl |
| A-1307 | 4-(Morpholin-4-ylmethyl)phenyl | Cyclobutyl | 1 | 4-Cl |
| A-1308 | 4-(Morpholin-4-yl)phenyl | Cyclobutyl | 1 | 4-Cl |
| A-1309 | Phenyl | Cyclopentyl | 1 | 4-Cl |
| A-1310 | 2-Methylphenyl | Cyclopentyl | 1 | 4-Cl |
| A-1311 | 2-Methoxyphenyl | Cyclopentyl | 1 | 4-Cl |
| A-1312 | 2-Chlorophenyl | Cyclopentyl | 1 | 4-Cl |
| A-1313 | 2-Fluorophenyl | Cyclopentyl | 1 | 4-Cl |
| A-1314 | 3-Methylphenyl | Cyclopentyl | 1 | 4-Cl |
| A-1315 | 3-Methoxyphenyl | Cyclopentyl | 1 | 4-Cl |
| A-1316 | 3-Chlorophenyl | Cyclopentyl | 1 | 4-Cl |
| A-1317 | 3-Fluorophenyl | Cyclopentyl | 1 | 4-Cl |
| A-1318 | 4-Methylphenyl | Cyclopentyl | 1 | 4-Cl |
| A-1319 | 4-Methoxyphenyl | Cyclopentyl | 1 | 4-Cl |
| A-1320 | 4-Chlorophenyl | Cyclopentyl | 1 | 4-Cl |
| A-1321 | 4-Fluorophenyl | Cyclopentyl | 1 | 4-Cl |
| A-1322 | 2,4-Difluorophenyl | Cyclopentyl | 1 | 4-Cl |
| A-1323 | 2,6-Difluorophenyl | Cyclopentyl | 1 | 4-Cl |
| A-1324 | 3,5-Difluorophenyl | Cyclopentyl | 1 | 4-Cl |
| A-1325 | 2,4-Dichlorophenyl | Cyclopentyl | 1 | 4-Cl |
| A-1326 | 2,6-Dichlorophenyl | Cyclopentyl | 1 | 4-Cl |
| A-1327 | 3,5-Dichlorophenyl | Cyclopentyl | 1 | 4-Cl |
| A-1328 | 2-Chloro-4-fluorophenyl | Cyclopentyl | 1 | 4-Cl |
| A-1329 | Pyridin-2-yl | Cyclopentyl | 1 | 4-Cl |
| A-1330 | Pyridin-4-yl | Cyclopentyl | 1 | 4-Cl |
| A-1331 | Thien-2-yl | Cyclopentyl | 1 | 4-Cl |
| A-1332 | 3-Trifluoromethylphenyl | Cyclopentyl | 1 | 4-Cl |
| A-1333 | 4-(Diethylamino-methyl)phenyl | Cyclopentyl | 1 | 4-Cl |
| A-1334 | 4-(Morpholin-4-ylmethyl)phenyl | Cyclopentyl | 1 | 4-Cl |
| A-1335 | 4-(Morpholin-4-yl)phenyl | Cyclopentyl | 1 | 4-Cl |
| A-1336 | Phenyl | Cyclopropylmethyl | 1 | 4-Cl |
| A-1337 | 2-Methylphenyl | Cyclopropylmethyl | 1 | 4-Cl |
| A-1338 | 2-Methoxyphenyl | Cyclopropylmethyl | 1 | 4-Cl |
| A-1339 | 2-Chlorophenyl | Cyclopropylmethyl | 1 | 4-Cl |
| A-1340 | 2-Fluorophenyl | Cyclopropylmethyl | 1 | 4-Cl |
| A-1341 | 3-Methylphenyl | Cyclopropylmethyl | 1 | 4-Cl |
| A-1342 | 3-Methoxyphenyl | Cyclopropylmethyl | 1 | 4-Cl |
| A-1343 | 3-Chlorophenyl | Cyclopropylmethyl | 1 | 4-Cl |
| A-1344 | 3-Fluorophenyl | Cyclopropylmethyl | 1 | 4-Cl |
| A-1345 | 4-Methylphenyl | Cyclopropylmethyl | 1 | 4-Cl |
| A-1346 | 4-Methoxyphenyl | Cyclopropylmethyl | 1 | 4-Cl |
| A-1347 | 4-Chlorophenyl | Cyclopropylmethyl | 1 | 4-Cl |
| A-1348 | 4-Fluorophenyl | Cyclopropylmethyl | 1 | 4-Cl |
| A-1349 | 2,4-Difluorophenyl | Cyclopropylmethyl | 1 | 4-Cl |
| A-1350 | 2,6-Difluorophenyl | Cyclopropylmethyl | 1 | 4-Cl |
| A-1351 | 3,5-Difluorophenyl | Cyclopropylmethyl | 1 | 4-Cl |

TABLE A-continued

| No. | R² | R³ | m | R⁵ |
|---|---|---|---|---|
| A-1352 | 2,4-Dichlorophenyl | Cyclopropylmethyl | 1 | 4-Cl |
| A-1353 | 2,6-Dichlorophenyl | Cyclopropylmethyl | 1 | 4-Cl |
| A-1354 | 3,5-Dichlorophenyl | Cyclopropylmethyl | 1 | 4-Cl |
| A-1355 | 2-Chloro-4-fluorophenyl | Cyclopropylmethyl | 1 | 4-Cl |
| A-1356 | Pyridin-2-yl | Cyclopropylmethyl | 1 | 4-Cl |
| A-1357 | Pyridin-4-yl | Cyclopropylmethyl | 1 | 4-Cl |
| A-1358 | Thien-2-yl | Cyclopropylmethyl | 1 | 4-Cl |
| A-1359 | 3-Trifluoromethylphenyl | Cyclopropylmethyl | 1 | 4-Cl |
| A-1360 | 4-(Diethylamino-methyl)phenyl | Cyclopropylmethyl | 1 | 4-Cl |
| A-1361 | 4-(Morpholin-4-ylmethyl)phenyl | Cyclopropylmethyl | 1 | 4-Cl |
| A-1362 | 4-(Morpholin-4-yl)phenyl | Cyclopropylmethyl | 1 | 4-Cl |
| A-1363 | Phenyl | 2-(Morpholin-4-yl)ethyl | 1 | 4-Cl |
| A-1364 | 2-Methylphenyl | 2-(Morpholin-4-yl)ethyl | 1 | 4-Cl |
| A-1365 | 2-Methoxyphenyl | 2-(Morpholin-4-yl)ethyl | 1 | 4-Cl |
| A-1366 | 2-Chlorophenyl | 2-(Morpholin-4-yl)ethyl | 1 | 4-Cl |
| A-1367 | 2-Fluorophenyl | 2-(Morpholin-4-yl)ethyl | 1 | 4-Cl |
| A-1368 | 3-Methylphenyl | 2-(Morpholin-4-yl)ethyl | 1 | 4-Cl |
| A-1369 | 3-Methoxyphenyl | 2-(Morpholin-4-yl)ethyl | 1 | 4-Cl |
| A-1370 | 3-Chlorophenyl | 2-(Morpholin-4-yl)ethyl | 1 | 4-Cl |
| A-1371 | 3-Fluorophenyl | 2-(Morpholin-4-yl)ethyl | 1 | 4-Cl |
| A-1372 | 4-Methylphenyl | 2-(Morpholin-4-yl)ethyl | 1 | 4-Cl |
| A-1373 | 4-Methoxyphenyl | 2-(Morpholin-4-yl)ethyl | 1 | 4-Cl |
| A-1374 | 4-Chlorophenyl | 2-(Morpholin-4-yl)ethyl | 1 | 4-Cl |
| A-1375 | 4-Fluorophenyl | 2-(Morpholin-4-yl)ethyl | 1 | 4-Cl |
| A-1376 | 2,4-Difluorophenyl | 2-(Morpholin-4-yl)ethyl | 1 | 4-Cl |
| A-1377 | 2,6-Difluorophenyl | 2-(Morpholin-4-yl)ethyl | 1 | 4-Cl |
| A-1378 | 3,5-Difluorophenyl | 2-(Morpholin-4-yl)ethyl | 1 | 4-Cl |
| A-1379 | 2,4-Dichlorophenyl | 2-(Morpholin-4-yl)ethyl | 1 | 4-Cl |
| A-1380 | 2,6-Dichlorophenyl | 2-(Morpholin-4-yl)ethyl | 1 | 4-Cl |
| A-1381 | 3,5-Dichlorophenyl | 2-(Morpholin-4-yl)ethyl | 1 | 4-Cl |
| A-1382 | 2-Chloro-4-fluorophenyl | 2-(Morpholin-4-yl)ethyl | 1 | 4-Cl |
| A-1383 | Pyridin-2-yl | 2-(Morpholin-4-yl)ethyl | 1 | 4-Cl |
| A-1384 | Pyridin-4-yl | 2-(Morpholin-4-yl)ethyl | 1 | 4-Cl |
| A-1385 | Thien-2-yl | 2-(Morpholin-4-yl)ethyl | 1 | 4-Cl |
| A-1386 | 3-Trifluoromethylphenyl | 2-(Morpholin-4-yl)ethyl | 1 | 4-Cl |
| A-1387 | 4-(Diethylamino-methyl)phenyl | 2-(Morpholin-4-yl)ethyl | 1 | 4-Cl |
| A-1388 | 4-(Morpholin-4-ylmethyl)phenyl | 2-(Morpholin-4-yl)ethyl | 1 | 4-Cl |
| A-1389 | 4-(Morpholin-4-yl)phenyl | 2-(Morpholin-4-yl)ethyl | 1 | 4-Cl |
| A-1390 | Phenyl | Benzyl | 1 | 4-Cl |
| A-1391 | 2-Methylphenyl | Benzyl | 1 | 4-Cl |
| A-1392 | 2-Methoxyphenyl | Benzyl | 1 | 4-Cl |
| A-1393 | 2-Chlorophenyl | Benzyl | 1 | 4-Cl |
| A-1394 | 2-Fluorophenyl | Benzyl | 1 | 4-Cl |
| A-1395 | 3-Methylphenyl | Benzyl | 1 | 4-Cl |
| A-1396 | 3-Methoxyphenyl | Benzyl | 1 | 4-Cl |
| A-1397 | 3-Chlorophenyl | Benzyl | 1 | 4-Cl |
| A-1398 | 3-Fluorophenyl | Benzyl | 1 | 4-Cl |
| A-1399 | 4-Methylphenyl | Benzyl | 1 | 4-Cl |
| A-1400 | 4-Methoxyphenyl | Benzyl | 1 | 4-Cl |
| A-1401 | 4-Chlorophenyl | Benzyl | 1 | 4-Cl |
| A-1402 | 4-Fluorophenyl | Benzyl | 1 | 4-Cl |
| A-1403 | 2,4-Difluorophenyl | Benzyl | 1 | 4-Cl |
| A-1404 | 2,6-Difluorophenyl | Benzyl | 1 | 4-Cl |
| A-1405 | 3,5-Difluorophenyl | Benzyl | 1 | 4-Cl |
| A-1406 | 2,4-Dichlorophenyl | Benzyl | 1 | 4-Cl |
| A-1407 | 2,6-Dichlorophenyl | Benzyl | 1 | 4-Cl |
| A-1408 | 3,5-Dichlorophenyl | Benzyl | 1 | 4-Cl |
| A-1409 | 2-Chloro-4-fluorophenyl | Benzyl | 1 | 4-Cl |
| A-1410 | Pyridin-2-yl | Benzyl | 1 | 4-Cl |
| A-1411 | Pyridin-4-yl | Benzyl | 1 | 4-Cl |
| A-1412 | Thien-2-yl | Benzyl | 1 | 4-Cl |
| A-1413 | 3-Trifluoromethylphenyl | Benzyl | 1 | 4-Cl |
| A-1414 | 4-(Diethylamino-methyl)phenyl | Benzyl | 1 | 4-Cl |
| A-1415 | 4-(Morpholin-4-ylmethyl)phenyl | Benzyl | 1 | 4-Cl |
| A-1416 | 4-(Morpholin-4-yl)phenyl | Benzyl | 1 | 4-Cl |
| A-1417 | Phenyl | Pyridin-2-yl-methyl | 1 | 4-Cl |
| A-1418 | 2-Methylphenyl | Pyridin-2-yl-methyl | 1 | 4-Cl |
| A-1419 | 2-Methoxyphenyl | Pyridin-2-yl-methyl | 1 | 4-Cl |
| A-1420 | 2-Chlorophenyl | Pyridin-2-yl-methyl | 1 | 4-Cl |
| A-1421 | 2-Fluorophenyl | Pyridin-2-yl-methyl | 1 | 4-Cl |
| A-1422 | 3-Methylphenyl | Pyridin-2-yl-methyl | 1 | 4-Cl |
| A-1423 | 3-Methoxyphenyl | Pyridin-2-yl-methyl | 1 | 4-Cl |
| A-1424 | 3-Chlorophenyl | Pyridin-2-yl-methyl | 1 | 4-Cl |
| A-1425 | 3-Fluorophenyl | Pyridin-2-yl-methyl | 1 | 4-Cl |
| A-1426 | 4-Methylphenyl | Pyridin-2-yl-methyl | 1 | 4-Cl |
| A-1427 | 4-Methoxyphenyl | Pyridin-2-yl-methyl | 1 | 4-Cl |
| A-1428 | 4-Chlorophenyl | Pyridin-2-yl-methyl | 1 | 4-Cl |
| A-1429 | 4-Fluorophenyl | Pyridin-2-yl-methyl | 1 | 4-Cl |
| A-1430 | 2,4-Difluorophenyl | Pyridin-2-yl-methyl | 1 | 4-Cl |
| A-1431 | 2,6-Difluorophenyl | Pyridin-2-yl-methyl | 1 | 4-Cl |
| A-1432 | 3,5-Difluorophenyl | Pyridin-2-yl-methyl | 1 | 4-Cl |
| A-1433 | 2,4-Dichlorophenyl | Pyridin-2-yl-methyl | 1 | 4-Cl |
| A-1434 | 2,6-Dichlorophenyl | Pyridin-2-yl-methyl | 1 | 4-Cl |
| A-1435 | 3,5-Dichlorophenyl | Pyridin-2-yl-methyl | 1 | 4-Cl |
| A-1436 | 2-Chloro-4-fluorophenyl | Pyridin-2-yl-methyl | 1 | 4-Cl |
| A-1437 | Pyridin-2-yl | Pyridin-2-yl-methyl | 1 | 4-Cl |
| A-1438 | Pyridin-4-yl | Pyridin-2-yl-methyl | 1 | 4-Cl |
| A-1439 | Thien-2-yl | Pyridin-2-yl-methyl | 1 | 4-Cl |
| A-1440 | 3-Trifluoromethylphenyl | Pyridin-2-yl-methyl | 1 | 4-Cl |
| A-1441 | 4-(Diethylamino-methyl)phenyl | Pyridin-2-yl-methyl | 1 | 4-Cl |
| A-1442 | 4-(Morpholin-4-ylmethyl)phenyl | Pyridin-2-yl-methyl | 1 | 4-Cl |
| A-1443 | 4-(Morpholin-4-yl)phenyl | Pyridin-2-yl-methyl | 1 | 4-Cl |
| A-1444 | Cyclopropyl | Methyl | 1 | 4-Cl |
| A-1445 | Cyclopropyl | Ethyl | 1 | 4-Cl |
| A-1446 | Cyclopropyl | Allyl | 1 | 4-Cl |
| A-1447 | Cyclopropyl | Cyclopropyl | 1 | 4-Cl |
| A-1448 | Cyclopropyl | Propyl | 1 | 4-Cl |
| A-1449 | Cyclopropyl | Isopropyl | 1 | 4-Cl |
| A-1450 | Cyclopropyl | Tert.-Butyl | 1 | 4-Cl |
| A-1451 | Cyclopropyl | Cyclobutyl | 1 | 4-Cl |
| A-1452 | Cyclopropyl | Cyclopentyl | 1 | 4-Cl |
| A-1453 | Cyclopropyl | Cyclopropylmethyl | 1 | 4-Cl |
| A-1454 | Cyclopropyl | 2-(Morpholin-4-yl)ethyl | 1 | 4-Cl |
| A-1455 | Cyclopropyl | Benzyl | 1 | 4-Cl |
| A-1456 | Cyclopropyl | Pyridin-2-yl-methyl | 1 | 4-Cl |
| A-1457 | Phenyl | Methyl | 1 | 5-Cl |
| A-1458 | 2-Methylphenyl | Methyl | 1 | 5-Cl |
| A-1459 | 2-Methoxyphenyl | Methyl | 1 | 5-Cl |
| A-1460 | 2-Chlorophenyl | Methyl | 1 | 5-Cl |
| A-1461 | 2-Fluorophenyl | Methyl | 1 | 5-Cl |
| A-1462 | 3-Methylphenyl | Methyl | 1 | 5-Cl |
| A-1463 | 3-Methoxyphenyl | Methyl | 1 | 5-Cl |
| A-1464 | 3-Chlorophenyl | Methyl | 1 | 5-Cl |
| A-1465 | 3-Fluorophenyl | Methyl | 1 | 5-Cl |
| A-1466 | 4-Methylphenyl | Methyl | 1 | 5-Cl |
| A-1467 | 4-Methoxyphenyl | Methyl | 1 | 5-Cl |
| A-1468 | 4-Chlorophenyl | Methyl | 1 | 5-Cl |
| A-1469 | 4-Fluorophenyl | Methyl | 1 | 5-Cl |
| A-1470 | 2,4-Difluorophenyl | Methyl | 1 | 5-Cl |
| A-1471 | 2,6-Difluorophenyl | Methyl | 1 | 5-Cl |
| A-1472 | 3,5-Difluorophenyl | Methyl | 1 | 5-Cl |
| A-1473 | 2,4-Dichlorophenyl | Methyl | 1 | 5-Cl |
| A-1474 | 2,6-Dichlorophenyl | Methyl | 1 | 5-Cl |
| A-1475 | 3,5-Dichlorophenyl | Methyl | 1 | 5-Cl |
| A-1476 | 2-Chloro-4-fluorophenyl | Methyl | 1 | 5-Cl |
| A-1477 | Pyridin-2-yl | Methyl | 1 | 5-Cl |
| A-1478 | Pyridin-4-yl | Methyl | 1 | 5-Cl |
| A-1479 | Thien-2-yl | Methyl | 1 | 5-Cl |
| A-1480 | 3-Trifluoromethylphenyl | Methyl | 1 | 5-Cl |
| A-1481 | 4-(Diethylamino-methyl)phenyl | Methyl | 1 | 5-Cl |
| A-1482 | 4-(Morpholin-4-ylmethyl)phenyl | Methyl | 1 | 5-Cl |
| A-1483 | 4-(Morpholin-4-yl)phenyl | Methyl | 1 | 5-Cl |
| A-1484 | Phenyl | Ethyl | 1 | 5-Cl |
| A-1485 | 2-Methylphenyl | Ethyl | 1 | 5-Cl |
| A-1486 | 2-Methoxyphenyl | Ethyl | 1 | 5-Cl |
| A-1487 | 2-Chlorophenyl | Ethyl | 1 | 5-Cl |
| A-1488 | 2-Fluorophenyl | Ethyl | 1 | 5-Cl |
| A-1489 | 3-Methylphenyl | Ethyl | 1 | 5-Cl |
| A-1490 | 3-Methoxyphenyl | Ethyl | 1 | 5-Cl |
| A-1491 | 3-Chlorophenyl | Ethyl | 1 | 5-Cl |
| A-1492 | 3-Fluorophenyl | Ethyl | 1 | 5-Cl |

TABLE A-continued

| No. | R² | R³ | m | R⁵ |
|---|---|---|---|---|
| A-1493 | 4-Methylphenyl | Ethyl | 1 | 5-Cl |
| A-1494 | 4-Methoxyphenyl | Ethyl | 1 | 5-Cl |
| A-1495 | 4-Chlorophenyl | Ethyl | 1 | 5-Cl |
| A-1496 | 4-Fluorophenyl | Ethyl | 1 | 5-Cl |
| A-1497 | 2,4-Difluorophenyl | Ethyl | 1 | 5-Cl |
| A-1498 | 2,6-Difluorophenyl | Ethyl | 1 | 5-Cl |
| A-1499 | 3,5-Difluorophenyl | Ethyl | 1 | 5-Cl |
| A-1500 | 2,4-Dichlorophenyl | Ethyl | 1 | 5-Cl |
| A-1501 | 2,6-Dichlorophenyl | Ethyl | 1 | 5-Cl |
| A-1502 | 3,5-Dichlorophenyl | Ethyl | 1 | 5-Cl |
| A-1503 | 2-Chloro-4-fluorophenyl | Ethyl | 1 | 5-Cl |
| A-1504 | Pyridin-2-yl | Ethyl | 1 | 5-Cl |
| A-1505 | Pyridin-4-yl | Ethyl | 1 | 5-Cl |
| A-1506 | Thien-2-yl | Ethyl | 1 | 5-Cl |
| A-1507 | 3-Trifluoromethylphenyl | Ethyl | 1 | 5-Cl |
| A-1508 | 4-(Diethylamino-methyl)phenyl | Ethyl | 1 | 5-Cl |
| A-1509 | 4-(Morpholin-4-ylmethyl)phenyl | Ethyl | 1 | 5-Cl |
| A-1510 | 4-(Morpholin-4-yl)phenyl | Ethyl | 1 | 5-Cl |
| A-1511 | Phenyl | Allyl | 1 | 5-Cl |
| A-1512 | 2-Methylphenyl | Allyl | 1 | 5-Cl |
| A-1513 | 2-Methoxyphenyl | Allyl | 1 | 5-Cl |
| A-1514 | 2-Chlorophenyl | Allyl | 1 | 5-Cl |
| A-1515 | 2-Fluorophenyl | Allyl | 1 | 5-Cl |
| A-1516 | 3-Methylphenyl | Allyl | 1 | 5-Cl |
| A-1517 | 3-Methoxyphenyl | Allyl | 1 | 5-Cl |
| A-1518 | 3-Chlorophenyl | Allyl | 1 | 5-Cl |
| A-1519 | 3-Fluorophenyl | Allyl | 1 | 5-Cl |
| A-1520 | 4-Methylphenyl | Allyl | 1 | 5-Cl |
| A-1521 | 4-Methoxyphenyl | Allyl | 1 | 5-Cl |
| A-1522 | 4-Chlorophenyl | Allyl | 1 | 5-Cl |
| A-1523 | 4-Fluorophenyl | Allyl | 1 | 5-Cl |
| A-1524 | 2,4-Difluorophenyl | Allyl | 1 | 5-Cl |
| A-1525 | 2,6-Difluorophenyl | Allyl | 1 | 5-Cl |
| A-1526 | 3,5-Difluorophenyl | Allyl | 1 | 5-Cl |
| A-1527 | 2,4-Dichlorophenyl | Allyl | 1 | 5-Cl |
| A-1528 | 2,6-Dichlorophenyl | Allyl | 1 | 5-Cl |
| A-1529 | 3,5-Dichlorophenyl | Allyl | 1 | 5-Cl |
| A-1530 | 2-Chloro-4-fluorophenyl | Allyl | 1 | 5-Cl |
| A-1531 | Pyridin-2-yl | Allyl | 1 | 5-Cl |
| A-1532 | Pyridin-4-yl | Allyl | 1 | 5-Cl |
| A-1533 | Thien-2-yl | Allyl | 1 | 5-Cl |
| A-1534 | 3-Trifluoromethylphenyl | Allyl | 1 | 5-Cl |
| A-1535 | 4-(Diethylamino-methyl)phenyl | Allyl | 1 | 5-Cl |
| A-1536 | 4-(Morpholin-4-ylmethyl)phenyl | Allyl | 1 | 5-Cl |
| A-1537 | 4-(Morpholin-4-yl)phenyl | Allyl | 1 | 5-Cl |
| A-1538 | Phenyl | Cyclopropyl | 1 | 5-Cl |
| A-1539 | 2-Methylphenyl | Cyclopropyl | 1 | 5-Cl |
| A-1540 | 2-Methoxyphenyl | Cyclopropyl | 1 | 5-Cl |
| A-1541 | 2-Chlorophenyl | Cyclopropyl | 1 | 5-Cl |
| A-1542 | 2-Fluorophenyl | Cyclopropyl | 1 | 5-Cl |
| A-1543 | 3-Methylphenyl | Cyclopropyl | 1 | 5-Cl |
| A-1544 | 3-Methoxyphenyl | Cyclopropyl | 1 | 5-Cl |
| A-1545 | 3-Chlorophenyl | Cyclopropyl | 1 | 5-Cl |
| A-1546 | 3-Fluorophenyl | Cyclopropyl | 1 | 5-Cl |
| A-1547 | 4-Methylphenyl | Cyclopropyl | 1 | 5-Cl |
| A-1548 | 4-Methoxyphenyl | Cyclopropyl | 1 | 5-Cl |
| A-1549 | 4-Chlorophenyl | Cyclopropyl | 1 | 5-Cl |
| A-1550 | 4-Fluorophenyl | Cyclopropyl | 1 | 5-Cl |
| A-1551 | 2,4-Difluorophenyl | Cyclopropyl | 1 | 5-Cl |
| A-1552 | 2,6-Difluorophenyl | Cyclopropyl | 1 | 5-Cl |
| A-1553 | 3,5-Difluorophenyl | Cyclopropyl | 1 | 5-Cl |
| A-1554 | 2,4-Dichlorophenyl | Cyclopropyl | 1 | 5-Cl |
| A-1555 | 2,6-Dichlorophenyl | Cyclopropyl | 1 | 5-Cl |
| A-1556 | 3,5-Dichlorophenyl | Cyclopropyl | 1 | 5-Cl |
| A-1557 | 2-Chloro-4-fluorophenyl | Cyclopropyl | 1 | 5-Cl |
| A-1558 | Pyridin-2-yl | Cyclopropyl | 1 | 5-Cl |
| A-1559 | Pyridin-4-yl | Cyclopropyl | 1 | 5-Cl |
| A-1560 | Thien-2-yl | Cyclopropyl | 1 | 5-Cl |
| A-1561 | 3-Trifluoromethylphenyl | Cyclopropyl | 1 | 5-Cl |
| A-1562 | 4-(Diethylamino-methyl)phenyl | Cyclopropyl | 1 | 5-Cl |
| A-1563 | 4-(Morpholin-4-ylmethyl)phenyl | Cyclopropyl | 1 | 5-Cl |
| A-1564 | 4-(Morpholin-4-yl)phenyl | Cyclopropyl | 1 | 5-Cl |
| A-1565 | Phenyl | Propyl | 1 | 5-Cl |
| A-1566 | 2-Methylphenyl | Propyl | 1 | 5-Cl |
| A-1567 | 2-Methoxyphenyl | Propyl | 1 | 5-Cl |
| A-1568 | 2-Chlorophenyl | Propyl | 1 | 5-Cl |
| A-1569 | 2-Fluorophenyl | Propyl | 1 | 5-Cl |
| A-1570 | 3-Methylphenyl | Propyl | 1 | 5-Cl |
| A-1571 | 3-Methoxyphenyl | Propyl | 1 | 5-Cl |
| A-1572 | 3-Chlorophenyl | Propyl | 1 | 5-Cl |
| A-1573 | 3-Fluorophenyl | Propyl | 1 | 5-Cl |
| A-1574 | 4-Methylphenyl | Propyl | 1 | 5-Cl |
| A-1575 | 4-Methoxyphenyl | Propyl | 1 | 5-Cl |
| A-1576 | 4-Chlorophenyl | Propyl | 1 | 5-Cl |
| A-1577 | 4-Fluorophenyl | Propyl | 1 | 5-Cl |
| A-1578 | 2,4-Difluorophenyl | Propyl | 1 | 5-Cl |
| A-1579 | 2,6-Difluorophenyl | Propyl | 1 | 5-Cl |
| A-1580 | 3,5-Difluorophenyl | Propyl | 1 | 5-Cl |
| A-1581 | 2,4-Dichlorophenyl | Propyl | 1 | 5-Cl |
| A-1582 | 2,6-Dichlorophenyl | Propyl | 1 | 5-Cl |
| A-1583 | 3,5-Dichlorophenyl | Propyl | 1 | 5-Cl |
| A-1584 | 2-Chloro-4-fluorophenyl | Propyl | 1 | 5-Cl |
| A-1585 | Pyridin-2-yl | Propyl | 1 | 5-Cl |
| A-1586 | Pyridin-4-yl | Propyl | 1 | 5-Cl |
| A-1587 | Thien-2-yl | Propyl | 1 | 5-Cl |
| A-1588 | 3-Trifluoromethylphenyl | Propyl | 1 | 5-Cl |
| A-1589 | 4-(Diethylamino-methyl)phenyl | Propyl | 1 | 5-Cl |
| A-1590 | 4-(Morpholin-4-ylmethyl)phenyl | Propyl | 1 | 5-Cl |
| A-1591 | 4-(Morpholin-4-yl)phenyl | Propyl | 1 | 5-Cl |
| A-1592 | Phenyl | Isopropyl | 1 | 5-Cl |
| A-1593 | 2-Methylphenyl | Isopropyl | 1 | 5-Cl |
| A-1594 | 2-Methoxyphenyl | Isopropyl | 1 | 5-Cl |
| A-1595 | 2-Chlorophenyl | Isopropyl | 1 | 5-Cl |
| A-1596 | 2-Fluorophenyl | Isopropyl | 1 | 5-Cl |
| A-1597 | 3-Methylphenyl | Isopropyl | 1 | 5-Cl |
| A-1598 | 3-Methoxyphenyl | Isopropyl | 1 | 5-Cl |
| A-1599 | 3-Chlorophenyl | Isopropyl | 1 | 5-Cl |
| A-1600 | 3-Fluorophenyl | Isopropyl | 1 | 5-Cl |
| A-1601 | 4-Methylphenyl | Isopropyl | 1 | 5-Cl |
| A-1602 | 4-Methoxyphenyl | Isopropyl | 1 | 5-Cl |
| A-1603 | 4-Chlorophenyl | Isopropyl | 1 | 5-Cl |
| A-1604 | 4-Fluorophenyl | Isopropyl | 1 | 5-Cl |
| A-1605 | 2,4-Difluorophenyl | Isopropyl | 1 | 5-Cl |
| A-1606 | 2,6-Difluorophenyl | Isopropyl | 1 | 5-Cl |
| A-1607 | 3,5-Difluorophenyl | Isopropyl | 1 | 5-Cl |
| A-1608 | 2,4-Dichlorophenyl | Isopropyl | 1 | 5-Cl |
| A-1609 | 2,6-Dichlorophenyl | Isopropyl | 1 | 5-Cl |
| A-1610 | 3,5-Dichlorophenyl | Isopropyl | 1 | 5-Cl |
| A-1611 | 2-Chloro-4-fluorophenyl | Isopropyl | 1 | 5-Cl |
| A-1612 | Pyridin-2-yl | Isopropyl | 1 | 5-Cl |
| A-1613 | Pyridin-4-yl | Isopropyl | 1 | 5-Cl |
| A-1614 | Thien-2-yl | Isopropyl | 1 | 5-Cl |
| A-1615 | 3-Trifluoromethylphenyl | Isopropyl | 1 | 5-Cl |
| A-1616 | 4-(Diethylamino-methyl)phenyl | Isopropyl | 1 | 5-Cl |
| A-1617 | 4-(Morpholin-4-ylmethyl)phenyl | Isopropyl | 1 | 5-Cl |
| A-1618 | 4-(Morpholin-4-yl)phenyl | Isopropyl | 1 | 5-Cl |
| A-1619 | Phenyl | Tert.butyl | 1 | 5-Cl |
| A-1620 | 2-Methylphenyl | Tert.butyl | 1 | 5-Cl |
| A-1621 | 2-Methoxyphenyl | Tert.butyl | 1 | 5-Cl |
| A-1622 | 2-Chlorophenyl | Tert.butyl | 1 | 5-Cl |
| A-1623 | 2-Fluorophenyl | Tert.butyl | 1 | 5-Cl |
| A-1624 | 3-Methylphenyl | Tert.butyl | 1 | 5-Cl |
| A-1625 | 3-Methoxyphenyl | Tert.butyl | 1 | 5-Cl |
| A-1626 | 3-Chlorophenyl | Tert.butyl | 1 | 5-Cl |
| A-1627 | 3-Fluorophenyl | Tert.butyl | 1 | 5-Cl |
| A-1628 | 4-Methylphenyl | Tert.butyl | 1 | 5-Cl |
| A-1629 | 4-Methoxyphenyl | Tert.butyl | 1 | 5-Cl |
| A-1630 | 4-Chlorophenyl | Tert.butyl | 1 | 5-Cl |
| A-1631 | 4-Fluorophenyl | Tert.butyl | 1 | 5-Cl |
| A-1632 | 2,4-Difluorophenyl | Tert.butyl | 1 | 5-Cl |

TABLE A-continued

| No. | R² | R³ | m | R⁵ |
|---|---|---|---|---|
| A-1633 | 2,6-Difluorophenyl | Tert.butyl | 1 | 5-Cl |
| A-1634 | 3,5-Difluorophenyl | Tert.butyl | 1 | 5-Cl |
| A-1635 | 2,4-Dichlorophenyl | Tert.butyl | 1 | 5-Cl |
| A-1636 | 2,6-Dichlorophenyl | Tert.butyl | 1 | 5-Cl |
| A-1637 | 3,5-Dichlorophenyl | Tert.butyl | 1 | 5-Cl |
| A-1638 | 2-Chloro-4-fluorophenyl | Tert.butyl | 1 | 5-Cl |
| A-1639 | Pyridin-2-yl | Tert.butyl | 1 | 5-Cl |
| A-1640 | Pyridin-4-yl | Tert.butyl | 1 | 5-Cl |
| A-1641 | Thien-2-yl | Tert.butyl | 1 | 5-Cl |
| A-1642 | 3-Trifluoromethylphenyl | Tert.butyl | 1 | 5-Cl |
| A-1643 | 4-(Diethylamino-methyl)phenyl | Tert.butyl | 1 | 5-Cl |
| A-1644 | 4-(Morpholin-4-ylmethyl)phenyl | Tert.butyl | 1 | 5-Cl |
| A-1645 | 4-(Morpholin-4-yl)phenyl | Tert.butyl | 1 | 5-Cl |
| A-1646 | Phenyl | Cyclobutyl | 1 | 5-Cl |
| A-1647 | 2-Methylphenyl | Cyclobutyl | 1 | 5-Cl |
| A-1648 | 2-Methoxyphenyl | Cyclobutyl | 1 | 5-Cl |
| A-1649 | 2-Chlorophenyl | Cyclobutyl | 1 | 5-Cl |
| A-1650 | 2-Fluorophenyl | Cyclobutyl | 1 | 5-Cl |
| A-1651 | 3-Methylphenyl | Cyclobutyl | 1 | 5-Cl |
| A-1652 | 3-Methoxyphenyl | Cyclobutyl | 1 | 5-Cl |
| A-1653 | 3-Chlorophenyl | Cyclobutyl | 1 | 5-Cl |
| A-1654 | 3-Fluorophenyl | Cyclobutyl | 1 | 5-Cl |
| A-1655 | 4-Methylphenyl | Cyclobutyl | 1 | 5-Cl |
| A-1656 | 4-Methoxyphenyl | Cyclobutyl | 1 | 5-Cl |
| A-1657 | 4-Chlorophenyl | Cyclobutyl | 1 | 5-Cl |
| A-1658 | 4-Fluorophenyl | Cyclobutyl | 1 | 5-Cl |
| A-1659 | 2,4-Difluorophenyl | Cyclobutyl | 1 | 5-Cl |
| A-1660 | 2,6-Difluorophenyl | Cyclobutyl | 1 | 5-Cl |
| A-1661 | 3,5-Difluorophenyl | Cyclobutyl | 1 | 5-Cl |
| A-1662 | 2,4-Dichlorophenyl | Cyclobutyl | 1 | 5-Cl |
| A-1663 | 2,6-Dichlorophenyl | Cyclobutyl | 1 | 5-Cl |
| A-1664 | 3,5-Dichlorophenyl | Cyclobutyl | 1 | 5-Cl |
| A-1665 | 2-Chloro-4-fluorophenyl | Cyclobutyl | 1 | 5-Cl |
| A-1666 | Pyridin-2-yl | Cyclobutyl | 1 | 5-Cl |
| A-1667 | Pyridin-4-yl | Cyclobutyl | 1 | 5-Cl |
| A-1668 | Thien-2-yl | Cyclobutyl | 1 | 5-Cl |
| A-1669 | 3-Trifluoromethylphenyl | Cyclobutyl | 1 | 5-Cl |
| A-1670 | 4-(Diethylamino-methyl)phenyl | Cyclobutyl | 1 | 5-Cl |
| A-1671 | 4-(Morpholin-4-ylmethyl)phenyl | Cyclobutyl | 1 | 5-Cl |
| A-1672 | 4-(Morpholin-4-yl)phenyl | Cyclobutyl | 1 | 5-Cl |
| A-1673 | Phenyl | Cyclopentyl | 1 | 5-Cl |
| A-1674 | 2-Methylphenyl | Cyclopentyl | 1 | 5-Cl |
| A-1675 | 2-Methoxyphenyl | Cyclopentyl | 1 | 5-Cl |
| A-1676 | 2-Chlorophenyl | Cyclopentyl | 1 | 5-Cl |
| A-1677 | 2-Fluorophenyl | Cyclopentyl | 1 | 5-Cl |
| A-1678 | 3-Methylphenyl | Cyclopentyl | 1 | 5-Cl |
| A-1679 | 3-Methoxyphenyl | Cyclopentyl | 1 | 5-Cl |
| A-1680 | 3-Chlorophenyl | Cyclopentyl | 1 | 5-Cl |
| A-1681 | 3-Fluorophenyl | Cyclopentyl | 1 | 5-Cl |
| A-1682 | 4-Methylphenyl | Cyclopentyl | 1 | 5-Cl |
| A-1683 | 4-Methoxyphenyl | Cyclopentyl | 1 | 5-Cl |
| A-1684 | 4-Chlorophenyl | Cyclopentyl | 1 | 5-Cl |
| A-1685 | 4-Fluorophenyl | Cyclopentyl | 1 | 5-Cl |
| A-1686 | 2,4-Difluorophenyl | Cyclopentyl | 1 | 5-Cl |
| A-1687 | 2,6-Difluorophenyl | Cyclopentyl | 1 | 5-Cl |
| A-1688 | 3,5-Difluorophenyl | Cyclopentyl | 1 | 5-Cl |
| A-1689 | 2,4-Dichlorophenyl | Cyclopentyl | 1 | 5-Cl |
| A-1690 | 2,6-Dichlorophenyl | Cyclopentyl | 1 | 5-Cl |
| A-1691 | 3,5-Dichlorophenyl | Cyclopentyl | 1 | 5-Cl |
| A-1692 | 2-Chloro-4-fluorophenyl | Cyclopentyl | 1 | 5-Cl |
| A-1693 | Pyridin-2-yl | Cyclopentyl | 1 | 5-Cl |
| A-1694 | Pyridin-4-yl | Cyclopentyl | 1 | 5-Cl |
| A-1695 | Thien-2-yl | Cyclopentyl | 1 | 5-Cl |
| A-1696 | 3-Trifluoromethylphenyl | Cyclopentyl | 1 | 5-Cl |
| A-1697 | 4-(Diethylamino-methyl)phenyl | Cyclopentyl | 1 | 5-Cl |
| A-1698 | 4-(Morpholin-4-ylmethyl)phenyl | Cyclopentyl | 1 | 5-Cl |
| A-1699 | 4-(Morpholin-4-yl)phenyl | Cyclopentyl | 1 | 5-Cl |
| A-1700 | Phenyl | Cyclopropylmethyl | 1 | 5-Cl |
| A-1701 | 2-Methylphenyl | Cyclopropylmethyl | 1 | 5-Cl |
| A-1702 | 2-Methoxyphenyl | Cyclopropylmethyl | 1 | 5-Cl |
| A-1703 | 2-Chlorophenyl | Cyclopropylmethyl | 1 | 5-Cl |
| A-1704 | 2-Fluorophenyl | Cyclopropylmethyl | 1 | 5-Cl |
| A-1705 | 3-Methylphenyl | Cyclopropylmethyl | 1 | 5-Cl |
| A-1706 | 3-Methoxyphenyl | Cyclopropylmethyl | 1 | 5-Cl |
| A-1707 | 3-Chlorophenyl | Cyclopropylmethyl | 1 | 5-Cl |
| A-1708 | 3-Fluorophenyl | Cyclopropylmethyl | 1 | 5-Cl |
| A-1709 | 4-Methylphenyl | Cyclopropylmethyl | 1 | 5-Cl |
| A-1710 | 4-Methoxyphenyl | Cyclopropylmethyl | 1 | 5-Cl |
| A-1711 | 4-Chlorophenyl | Cyclopropylmethyl | 1 | 5-Cl |
| A-1712 | 4-Fluorophenyl | Cyclopropylmethyl | 1 | 5-Cl |
| A-1713 | 2,4-Difluorophenyl | Cyclopropylmethyl | 1 | 5-Cl |
| A-1714 | 2,6-Difluorophenyl | Cyclopropylmethyl | 1 | 5-Cl |
| A-1715 | 3,5-Difluorophenyl | Cyclopropylmethyl | 1 | 5-Cl |
| A-1716 | 2,4-Dichlorophenyl | Cyclopropylmethyl | 1 | 5-Cl |
| A-1717 | 2,6-Dichlorophenyl | Cyclopropylmethyl | 1 | 5-Cl |
| A-1718 | 3,5-Dichlorophenyl | Cyclopropylmethyl | 1 | 5-Cl |
| A-1719 | 2-Chloro-4-fluorophenyl | Cyclopropylmethyl | 1 | 5-Cl |
| A-1720 | Pyridin-2-yl | Cyclopropylmethyl | 1 | 5-Cl |
| A-1721 | Pyridin-4-yl | Cyclopropylmethyl | 1 | 5-Cl |
| A-1722 | Thien-2-yl | Cyclopropylmethyl | 1 | 5-Cl |
| A-1723 | 3-Trifluoromethylphenyl | Cyclopropylmethyl | 1 | 5-Cl |
| A-1724 | 4-(Diethylamino-methyl)phenyl | Cyclopropylmethyl | 1 | 5-Cl |
| A-1725 | 4-(Morpholin-4-ylmethyl)phenyl | Cyclopropylmethyl | 1 | 5-Cl |
| A-1726 | 4-(Morpholin-4-yl)phenyl | Cyclopropylmethyl | 1 | 5-Cl |
| A-1727 | Phenyl | 2-(Morpholin-4-yl)ethyl | 1 | 5-Cl |
| A-1728 | 2-Methylphenyl | 2-(Morpholin-4-yl)ethyl | 1 | 5-Cl |
| A-1729 | 2-Methoxyphenyl | 2-(Morpholin-4-yl)ethyl | 1 | 5-Cl |
| A-1730 | 2-Chlorophenyl | 2-(Morpholin-4-yl)ethyl | 1 | 5-Cl |
| A-1731 | 2-Fluorophenyl | 2-(Morpholin-4-yl)ethyl | 1 | 5-Cl |
| A-1732 | 3-Methylphenyl | 2-(Morpholin-4-yl)ethyl | 1 | 5-Cl |
| A-1733 | 3-Methoxyphenyl | 2-(Morpholin-4-yl)ethyl | 1 | 5-Cl |
| A-1734 | 3-Chlorophenyl | 2-(Morpholin-4-yl)ethyl | 1 | 5-Cl |
| A-1735 | 3-Fluorophenyl | 2-(Morpholin-4-yl)ethyl | 1 | 5-Cl |
| A-1736 | 4-Methylphenyl | 2-(Morpholin-4-yl)ethyl | 1 | 5-Cl |
| A-1737 | 4-Methoxyphenyl | 2-(Morpholin-4-yl)ethyl | 1 | 5-Cl |
| A-1738 | 4-Chlorophenyl | 2-(Morpholin-4-yl)ethyl | 1 | 5-Cl |
| A-1739 | 4-Fluorophenyl | 2-(Morpholin-4-yl)ethyl | 1 | 5-Cl |
| A-1740 | 2,4-Difluorophenyl | 2-(Morpholin-4-yl)ethyl | 1 | 5-Cl |
| A-1741 | 2,6-Difluorophenyl | 2-(Morpholin-4-yl)ethyl | 1 | 5-Cl |
| A-1742 | 3,5-Difluorophenyl | 2-(Morpholin-4-yl)ethyl | 1 | 5-Cl |
| A-1743 | 2,4-Dichlorophenyl | 2-(Morpholin-4-yl)ethyl | 1 | 5-Cl |
| A-1744 | 2,6-Dichlorophenyl | 2-(Morpholin-4-yl)ethyl | 1 | 5-Cl |
| A-1745 | 3,5-Dichlorophenyl | 2-(Morpholin-4-yl)ethyl | 1 | 5-Cl |
| A-1746 | 2-Chloro-4-fluorophenyl | 2-(Morpholin-4-yl)ethyl | 1 | 5-Cl |
| A-1747 | Pyridin-2-yl | 2-(Morpholin-4-yl)ethyl | 1 | 5-Cl |
| A-1748 | Pyridin-4-yl | 2-(Morpholin-4-yl)ethyl | 1 | 5-Cl |
| A-1749 | Thien-2-yl | 2-(Morpholin-4-yl)ethyl | 1 | 5-Cl |
| A-1750 | 3-Trifluoromethylphenyl | 2-(Morpholin-4-yl)ethyl | 1 | 5-Cl |
| A-1751 | 4-(Diethylamino-methyl)phenyl | 2-(Morpholin-4-yl)ethyl | 1 | 5-Cl |
| A-1752 | 4-(Morpholin-4-ylmethyl)phenyl | 2-(Morpholin-4-yl)ethyl | 1 | 5-Cl |
| A-1753 | 4-(Morpholin-4-yl)phenyl | 2-(Morpholin-4-yl)ethyl | 1 | 5-Cl |
| A-1754 | Phenyl | Benzyl | 1 | 5-Cl |
| A-1755 | 2-Methylphenyl | Benzyl | 1 | 5-Cl |
| A-1756 | 2-Methoxyphenyl | Benzyl | 1 | 5-Cl |
| A-1757 | 2-Chlorophenyl | Benzyl | 1 | 5-Cl |
| A-1758 | 2-Fluorophenyl | Benzyl | 1 | 5-Cl |
| A-1759 | 3-Methylphenyl | Benzyl | 1 | 5-Cl |
| A-1760 | 3-Methoxyphenyl | Benzyl | 1 | 5-Cl |
| A-1761 | 3-Chlorophenyl | Benzyl | 1 | 5-Cl |
| A-1762 | 3-Fluorophenyl | Benzyl | 1 | 5-Cl |
| A-1763 | 4-Methylphenyl | Benzyl | 1 | 5-Cl |
| A-1764 | 4-Methoxyphenyl | Benzyl | 1 | 5-Cl |
| A-1765 | 4-Chlorophenyl | Benzyl | 1 | 5-Cl |
| A-1766 | 4-Fluorophenyl | Benzyl | 1 | 5-Cl |
| A-1767 | 2,4-Difluorophenyl | Benzyl | 1 | 5-Cl |
| A-1768 | 2,6-Difluorophenyl | Benzyl | 1 | 5-Cl |
| A-1769 | 3,5-Difluorophenyl | Benzyl | 1 | 5-Cl |
| A-1770 | 2,4-Dichlorophenyl | Benzyl | 1 | 5-Cl |
| A-1771 | 2,6-Dichlorophenyl | Benzyl | 1 | 5-Cl |
| A-1772 | 3,5-Dichlorophenyl | Benzyl | 1 | 5-Cl |
| A-1773 | 2-Chloro-4-fluorophenyl | Benzyl | 1 | 5-Cl |

TABLE A-continued

| No. | R² | R³ | m | R⁵ |
|---|---|---|---|---|
| A-1774 | Pyridin-2-yl | Benzyl | 1 | 5-Cl |
| A-1775 | Pyridin-4-yl | Benzyl | 1 | 5-Cl |
| A-1776 | Thien-2-yl | Benzyl | 1 | 5-Cl |
| A-1777 | 3-Trifluoromethylphenyl | Benzyl | 1 | 5-Cl |
| A-1778 | 4-(Diethylamino-methyl)phenyl | Benzyl | 1 | 5-Cl |
| A-1779 | 4-(Morpholin-4-ylmethyl)phenyl | Benzyl | 1 | 5-Cl |
| A-1780 | 4-(Morpholin-4-yl)phenyl | Benzyl | 1 | 5-Cl |
| A-1781 | Phenyl | Pyridin-2-yl-methyl | 1 | 5-Cl |
| A-1782 | 2-Methylphenyl | Pyridin-2-yl-methyl | 1 | 5-Cl |
| A-1783 | 2-Methoxyphenyl | Pyridin-2-yl-methyl | 1 | 5-Cl |
| A-1784 | 2-Chlorophenyl | Pyridin-2-yl-methyl | 1 | 5-Cl |
| A-1785 | 2-Fluorophenyl | Pyridin-2-yl-methyl | 1 | 5-Cl |
| A-1786 | 3-Methylphenyl | Pyridin-2-yl-methyl | 1 | 5-Cl |
| A-1787 | 3-Methoxyphenyl | Pyridin-2-yl-methyl | 1 | 5-Cl |
| A-1788 | 3-Chlorophenyl | Pyridin-2-yl-methyl | 1 | 5-Cl |
| A-1789 | 3-Fluorophenyl | Pyridin-2-yl-methyl | 1 | 5-Cl |
| A-1790 | 4-Methylphenyl | Pyridin-2-yl-methyl | 1 | 5-Cl |
| A-1791 | 4-Methoxyphenyl | Pyridin-2-yl-methyl | 1 | 5-Cl |
| A-1792 | 4-Chlorophenyl | Pyridin-2-yl-methyl | 1 | 5-Cl |
| A-1793 | 4-Fluorophenyl | Pyridin-2-yl-methyl | 1 | 5-Cl |
| A-1794 | 2,4-Difluorophenyl | Pyridin-2-yl-methyl | 1 | 5-Cl |
| A-1795 | 2,6-Difluorophenyl | Pyridin-2-yl-methyl | 1 | 5-Cl |
| A-1796 | 3,5-Difluorophenyl | Pyridin-2-yl-methyl | 1 | 5-Cl |
| A-1797 | 2,4-Dichlorophenyl | Pyridin-2-yl-methyl | 1 | 5-Cl |
| A-1798 | 2,6-Dichlorophenyl | Pyridin-2-yl-methyl | 1 | 5-Cl |
| A-1799 | 3,5-Dichlorophenyl | Pyridin-2-yl-methyl | 1 | 5-Cl |
| A-1800 | 2-Chloro-4-fluorophenyl | Pyridin-2-yl-methyl | 1 | 5-Cl |
| A-1801 | Pyridin-2-yl | Pyridin-2-yl-methyl | 1 | 5-Cl |
| A-1802 | Pyridin-4-yl | Pyridin-2-yl-methyl | 1 | 5-Cl |
| A-1803 | Thien-2-yl | Pyridin-2-yl-methyl | 1 | 5-Cl |
| A-1804 | 3-Trifluoromethylphenyl | Pyridin-2-yl-methyl | 1 | 5-Cl |
| A-1805 | 4-(Diethylamino-methyl)phenyl | Pyridin-2-yl-methyl | 1 | 5-Cl |
| A-1806 | 4-(Morpholin-4-ylmethyl)phenyl | Pyridin-2-yl-methyl | 1 | 5-Cl |
| A-1807 | 4-(Morpholin-4-yl)phenyl | Pyridin-2-yl-methyl | 1 | 5-Cl |
| A-1808 | Cyclopropyl | Methyl | 1 | 5-Cl |
| A-1809 | Cyclopropyl | Ethyl | 1 | 5-Cl |
| A-1810 | Cyclopropyl | Allyl | 1 | 5-Cl |
| A-1811 | Cyclopropyl | Cyclopropyl | 1 | 5-Cl |
| A-1812 | Cyclopropyl | Propyl | 1 | 5-Cl |
| A-1813 | Cyclopropyl | Isopropyl | 1 | 5-Cl |
| A-1814 | Cyclopropyl | Tert.-Butyl | 1 | 5-Cl |
| A-1815 | Cyclopropyl | Cyclobutyl | 1 | 5-Cl |
| A-1816 | Cyclopropyl | Cyclopentyl | 1 | 5-Cl |
| A-1817 | Cyclopropyl | Cyclopropylmethyl | 1 | 5-Cl |
| A-1818 | Cyclopropyl | 2-(Morpholin-4-yl)ethyl | 1 | 5-Cl |
| A-1819 | Cyclopropyl | Benzyl | 1 | 5-Cl |
| A-1820 | Cyclopropyl | Pyridin-2-yl-methyl | 1 | 5-Cl |

The invention in particular relates to the compounds of formula I which are selected from the group consisting of 2-[3-(4-Fluorophenyl)-1H-pyrazol-1-yl]-N-[4-(methoxyamino)-3,4-dioxo-1-phenylbutan-2-yl]pyridine-3-carboxamide, (2R)-2-[3-(4-Fluorophenyl)-1H-pyrazol-1-yl]-N-[4-(methoxyamino)-3,4-dioxo-1-phenylbutan-2-yl]pyridine-3-carboxamide, (2S)-2-[3-(4-Fluorophenyl)-1H-pyrazol-1-yl]-N-[4-(methoxyamino)-3,4-dioxo-1-phenylbutan-2-yl]pyridine-3-carboxamide, N-(4-(Methoxyamino)-3,4-dioxo-1-phenylbutan-2-yl)-2-(3-phenyl-1H-pyrazol-1-yl)nicotinamide, (2R)—N-(4-(Methoxyamino)-3,4-dioxo-1-phenylbutan-2-yl)-2-(3-phenyl-1H-pyrazol-1-yl)nicotinamide, (2S)—N-(4-(Methoxyamino)-3,4-dioxo-1-phenylbutan-2-yl)-2-(3-phenyl-1H-pyrazol-1-yl)nicotinamide, 2-(4-Fluoro-3-phenyl-1H-pyrazol-1-yl)-N-(4-(methoxyamino)-3,4-dioxo-1-phenylbutan-2-yl)nicotinamide, (2R)-2-(4-Fluoro-3-phenyl-1H-pyrazol-1-yl)-N-(4-(methoxyamino)-3,4-dioxo-1-phenylbutan-2-yl)nicotinamide, (2S)-2-(4-Fluoro-3-phenyl-1H-pyrazol-1-yl)-N-(4-(methoxyamino)-3,4-dioxo-1-phenylbutan-2-yl)nicotinamide, N-[4-(Methoxyamino)-3,4-dioxo-1-phenylbutan-2-yl]-2-(4-methyl-3-phenyl-1H-pyrazol-1-yl)pyridine-3-carboxamide, (2R)—N-[4-(Methoxyamino)-3,4-dioxo-1-phenylbutan-2-yl]-2-(4-methyl-3-phenyl-1H-pyrazol-1-yl)pyridine-3-carboxamide, (2S)—N-[4-(Methoxyamino)-3,4-dioxo-1-phenylbutan-2-yl]-2-(4-methyl-3-phenyl-1H-pyrazol-1-yl)pyridine-3-carboxamide, N-(1-(4-Fluorophenyl)-4-(methoxyamino)-3,4-dioxo-butan-2-yl)-2-(3-phenyl-1H-pyrazol-1-yl)nicotinamide, (2R)—N-(1-(4-Fluorophenyl)-4-(methoxyamino)-3,4-dioxo-butan-2-yl)-2-(3-phenyl-1H-pyrazol-1-yl)nicotinamide, (2S)—N-(1-(4-Fluorophenyl)-4-(methoxyamino)-3,4-dioxo-butan-2-yl)-2-(3-phenyl-1H-pyrazol-1-yl)nicotinamide, N-(1-(3-Fluorophenyl)-4-(methoxyamino)-3,4-dioxobutan-2-yl)-2-(3-phenyl-1H-pyrazol-1-yl)nicotinamide, (2R)—N-(1-(3-Fluorophenyl)-4-(methoxyamino)-3,4-dioxobutan-2-yl)-2-(3-phenyl-1H-pyrazol-1-yl)nicotinamide, (2S)—N-(1-(3-Fluorophenyl)-4-(methoxyamino)-3,4-dioxobutan-2-yl)-2-(3-phenyl-1H-pyrazol-1-yl)nicotinamide, N-(4-(Ethoxyamino)-3,4-dioxo-1-phenylbutan-2-yl)-2-(3-phenyl-1H-pyrazol-1-yl)nicotinamide, (2R)—N-(4-(Ethoxyamino)-3,4-dioxo-1-phenylbutan-2-yl)-2-(3-phenyl-1H-pyrazol-1-yl)nicotinamide, (2S)—N-(4-(Ethoxyamino)-3,4-dioxo-1-phenylbutan-2-yl)-2-(3-phenyl-1H-pyrazol-1-yl)nicotinamide, N-(4-(Allyloxyamino)-3,4-dioxo-1-phenylbutan-2-yl)-2-(3-phenyl-1H-pyrazol-1-yl)nicotinamide, (2R)—N-(4-(Allyloxyamino)-3,4-dioxo-1-phenylbutan-2-yl)-2-(3-phenyl-1H-pyrazol-1-yl)nicotinamide, (2S)—N-(4-(Allyloxyamino)-3,4-dioxo-1-phenylbutan-2-yl)-2-(3-phenyl-1H-pyrazol-1-yl)nicotinamide, N-(4-(Methoxyamino)-1-(4-methoxyphenyl)-3,4-dioxo-butan-2-yl)-2-(3-phenyl-1H-pyrazol-1-yl)nicotinamide, (2R)—N-(4-(Methoxyamino)-1-(4-methoxyphenyl)-3,4-dioxo-butan-2-yl)-2-(3-phenyl-1H-pyrazol-1-yl)nicotinamide, (2S)—N-(4-(Methoxyamino)-1-(4-methoxyphenyl)-3,4-dioxo-butan-2-yl)-2-(3-phenyl-1H-pyrazol-1-yl)nicotinamide, 2-(4-Chloro-3-phenyl-1H-pyrazol-1-yl)-N-(4-(methoxyamino)-3,4-dioxo-1-phenylbutan-2-yl)nicotinamide, (2R)-2-(4-Chloro-3-phenyl-1H-pyrazol-1-yl)-N-(4-(methoxyamino)-3,4-dioxo-1-phenylbutan-2-yl)nicotinamide, (2S)-2-(4-Chloro-3-phenyl-1H-pyrazol-1-yl)-N-(4-(methoxyamino)-3,4-dioxo-1-phenylbutan-2-yl)nicotinamide, N-[4-(Isopropoxyamino)-3,4-dioxo-1-phenyl-2-butanyl]-2-(3-phenyl-1H-pyrazol-1-yl)nicotinamide, (2R)—N-[4-(Isopropoxyamino)-3,4-dioxo-1-phenyl-2-butanyl]-2-(3-phenyl-1H-pyrazol-1-yl)nicotinamide, (2S)—N-[4-(Isopropoxyamino)-3,4-dioxo-1-phenyl-2-butanyl]-2-(3-phenyl-1H-pyrazol-1-yl)nicotinamide, N-[3,4-Dioxo-1-phenyl-4-(propoxyamino)-2-butanyl]-2-(3-phenyl-1H-pyrazol-1-yl)nicotinamide, (2R)—N-[3,4-Dioxo-1-phenyl-4-(propoxyamino)-2-butanyl]-2-(3-phenyl-1H-pyrazol-1-yl)nicotinamide, (2S)—N-[3,4-Dioxo-1-phenyl-4-(propoxyamino)-2-butanyl]-2-(3-phenyl-1H-pyrazol-1-yl)nicotinamide, N-[4-(Methoxyamino)-3,4-dioxo-1-phenyl-2-butanyl]-2-{3-[4-(4-morpholinyl)phenyl]-1H-pyrazol-1-yl}nicotinamide,
(2R)—N-[4-(Methoxyamino)-3,4-dioxo-1-phenyl-2-butanyl]-2-{3-[4-(4-morpholinyl)phenyl]-1H-pyrazol-1-yl}nicotinamide,
(2S)—N-[4-(Methoxyamino)-3,4-dioxo-1-phenyl-2-butanyl]-2-{3-[4-(4-morpholinyl)phenyl]-1H-pyrazol-1-yl}nicotinamide,
N-[4-(Methoxyamino)-3,4-dioxo-1-phenyl-2-butanyl]-2-{3-[4-(4-morpholinylmethyl)phenyl]-1H-pyrazol-1-yl}nicotinamide,
(2R)—N-[4-(Methoxyamino)-3,4-dioxo-1-phenyl-2-butanyl]-2-{3-[4-(4-morpholinylmethyl)phenyl]-1H-pyrazol-1-yl}nicotinamide,
(2S)—N-[4-(Methoxyamino)-3,4-dioxo-1-phenyl-2-butanyl]-2-{3-[4-(4-morpholinylmethyl)phenyl]-1H-pyrazol-1-yl}nicotinamide,
2-(3-{4-[(Diethylamino)methyl]phenyl}-1H-pyrazol-1-yl)-N-[4-(methoxyamino)-3,4-dioxo-1-phenyl-2-butanyl]nicotinamide,
(2R)-2-(3-{4-[(Diethylamino)methyl]phenyl}-1H-pyrazol-1-yl)-N-[4-(methoxyamino)-3,4-dioxo-1-phenyl-2-butanyl]nicotinamide,
(2S)-2-(3-{4-[(Diethylamino)methyl]phenyl}-1H-pyrazol-1-yl)-N-[4-(methoxyamino)-3,4-dioxo-1-phenyl-2-butanyl]nicotinamide,
N-(4-{[(2-Methyl-2-propanyl)oxy]amino}-3,4-dioxo-1-phenyl-2-butanyl)-2-(3-phenyl-1H-pyrazol-1-yl)nicotinamide,
(2R)—N-(4-{[(2-Methyl-2-propanyl)oxy]amino}-3,4-dioxo-1-phenyl-2-butanyl)-2-(3-phenyl-1H-pyrazol-1-yl)nicotinamide,
(2S)—N-(4-{[(2-Methyl-2-propanyl)oxy]amino}-3,4-dioxo-1-phenyl-2-butanyl)-2-(3-phenyl-1H-pyrazol-1-yl)nicotinamide,
N-{4-[(Cyclopentyloxy)amino]-3,4-dioxo-1-phenyl-2-butanyl}-2-(3-phenyl-1H-pyrazol-1-yl)nicotinamide,
(2R)—N-{4-[(Cyclopentyloxy)amino]-3,4-dioxo-1-phenyl-2-butanyl}-2-(3-phenyl-1H-pyrazol-1-yl)nicotinamide,
(2S)—N-{4-[(Cyclopentyloxy)amino]-3,4-dioxo-1-phenyl-2-butanyl}-2-(3-phenyl-1H-pyrazol-1-yl)nicotinamide,
N-[4-(Ethoxyamino)-1-(4-fluorophenyl)-3,4-dioxo-2-butanyl]-2-(3-phenyl-1H-pyrazol-1-yl)nicotinamide,
(2R)—N-[4-(Ethoxyamino)-1-(4-fluorophenyl)-3,4-dioxo-2-butanyl]-2-(3-phenyl-1H-pyrazol-1-yl)nicotinamide,
(2S)—N-[4-(Ethoxyamino)-1-(4-fluorophenyl)-3,4-dioxo-2-butanyl]-2-(3-phenyl-1H-pyrazol-1-yl)nicotinamide,
N-[4-(Ethoxyamino)-3,4-dioxo-1-phenyl-2-butanyl]-2-(4-fluoro-3-phenyl-1H-pyrazol-1-yl)nicotinamide,
(2R)—N-[4-(Ethoxyamino)-3,4-dioxo-1-phenyl-2-butanyl]-2-(4-fluoro-3-phenyl-1H-pyrazol-1-yl)nicotinamide,
(2S)—N-[4-(Ethoxyamino)-3,4-dioxo-1-phenyl-2-butanyl]-2-(4-fluoro-3-phenyl-1H-pyrazol-1-yl)nicotinamide,
N-{4-[(Cyclobutyloxy)amino]-3,4-dioxo-1-phenyl-2-butanyl}-2-(3-phenyl-1H-pyrazol-1-yl)nicotinamide,
(2R)—N-{4-[(Cyclobutyloxy)amino]-3,4-dioxo-1-phenyl-2-butanyl}-2-(3-phenyl-1H-pyrazol-1-yl)nicotinamide,
(2S)—N-{4-[(Cyclobutyloxy)amino]-3,4-dioxo-1-phenyl-2-butanyl}-2-(3-phenyl-1H-pyrazol-1-yl)nicotinamide,
N-{4-[(2,2-Dimethylpropoxy)amino]-3,4-dioxo-1-phenyl-2-butanyl}-2-(3-phenyl-1H-pyrazol-1-yl)nicotinamide,
(2R)—N-{4-[(2,2-Dimethylpropoxy)amino]-3,4-dioxo-1-phenyl-2-butanyl}-2-(3-phenyl-1H-pyrazol-1-yl)nicotinamide,
(2S)—N-{4-[(2,2-Dimethylpropoxy)amino]-3,4-dioxo-1-phenyl-2-butanyl}-2-(3-phenyl-1H-pyrazol-1-yl)nicotinamide,
N-(4-{[2-(4-Morpholinyl)ethoxy]amino}-3,4-dioxo-1-phenyl-2-butanyl)-2-(3-phenyl-1H-pyrazol-1-yl)nicotinamide,
(2R)—N-(4-{[2-(4-Morpholinyl)ethoxy]amino}-3,4-dioxo-1-phenyl-2-butanyl)-2-(3-phenyl-1H-pyrazol-1-yl)nicotinamide,
(2S)—N-(4-{[2-(4-Morpholinyl)ethoxy]amino}-3,4-dioxo-1-phenyl-2-butanyl)-2-(3-phenyl-1H-pyrazol-1-yl)nicotinamide,
N-{4-[(Cyclopropylmethoxy)amino]-3,4-dioxo-1-phenyl-2-butanyl}-2-(3-phenyl-1H-pyrazol-1-yl)nicotinamide,
(2R)—N-{4-[(Cyclopropylmethoxy)amino]-3,4-dioxo-1-phenyl-2-butanyl}-2-(3-phenyl-1H-pyrazol-1-yl)nicotinamide,
(2S)—N-{4-[(Cyclopropylmethoxy)amino]-3,4-dioxo-1-phenyl-2-butanyl}-2-(3-phenyl-1H-pyrazol-1-yl)nicotinamide,
N-[4-(Ethoxyamino)-1-(4-methoxyphenyl)-3,4-dioxo-2-butanyl]-2-(3-phenyl-1H-pyrazol-1-yl)nicotinamid
(2R)—N-[4-(Ethoxyamino)-1-(4-methoxyphenyl)-3,4-dioxo-2-butanyl]-2-(3-phenyl-1H-pyrazol-1-yl)nicotinamid
(2S)—N-[4-(Ethoxyamino)-1-(4-methoxyphenyl)-3,4-dioxo-2-butanyl]-2-(3-phenyl-1H-pyrazol-1-yl)nicotinamid
2-[3-(2-Fluorophenyl)-1H-pyrazol-1-yl]-N-[4-(methoxyamino)-3,4-dioxo-1-phenyl-2-butanyl]nicotinamide,
(2R)-2-[3-(2-Fluorophenyl)-1H-pyrazol-1-yl]-N-[4-(methoxyamino)-3,4-dioxo-1-phenyl-2-butanyl]nicotinamide,
(2S)-2-[3-(2-Fluorophenyl)-1H-pyrazol-1-yl]-N-[4-(methoxyamino)-3,4-dioxo-1-phenyl-2-butanyl]nicotinamide,
N-[4-(Methoxyamino)-3,4-dioxo-1-phenyl-2-butanyl]-2-{3-[3-(trifluoromethyl)phenyl]-1H-pyrazol-1-yl}nicotinamide,
(2R)—N-[4-(Methoxyamino)-3,4-dioxo-1-phenyl-2-butanyl]-2-{3-[3-(trifluoromethyl)phenyl]-1H-pyrazol-1-yl}nicotinamide,
(2S)—N-[4-(Methoxyamino)-3,4-dioxo-1-phenyl-2-butanyl]-2-{3-[3-(trifluoromethyl)phenyl]-1H-pyrazol-1-yl}nicotinamide,
N-[4-(Methoxyamino)-3,4-dioxo-1-phenyl-2-butanyl]-2-[3-(2-pyridinyl)-1H-pyrazol-1-yl]nicotinamide,
(2R)—N-[4-(Methoxyamino)-3,4-dioxo-1-phenyl-2-butanyl]-2-[3-(2-pyridinyl)-1H-pyrazol-1-yl]nicotinamide,
(2S)—N-[4-(Methoxyamino)-3,4-dioxo-1-phenyl-2-butanyl]-2-[3-(2-pyridinyl)-1H-pyrazol-1-yl]nicotinamide,
N-(3,4-Dioxo-1-phenyl-4-(thiazol-2-ylamino)butan-2-yl)-2-(3-phenyl-1H-pyrazol-1-yl)nicotinamide,
(2R)—N-(3,4-Dioxo-1-phenyl-4-(thiazol-2-ylamino)butan-2-yl)-2-(3-phenyl-1H-pyrazol-1-yl)nicotinamide,
(2S)—N-(3,4-Dioxo-1-phenyl-4-(thiazol-2-ylamino)butan-2-yl)-2-(3-phenyl-1H-pyrazol-1-yl)nicotinamide,
the tautomers thereof, the hydrates thereof, the prodrugs thereof and the pharmaceutically suitable salts thereof.

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", $5^{th}$ edition, Wiley & Sons and the literature cited therein, and R. Larock, "Comprehensive Organic Transformations", $2^{nd}$ edition, Weinheim, 1999 and the literature cited therein. The carboxamide compounds of the invention of the general formula I are advantageously prepared by the methods described below and/or in the experimental section.

The compounds of the formula I can be prepared in analogy to the schemes and methods described in WO 99/54305, pp. 6-10 and in WO 2008/080969, pp. 65-70. An important access to compounds of the formula I is depicted in scheme 1.

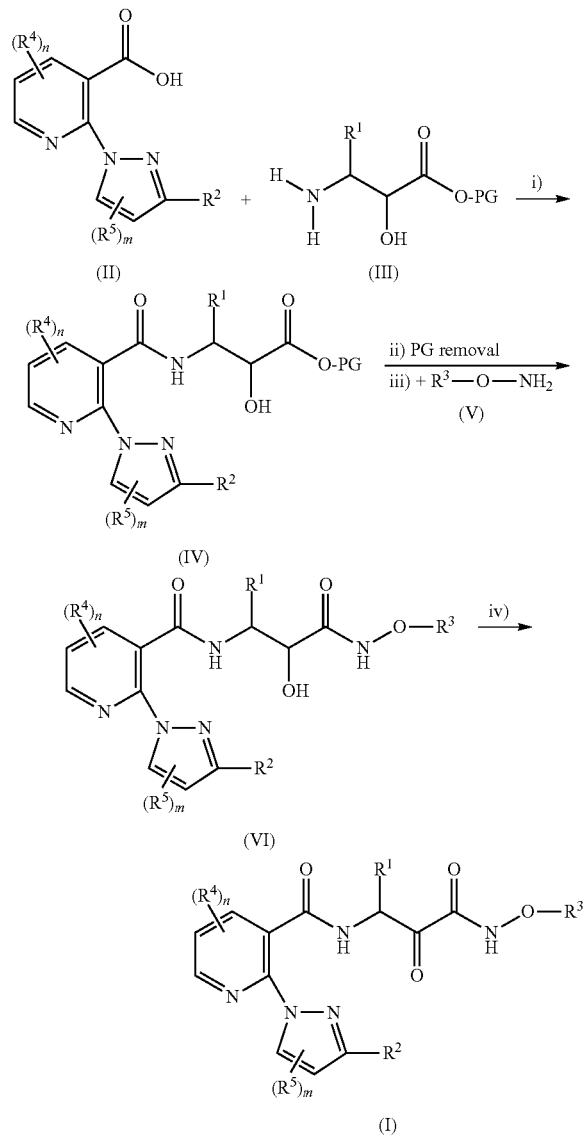

Scheme 1:

In scheme 1, $R^1$, $R^2$, $R^3$, $R^4$, $R^5$, m and n exhibit the aforementioned meanings and the variable PG is a protective group, which may be any protective group known in the art to be suitable for blocking carboxylic acid groups and is preferably selected from $C_1$-$C_6$-alkyls, in particular methyl and ethyl.

In a first step i), a carboxylic acid II is converted by reaction with an amino hydroxy ester III into a corresponding hydroxy amido ester IV. In this connection, conventional peptide coupling methods are ordinarily used, as are described for example in R. C. Larock, Comprehensive Organic Transformations, VCH Publisher, 1989, pages 972-976, or in Houben-Weyl, Methoden der organischen Chemie, 4$^{th}$ edition, E5, Chap. V. It may be advantageous firstly to activate the carboxylic acid II. For this purpose, for example, the carboxylic acid II is reacted with a coupling agent, e.g. a carbodiimide such as dicyclohexylcarbodiimide (DCC), CDI (carbonyldiimidazole), carbonyldipyrazole, DCI (diisopropylcarbodiimide) or 1-ethyl-3-(3-dimethylaminopropyl)carbodiimide (EDC) preferably in the presence of hydroxybenzotriazole (HOBt), nitrophenol, pentafluorophenol, 2,4,5-trichlorophenol or N-hydroxysuccinimide, to obtain an activated ester IL. It may further be advantageous to prepare the activated ester IL in the presence of a base, for example a tertiary amine. Further suitable coupling agents for step I are those mentioned for step iii) below, such as benzotriazole derivatives, pyridinotriazole derivatives and phosphonium activators. The activated ester IIa is subsequently reacted with the amino hydroxy ester of the formula III or its hydrohalide salt to give the hydroxy amide ester IV. The reaction normally takes place in anhydrous inert solvents such as chlorinated hydrocarbons, e.g. dichloromethane or dichloroethane, ethers, e.g. tetrahydrofuran or 1,4-dioxane or carboxamides, e.g. N,N-dimethylformamide, N,N-dimethylacetamide or N-methylpyrrolidone. Step i) is ordinarily carried out at temperatures in the range from $-20°$ C. to $+25°$ C.

In subsequent step ii) the protective group PG is removed using customary methods. In case PG is an alkyl group the reaction is preferably carried out by treating compound IV with a base in an aqueous medium, for example lithium hydroxide in a tetrahydrofuran (THF)/water mixture. The resulting carboxylic acid is coupled in the following step iii) with the hydroxylamine V to the hydroxy diamide VI employing a coupling method analogous to those described above for step i). Suitable coupling reagents (activators) are known to those skilled in the art and are selected, for example, from carbodiimides such as DCC, EDC, CDI (carbonyldiimidazole), carbonyldipyrazole and DCI (diisopropylcarbodiimide), benzotriazole derivatives such as 1-hydroxybenzotriazole, HBTU ((O-benzotriazol-1-yl)-N,N,N',N'-tetramethyluronium hexafluorophosphate) and HCTU (1-[bis(dimethylamino)methylene]-5-chloro-1H-benzotriazolium tetrafluoroborate), pyridinotriazole derivatives such as HATU (2-(7-aza-1H-benzotriazol-1-yl)-1,1,3,3-tetramethyluronium hexafluorophosphate), and phosphonium activators such as BOP ((benzotriazol-1-yloxy)tris(dimethylamino)phosphonium hexafluorophosphate), Py-BOP ((benzotriazol-1-yloxy)tripyrrolidinephosphonium hexafluorophosphate) and Py-BrOP (bromotripyrrolidine-phosphonium hexafluorophosphate). In general, the activator is used in excess. The benzotriazole and phosphonium coupling reagents are generally used in a basic medium, e.g. in the presence of an amine different from V, preferably a non-nucleophilic amine, such as tertiary aliphatic amines, in particular diisopropylethylamine, and alicyclic amines. The reaction conditions usually correspond to those given above for step i).

In the subsequent step iv), the hydroxy diamide compound VI is oxidized to the carboxamide compound I of the invention. Various conventional oxidation reactions are suitable for this (see R. C. Larock, Comprehensive Organic Transformations, VCH Publisher, 1989, page 604 et seq.) such as, for example, swern oxidation and swern analogous oxidations (T. T. Tidwell, Synthesis 1990, pp. 857-870) or Pfitzner-Moffatt oxidation. Suitable oxidizing agents are dimethyl sulfoxide (DMSO) in combination with dicyclohexylcarbodiimide or 1-ethyl-3-(3-dimethylaminopropyl)carbodiimide, dimethyl sulfoxide in combination with the pyridine-$SO_3$ complex or dimethyl sulfoxide in combination with oxalyl chloride, sodium hypochloride/TEMPO (S. L. Harbenson et al., J. Med. Chem. 1994, 37, 2918-2929) or hypervalent iodine compounds (periodinane), such as 2-iodoxybenzoic acid (IBX) (J. Org. Chem. 1995, 60, 7272) or the Dess-Martin periodinane (J. Org. Chem. 1983, 48, 4155). Depending on the oxidizing agent used, the oxidation of the hydroxy diamide compound VI takes place at temperatures of from $-50$ to $+35°$ C.

The hydroxylamines V and the amino hydroxy esters III are either commercially available or can be prepared according to established processes.

The deuterated derivatives I-D of compounds I that have a S-configuration at the carbon atom carrying both the deuterium and the radical $R^1$, are accessible via the process depicted in scheme 1 by starting from the corresponding deuterated intermediates III'. The compounds III' can be synthesized by an apparent variant of a 9-step process described by F. Maltais et al., J. Med. Chem. 2009, 52 (24), 7993-8001 (DOI 10.1021/jm901023f), as shown below. This process starts form alkynol VII and includes a chiral resolution of the intermediately obtained racemic mixture via amidation with deoxycholic acid.

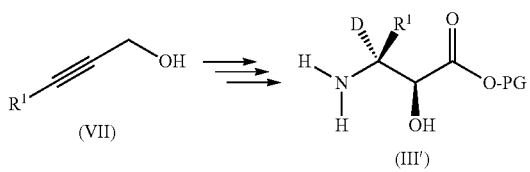

The carboxylic acid II can be prepared by hydrolyzing the carboxylic ester VIII with acids or bases under generally customary conditions. The hydrolysis preferably takes place with bases such as alkali metal or alkaline earth metal hydroxides, for example lithium hydroxide, sodium hydroxide or potassium hydroxide in aqueous medium, such as a mixture of water and organic solvents, e.g. alcohols such as methanol or ethanol, ethers such as tetrahydrofuran or dioxane, at room temperature or elevated temperature such as 25-100° C.

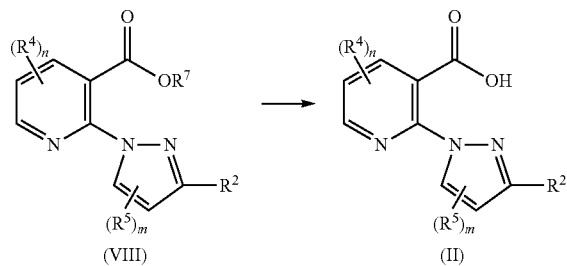

In formulae II and VIII, $R^2$, $R^4$, $R^5$, m and n have the aforementioned meanings. In formula VIII, $R^7$ is alkyl, preferably $C_1$-$C_6$-alkyl.

The carboxylic ester of the formula VIII can advantageously be obtained by reacting the carboxylic ester of the general formula IX with a pyrazole compound X, as shown in scheme 3.

Scheme 3:

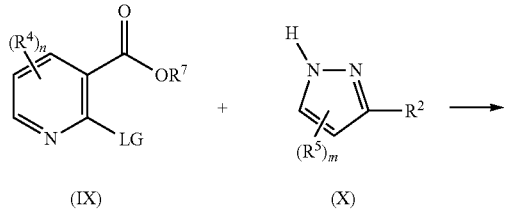

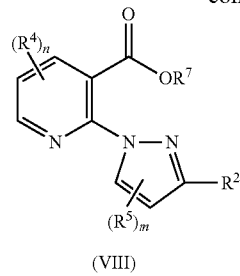

In scheme 3, LG represents a nucleophilically displaceable leaving group. Examples of suitable nucleophilically displaceable leaving groups are halogen, e.g. chlorine or bromine, or tosylate. $R^7$ is alkyl, preferably $C_1$-$C_6$-alkyl. $R^2$, $R^4$, $R^5$, m and n have the aforementioned meanings.

As shown in scheme 3, an ester IX is reacted with an appropriate pyrazole compound of the formula X. The reaction is ordinarily carried out under conventional conditions in the presence of a base in an inert solvent at elevated temperature. It may be advantageous where appropriate to carry out the reaction in the presence of catalytically active amounts of a transition metal, in particular of a metal of group 10 or 11 in the periodic table.

The reaction is preferably carried out at elevated temperature without diluent or in an inert solvent such as an ether, e.g. tetrahydrofuran or dioxane, carboxamides such as N,N-dimethylformamide, N,N-dimethylacetamide or N-methylpyrrolidone, or an aromatic hydrocarbon such as benzene, toluene or o-, m- or p-xylene. The reaction takes place in the presence of inorganic or organic bases and of a crown ether. Suitable inorganic bases are alkali metal or alkaline earth metal amides such as sodium amide, alkali metal or alkaline earth metal carbonates such as potassium carbonate or cesium carbonate or alkali metal hydrides such as sodium hydride. Suitable organic bases are tertiary amines, such as, for example, trimethylamine or triethylamine. A suitable crown ether is 18-crown-6. A Cu(I) salt such as, for example, CuI, CuCN, $Cu_2O$ is added where appropriate as catalyst (see, for example, U.S. Pat. No. 4,826,835 and WO 88/00468).

The pyrazole compounds X can be purchased or can be prepared by conventional methods, which are briefly outlined below, from precursors which can be obtained by purchase.

General methods for preparing pyrazoles of the general formula X are described for example in R. Fusco in "The Chemistry of Heterocyclic Compounds: Pyrazoles, Pyrazolines, Pyrazolidines, Indazoles and Condensed Rings", Wiley, R. H., editor; Wiley: New York, 1967; Vol. 22, pages 1-174; or J. Elguero, in "Comprehensive Heterocyclic Chemistry"; Potts, K. T., Ed.; Pergamon: Oxford 1984; Vol. 5, pages 291-298. One of the most commonly used methods is cyclocondensation of 1,3-dicarbonyl compounds or correspondingly reactive analogs with hydrazine or substituted hydrazine derivatives.

3-Aryl- or 3-hetaryl-substituted pyrazoles X are particularly advantageously prepared by reacting 1-aryl- or 1-hetaryl-3-dimethylamino-2-propene compounds with hydrazine in analogy to the processes described for example in M. A. Halcrow et al.; J. Chem. Soc. Dalton Trans. 1997, pages 4025-4035. The 1-aryl- or 1-hetaryl-3-dimethylamino-2-propenes required as starting material can easily be prepared by condensing the analogous aromatic acetyl compounds with N,N-dimethylformamide dimethyl acetal (or analogously using the corresponding diethyl acetal). The reaction is normally carried out without diluent or in an inert solvent such as, for example, dimethylformamide or toluene, at elevated temperature. It is particularly advantageous to introduce the activation energy necessary for the reaction into the reaction mixture also by means of microwaves and to carry out the reaction under elevated pressure as described in A. K. Pleier, Synthesis 2001, 1, 55-62.

A further general possibility for preparing substituted pyrazoles of the formula X is the Suzuki coupling of appropriate pyrazoleboronic acids or pyrazoleboronic esters as described for example in: N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253. An appropriate alternative is also Stille coupling of halogenated pyrazole derivatives with appropriate tin organyls as described for example by J. Eluguero et al.; Synthesis 1997, 5, 563-566.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

If individual compounds I are not obtainable by the routes described above, they can be prepared by derivatization of other compounds I.

The compounds of the invention exhibit extremely low Ki values in relation to the inhibition of calpain and thus permit efficient inhibition of calpain, especially calpain I, at low serum levels. The compounds of the invention ordinarily exhibit Ki values in relation to the inhibition of calpain in vitro of <1200 nM, preferably <600 nM, in particular <300 nM and specifically ≤200 nM. The compounds of the invention are therefore particularly suitable for the treatment of disorders associated with an elevated calpain activity.

In addition, the compounds of the invention are selective calpain inhibitors, i.e. the inhibition of other cysteine proteases such as cathepsin B, cathepsin K, cathepsin L or cathepsin S takes place only at concentrations which are distinctly higher than the concentrations necessary for inhibition of calpain. Accordingly, the compounds of the invention ought to show distinctly fewer side effects than the prior art compounds which are comparatively unselective in relation to inhibition of calpain and likewise inhibit other cysteine proteases.

Compounds preferred according to the invention accordingly have a selectivity in relation to inhibition of cathepsin B, expressed in the form of the ratio of the Ki for inhibition of cathepsin B to the Ki for inhibition of calpain of ≥2, in particular ≥4 and specifically ≥10.

Compounds preferred according to the invention accordingly have a selectivity in relation to inhibition of cathepsin K, expressed in the form of the ratio of the Ki for inhibition of cathepsin K to the Ki for inhibition of calpain of ≥2, in particular ≥4 and specifically ≥10.

Compounds preferred according to the invention accordingly have a selectivity in relation to inhibition of cathepsin L, expressed in the form of the ratio of the Ki for inhibition of cathepsin L to the Ki for inhibition of calpain of ≥5, in particular ≥10 and specifically ≥50.

Compounds preferred according to the invention accordingly have a selectivity in relation to inhibition of cathepsin S, expressed in the form of the ratio of the Ki for inhibition of cathepsin S to the Ki for inhibition of calpain of ≥5, in particular ≥10 and specifically ≥50.

In addition, the compounds of the present invention feature an improved stability in the cytosole of human cells, which markedly contributes to their good overall metabolic stability. The cytosolic stability can be measured for example by incubating a solution of a compound of the invention with liver cytosole from particular species (for example rat, dog, monkey or human) and determining the half-life of the compound under these conditions. It is possible to conclude from larger half-lives that the metabolic stability of the compound is improved. The stability in the presence of human liver cytosole is of particular interest because it makes it possible to predict the metabolic degradation of the compound in the human liver. Compounds with enhanced cytosolic stability therefore are likely to be degraded at reduced rates in the liver. Slower metabolic degradation in the liver in turn can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various calpain-dependent diseases. An improved metabolic stability may additionally lead to an increased bioavailability after oral administration, because the compound is subjected, after being absorbed in the intestine, to less metabolic degradation in the liver (termed the first pass effect). An increased oral bioavailability may, because the concentration (effective level) of the compound is increased, lead to a better efficacy of the compound after oral administration.

Accordingly, due to their improved cytosolic stability the compounds of the invention remain in the cytosol for extended periods, i.e. have a decreased cytosolic clearance, and therefore ought to show enhanced human pharmacokinetics.

Compounds preferred according to the invention accordingly have a cytosolic clearance in human liver cytosol of ≤30 µl/min/mg, in particular of ≤15 µl/min/mg and specifically of ≤5 µl/min/mg.

The improved cytosolic stability of the compounds according to the present invention is probably primarily due to their reduced susceptibility to aldo-keto reductases (AKRs) which mediate the metabolic degradation of compounds having a carbonyl group in the liver cytosole of humans and monkeys. Thus, the AKR-catalyzed reduction of the ketoamides of formula I should be less pronounced than that of less stable ketoamides. Hence, the ratio of the concentration of the parent compound, i.e. the ketamide of formula I, to the concentration of the metabolite, i.e. the hydroxyamide stemming form the ketoamide, is a measure for the stability of the compounds of the invention.

Compounds preferred according to the invention accordingly have, after incubation in human hepatocytes for 4 hours, a concentration ratio of the hydroxyamide metabolite to their corresponding parent compound of formula I of ≤2, in particular ≤1 and specifically ≤0.1.

Owing to their inhibitory effect on calpain, their selectivity for calpain in comparison with other cysteine proteases and their cytosolic stability the compounds of the the invention are particularly suitable for the treatment of a disorder or of a condition which is associated with an elevated calpain activity as are described for example in the prior art cited at the outset.

Disorders associated with an elevated calpain activity are in particular neurodegenerative disorders, especially those neurodegenerative disorders occuring as a result of a chronic brain supply deficit, of an ischemia (stroke) or of a trauma such as brain trauma, and the neurodegenerative disorders Alzheimer's disease, Parkinson's disease, amyotrophic lateral sclerosis and Huntington's disease, also multiple sclerosis and the damage to the nervous system associated therewith, especially damage to the optic nerve (optic neuritis) and the nerves which control the movement of the eye. Accordingly, preferred embodiments of the invention relate to the treatment of neurodegenerative disorders, especially of the aforementioned neurodegenerative disorders in humans, and to the use of the compounds of the invention of the formula I, their tautomers and their pharmaceutically suitable salts for the manufacture of a medicament for the treatment of these disorders.

Disorders associated with an elevated calpain activity also include epilepsy. Accordingly, preferred embodiments of the invention relate to the treatment of epilepsy in humans, and to the use of the compounds of the invention for the manufacture of a medicament for the treatment of epilepsy.

The disorders or conditions associated with an elevated calpain activity also include pain and painful conditions. Accordingly, preferred embodiments of the invention relate to the treatment of pain and painful conditions in mammals, especially in humans, and to the use of the compounds of the invention for the manufacture of a medicament for the treatment of pain and painful conditions.

The disorders or conditions associated with an elevated calpain activity also include damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty. Accordingly, preferred embodiments of the invention relate to the treatment of diseases or conditions associated with damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty in mammals, especially in humans, and to the use of the compounds of the invention for the manufacture of a medicament for the treatment of these disorders.

It has further emerged that inhibition of calpain brings about cytotoxic effects on tumor cells. Accordingly, the compounds of the invention are suitable for the chemotherapy of tumors and metastasis thereof. Preferred embodiments of the invention therefore relate to the use of the compounds of the invention in the therapy of tumors and metastases, and to their use for the manufacture of a medicament for the therapy of tumors and metastases.

It has further been found that various impairments associated with an HIV disorder, especially nerve damage (HIV-induced neurotoxicity), are mediated by calpain and therefore inhibition of calpain allows such impairments to be treated or alleviated. Accordingly, the compounds of the invention are suitable for the treatment of HIV patients. Preferred embodiments of the invention therefore relate to the use of the compounds of the invention for the treatment of HIV-infected patients, especially the treatment of those impairments caused by an HIV-induced neurotoxicity, and to their use for the manufacture of a medicament for the treatment of HIV patients.

It has further been found that the release of interleukin-I, TNF or beta-amyloid peptides (Aβ or Aβ-peptides) can be reduced or completely inhibited by calpain inhibitors. Accordingly, impairments or disorders associated with an elevated interleukin-I, TNF or Aβ level can be treated by using the compounds of the invention of the formula I, their tautomers and their pharmaceutically suitable salts. Preferred embodiments of the invention therefore relate to the use of the compounds of the invention o for the treatment of impairments or disorders associated with an elevated interleukin-I, TNF or Aβ level such as rheumatism, rheumatoid arthritis and to their use for the manufacture of a medicament for the treatment of such impairments or disorders.

It has further emerged that inhibition of calpain is suitable for the treatment of protozoan infection (protist infection) like malaria or toxoplasmosis (Li et al., *Mol Biochem Parasitol.* 2007; 155(1): 26-32; Jung et al. Archives of Pharmacal Research (2009), 32(6), 899-906). Hence, the compounds of the present invention are particularly suitable for treating protozoan infections like malaria or toxoplasmosis and to their use for the manufacture of a medicament for the treatment of such impairments or disorders.

Besides their improved cytosolic stability the compounds of present invention are also distinguished by a good stability against degradation in liver microsomes. The microsomal stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). Their good microsomal stability contributes to the enhanced overall metabolic stability of the compounds of the invention.

The compounds of the present invention are further distinguished by exhibiting an improved pharmacological activity, compared with the carboxamide compounds disclosed in the prior art, in patients or relevant animal models allowing prognostic statements for use in treatment.

The present invention also relates to pharmaceutical compositions (i.e. medicaments) which comprise at least one compound of the invention and, where appropriate, one or more suitable drug carriers.

These drug carriers are chosen according to the pharmaceutical form and the desired mode of administration.

The compounds of the invention can be used to manufacture pharmaceutical compositions for oral, sublingual, subcutaneous, intramuscular, intravenous, topical, intratracheal, intranasal, transdermal or rectal administration, and be administered to animals or humans in unit dose forms, mixed with conventional pharmaceutical carriers, for the prophylaxis or treatment of the above impairments or diseases.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient may vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered 1 to 5 times a day, so that a daily dose of from 0.5 to 25000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

The following examples illustrate the invention without restricting it. Depending on the management of the reaction and working up, the compounds of the invention are present as mixtures of compounds of the formula I and of the corresponding hydrates of the formula I-H. Conversion into the pure carbonyl compounds generally takes place by treating the substances with HCl in an inert solvent.

PREPARATION EXAMPLES

The intermediates used were either commercially available or prepared according to the procedures described in WO 2008/080969.

Example 1

2-[3-(4-Fluorophenyl)-1H-pyrazol-1-yl]-N-[4-(methoxyamino)-3,4-dioxo-1-phenylbutan-2-yl]pyridine-3-carboxamide 1.1 Ethyl 3-(2-(3-(4-fluorophenyl)-1H-pyrazol-1-yl) nicotinamido)-2-hydroxy-4-phenylbutanoate N-(3-Dimethylaminopropyl)-N'-ethylcarbodiimide hydrochloride (EDC) (4.47 g, 23.3 mmol), 1-hydroxybenzotriazole hydrate (HOBt) (3.57 g, 23.3 mmol) and triethylamine ($Et_3N$) (4.5 ml, 32.3 mmol) were successively added to a solution of 2-(3-(4-fluorophenyl)-1H-pyrazol-1-yl)nicotinic acid (6.0 g, 21.8 mmol) and 4-ethoxy-3-hydroxy-4-oxo-1-phenylbutan-2-aminium chloride (6.60 g, 25.4 mmol) in dichloromethane (300 ml) at 5° C., and the mixture was stirred at 5° C. for about 5 minutes. A pH of 10 was adjusted by adding 6 ml $Et_3N$, the mixture stirred for 1 h at 5° C. and then overnight at room temperature. The mixture then was concentrated under reduced pressure, poured into 1000 ml of water, the precipitate formed was filtered off with suction and dried in vacuo to give 7.8 g, which were treated 100 ml of methyl-tert.butylether to give 7.39 g of the desired product. ESI-MS $[M+H]^+$: 489.2

1.2 3-(2-(3-(4-Fluorophenyl)-1H-pyrazol-1-yl)nicotinamido)-2-hydroxy-4-phenylbutanoic acid To a suspension of ethyl 3-(2-(3-(4-fluorophenyl)-1H-pyrazol-1-yl)nicotinamido)-2-hydroxy-4-phenylbutanoate (4500 mg, 9.21 mmol) in tetrahydrofuran (THF) (500 ml) lithium hydroxide (LiOH) (441 mg, 18.42 mmol) in water (100 ml) was added, and the mixture stirred for 2 h at room temperature. After completion of the reaction (tlc: $CH_2Cl_2$+ 10% (v/v) methanol) the mixture was concentrated under reduced pressure and after addition of water (300 ml) acidified using 2 n HCl. The precipitate formed was filtered off and dried to give 4.13 g of a white amorphous solid.

$^1$H-NMR (400 MHz DMSO) δ [ppm]: 12.78 (broad, 1H), 8.65 (m, 1H), 8.42 (m, 1H), 8.30 (m, 1H), 7.90 (m, 2H), 7.75 (m, 1H), 7.50 (m, 1H), 7.18 (m, 6H), 7.0 (m, 1H), 5.26 (broad, 1H), 4.44 (m, 1H), 3.86 (s, 1H), 2.82 and 2.67 (each m, 1H).

1.3 2-(3-(4-Fluorophenyl)-1H-pyrazol-1-yl)-N-(3-hydroxy-4-(methoxyamino)-4-oxo-1-phenylbutan-2-yl)nicotinamide N,N-Diisopropylethylamine (2 ml, 11.56 mmol) was added to a suspension of 3-(2-(3-(4-fluorophenyl)-1H-pyrazol-1-yl)nicotinamido)-2-hydroxy-4-phenylbutanoic acid (700 mg, 1.520 mmol) and O-methylhydroxylamine hydrochloride (0.577 ml, 7.60 mmol) in dichloromethane (60 ml) at 5° C. with stiffing. After about 5 min 2-(1H-7-azabenzotriazol-1-yl)-1,1,3,3-tetramethyl uronium hexafluorophosphate (HATU) (665 mg, 1.748 mmol) was added, the pH value adjusted to 10 via addition of further diisopropylethylamine, and the mixture then stirred for 1 h at 5° C. and then overnight at room temperature. The reaction mixture then was concentrated, 100 ml of water added, the precipitate formed filtered off with suction and dried. The obtained crude product was treated with 20 ml of methyl-tert.butylether, filtered off and dried to give 318 mg of a white amorphous solid. Extraction of the mother liquor with dichloromethane and evaporation gave 384 mg of yellowish solid. Both fractions were combined and treated with 6 ml of pentane/dichloromethane 1:1 to give 126 mg of the desired product as white solid. ESI-MS $[M+H]^+$: 490.2

1.4 2-[3-(4-Fluorophenyl)-1H-pyrazol-1-yl]-N-[4-(methoxyamino)-3,4-dioxo-1-phenylbutan-2-yl]pyridine-3-carboxamide At 5° C. pyridine (350 μl, 4.3 mmol) and 5 ml of a solution of Dess-Martin periodinane (0.3 m in dichloromethane) were added to a solution of 2-(3-(4-fluorophenyl)-1H-pyrazol-1-yl)-N-(3-hydroxy-4-(methoxyamino)-4-oxo-1-phenylbutan-2-yl)nicotinamide (400 mg, 0.17 mmol) in DMF (3 ml) an dichloromethane (50 ml). The mixture was stirred for 1 h at 5° C., then for another 30 min at room temperature. Then 50 ml of a saturated solution $NaHCO_3$ was added, the organic layer was washed twice with water, dried, filtered and concentrated to give 423 mg of a yellow oil, which was treated with 6 ml of n-pentane/CH₂CL₂ (1:1 (v/v)) to give 123 mg of a white amorphous solid. ESI-MS [M+H]⁺: 488.2

¹H-NMR (400 MHz DMSO) δ [ppm]: 12.11 (broad, 1H), 9.01 (dd, 1H), 8.56 (dd, 1H), 8.49 (dd, 1H), 7.78 (m, 2H), 7.65 (m, 1H), 7.47 (m, 1H), 7.16 (m, (H), 7.01 (d, 1H), 5.50 (m, 1H), 3.69 (s, 3H), 3.11 and 2.81 (each dd, 1H).

Example 2

N-(4-(Methoxyamino)-3,4-dioxo-1-phenylbutan-2-yl)-2-(3-phenyl-1H-pyrazol-1-yl)nicotinamide 2.1 Ethyl 2-hydroxy-4-phenyl-3-(2-(3-phenyl-1H-pyrazol-1-yl)nicotinamido)-butanoate The reaction was carried out in analogy to reaction step 1.1 starting from 2-(3-phenyl-1H-pyrazol-1-yl)nicotinic acid and 4-ethoxy-3-hydroxy-4-oxo-1-phenylbutan-2-aminium chloride. ESI-MS [M+H]⁺=471.2

2.2 2-Hydroxy-4-phenyl-3-(2-(3-phenyl-1H-pyrazol-1-yl)nicotinamido)butanoic acid Ethyl 2-hydroxy-4-phenyl-3-(2-(3-phenyl-1H-pyrazol-1-yl)nicotinamido)-butanoate was saponified in analogy to reaction step 1.2. ESI-MS [M+H]⁺: 443.2

¹H-NMR (400 MHz DMSO) δ [ppm]: 8.54 (dd, 1H), 8.42 (d, 1H), 8.26 (d, 1H), 7.90 (d, 2H), 7.75 (dd, 1H), 7.47 (m, 1H), 7.35 (m, 2H), 7.27 (m, 2H), 7.17 (m, 4H), 6.99 (d, 1H), 4.42 (m, 1H), 3.78 (d, 1H), 2.80 and 2.67 (each m, 1H).

2.3 N-(3-Hydroxy-4-(methoxyamino)-4-oxo-1-phenylbutan-2-yl)-2-(3-phenyl-1H-pyrazol-1-yl)nicotinamide The reaction was carried out in analogy to reaction step 1.3 by reacting 2-hydroxy-4-phenyl-3-(2-(3-phenyl-1H-pyrazol-1-yl)nicotinamido)butanoic acid with O-methylhydroxylamine hydrochloride. ESI-MS [M+H]⁺: 472.2

2.4 N-(4-(Methoxyamino)-3,4-dioxo-1-phenylbutan-2-yl)-2-(3-phenyl-1H-pyrazol-1-yl)nicotinamide To a solution of N-(3-hydroxy-4-(methoxyamino)-4-oxo-1-phenylbutan-2-yl)-2-(3-phenyl-1H-pyrazol-1-yl)nicotinamide (2000 mg, 4.24 mmol) in DMSO (25 ml) at 20° C. 2-iodoxybenzoic acid (IBX) (3959 mg, 6.36 mmol) was added. More IBX (400 mg, 0.643 mmol) was added 2 times over an interval of 2 h, the mixture was stirred overnight, another 500 mg of IBX were added and stirring was continued. After the reaction was completed (tlc: CH₂Cl₂+5% (v/v) methanol) 100 ml of a saturated solution of NaHCO₃ was added dropwise, 200 ml of water and 200 ml of dichloromethane were then added and the precipitate was filtered off with suction. The dichloromethane layer was dried, filtered and concentrated to give 1.9 g of a yellowish amorphous solid, which was crystallized from ethyl acetate and dried in vacuo to give 1.1 g of the title compound. ESI-MS [M+H]⁺: 470.2

¹H-NMR (400 MHz DMSO) δ [ppm]: 12.08 (broad, 1H), 8.96 (broad, 1H), 8.55 (dd, 1H), 8.47 (dd, 1H), 7.73 (m, 3H), 7.38-7.30 (m, 5H), 7.16 (m, 6H), 6.99 (d, 1H), 5.47 (m, 1H), 3.63 (s, 3H), 3.09 and 2.80 (each dd, 1H).

Example 3

2-(4-Fluoro-3-phenyl-1H-pyrazol-1-yl)-N-(4-(methoxyamino)-3,4-dioxo-1-phenylbutan-2-yl)nicotinamide 3.1 Ethyl 2-(4-fluoro-3-phenyl-1H-pyrazol-1-yl)nicotinate To a solution of fluoro-3-phenyl-1H-pyrazole (prepared according to T. Hanamoto et al.; Tetrahedron 2007, 63 (23), 5062-5070) (0.95 g, 5.86 mmol) and ethyl 2-chloronicotinate (2.3 g, 12.39 mmol) in DMF (35 ml), K₂CO₃ (2.2 g, 15.92 mmol), 18-crown-6 (0.15 g, 0.568 mmol) and KI (0.10 g, 0.602 mmol) were added and the mixture was heated to 135° C. for 2 h. After completion of the reaction the mixture was concentrated under reduced pressure. The remainder was dissolved in dichloromethane (210 ml), washed with water, brine, dried, filtered off and concentrated to give 3.0 g of a yellow oil, which was purified further via chromatography on silica gel (eluent: CH₂Cl₂+0-4% (v/v) methanol). After evaporation of the combined product fractions 1.49 g of the title compound were obtained as an oil. ESI-MS [M+H]⁺: 312.1

3.2 2-(4-Fluoro-3-phenyl-1H-pyrazol-1-yl)nicotinic acid

To ethyl 2-(4-fluoro-3-phenyl-1H-pyrazol-1-yl)nicotinate (1.49 g, 4.79 mmol) in methanol (40 ml) 8.5 ml of an aqueous 2 m NaOH-solution (17 mmol) was added dropwise at 10° C., and the mixture stirred for 2 h at room temperature and then for 3 h at 65° C. After completion of the reaction the mixture was concentrated under reduced pressure, dissolved in water and acidified using 2 n HCl. The precipitate formed was filtered off, washed with water and dried to give 1.23 g of a white amorphous solid. ESI-MS [M+H]⁺: 284.1

3.3 Ethyl 3-(2-(4-fluoro-3-phenyl-1H-pyrazol-1-yl)nicotinamido)-2-hydroxy-4-phenylbutanoate The reaction was carried out in analogy to reaction step 1.1 by reacting 2-(4-fluoro-3-phenyl-1H-pyrazol-1-yl)nicotinic acid and 4-ethoxy-3-hydroxy-4-oxo-1-phenylbutan-2-aminium chloride. ESI-MS [M+H]⁺: 489.2

3.4 3-(2-(4-Fluoro-3-phenyl-1H-pyrazol-1-yl)nicotinamido)-2-hydroxy-4-phenylbutanoic acid Ethyl 3-(2-(4-fluoro-3-phenyl-1H-pyrazol-1-yl)nicotinamido)-2-hydroxy-4-phenylbutanoate was saponified in analogy to reaction step 1.2. ESI-MS [M+H]⁺: 461.2

3.5 2-(4-Fluoro-3-phenyl-1H-pyrazol-1-yl)-N-(3-hydroxy-4-(methoxyamino)-4-oxo-1-phenylbutan-2-yl)nicotinamide The reaction was carried out in analogy to reaction step 1.3 by reacting 3-(2-(4-fluoro-3-phenyl-1H-pyrazol-1-yl)nicotinamido)-2-hydroxy-4-phenylbutanoic acid with O-methylhydroxylamine hydrochloride. ESI-MS [M+H]⁺: 490.2

3.6 2-(4-Fluoro-3-phenyl-1H-pyrazol-1-yl)-N-(4-(methoxyamino)-3,4-dioxo-1-phenylbutan-2-yl)nicotinamide 2-(4-Fluoro-3-phenyl-1H-pyrazol-1-yl)-N-(3-hydroxy-4-(methoxyamino)-4-oxo-1-phenylbutan-2-yl)nicotinamide was oxidized in analogy to reaction step 2.4. ESI-MS [M+H]⁺: 488.2

¹H-NMR (400 MHz DMSO) δ [ppm]: 8.77 (m, 2H), 8.52 (d, 1H), 7.50 (m, 1H), 7.65 (m, 2H), 7.44 (m, 3H), 7.31 (m, 1H), 7.08 (m, 5H), 5.60 (m, 1H), 3.59 (s, 3H), 3.30 (superimposed by water), 2.69 (m, 1H).

Example 4

N-[4-(Methoxyamino)-3,4-dioxo-1-phenylbutan-2-yl]-2-(4-methyl-3-phenyl-1H-pyrazol-1-yl)pyridine-3-carboxamide

4.1 Ethyl 2-hydroxy-3-(2-(4-methyl-3-phenyl-1H-pyrazol-1-yl)nicotinamido)-4-phenylbutanoate The reaction was carried out in analogy to reaction step 1.1 by reacting 2-(4-methyl-3-phenyl-1H-pyrazol-1-yl)nicotinic acid and 4-ethoxy-3-hydroxy-4-oxo-1-phenylbutan-2-aminium chloride. ESI-MS [M+H]⁺: 485.3

4.2 3-(2-(4-Methyl-3-phenyl-1H-pyrazol-1-yl)nicotinamido)-2-hydroxy-4-phenylbutanoic acid Ethyl 2-hydroxy-3-(2-(4-methyl-3-phenyl-1H-pyrazol-1-yl)nicotinamido)-4-phenylbutanoate was saponified in analogy to reaction step 1.2. ESI-MS [M+H]⁺: 457.2

4.3 N-(3-Hydroxy-4-(methoxyamino)-4-oxo-1-phenylbutan-2-yl)-2-(4-methyl-3-phenyl-1H-pyrazol-1-yl)nicotinamide The reaction was carried out in analogy to reaction step 1.3 by reacting 3-(2-(4-methyl-3-phenyl-1H-pyrazol-1-yl)nicotinamido)-2-hydroxy-4-phenylbutanoic acid with O-methylhydroxylamine hydrochloride. ESI-MS [M+H]⁺: 486.2

4.4 N-[4-(Methoxyamino)-3,4-dioxo-1-phenylbutan-2-yl]-2-(4-methyl-3-phenyl-1H-pyrazol-1-yl)pyridine-3-carboxamide To polymer-supported IBX (Novabiochem, 1.1 mmol/g; 300 mg, 0.330 mmol) dichloromethane (5 ml) was added and the mixture was left for 10 min. Then N-(3-hydroxy-4-(methoxyamino)-4-oxo-1-phenylbutan-2-yl)-2-(4-methyl-3-phenyl-1H-pyrazol-1-yl)nicotinamide (77 mg, 0.159 mmol) in 10 ml of dichloromethane was added and the mixture was shaken for 1 day at room temperature. Additional portions of the polymer-supported IBX were added after 2 days and 3 days (120 mg, 0.132 mmol and 100 mg, 0.110 mmol). After 4 days the mixture was filtered off, evaporated under reduced pressure and the crude product purified via chromatography on silica gel (eluent: CH₂Cl₂+2-4% (v/v) methanol). After evaporation of the combined product fractions 45 mg of an amorphous solid were obtained. ESI-MS [M+H]⁺: 484.2

Example 5

N-(1-(4-Fluorophenyl)-4-(methoxyamino)-3,4-dioxo-butan-2-yl)-2-(3-phenyl-1H-pyrazol-1-yl)nicotinamide 3-(2-(3-Phenyl-1H-pyrazol-1-yl)nicotinamido)-2-hydroxy-4-(4-fluorophenyl)-butanoic acid was prepared using processes analogous to steps 1.1 and 1.2.

5.1 N-(1-(4-Fluorophenyl)-3-hydroxy-4-(methoxyamino)-4-oxo-butan-2-yl)-2-(3-phenyl-1H-pyrazol-1-yl)nicotinamide The reaction was carried out in analogy to reaction step 1.3 by reacting 3-(2-(3-phenyl-1H-pyrazol-1-yl)nicotinamido)-2-hydroxy-4-(4-fluorophenyl)-butanoic acid with O-methylhydroxylamine hydrochloride. ESI-MS [M+H]⁺: 490.1

5.2 N-(1-(4-Fluorophenyl)-4-(methoxyamino)-3,4-dioxo-butan-2-yl)-2-(3-phenyl-1H-pyrazol-1-yl)nicotinamide N-(1-(4-Fluorophenyl)-3-hydroxy-4-(methoxyamino)-4-oxo-butan-2-yl)-2-(3-phenyl-1H-pyrazol-1-yl)nicotinamide was oxidized in analogy to reaction step 2.4. ESI-MS [M+H]⁺: 488.2

¹H-NMR (400 MHz DMSO) δ [ppm]: 12.14 (broad, 1H), 9.01 (m, 1H), 8.57 (m, 1H), 8.50 (m, 1H), 7.71 (m, 3H), 7.50 (m, 1H), 7.38 (m, 3H), 7.16 (m, 2H), 7.01 (m, 3H), 5.44 (m, 1H), 3.69 (s broad, 3H), 3.12 and 2.76 (each m, 1H).

Example 6

N-(1-(3-Fluorophenyl)-4-(methoxyamino)-3,4-dioxobutan-2-yl)-2-(3-phenyl-1H-pyrazol-1-yl)nicotinamide 3-(2-(3-Phenyl-1H-pyrazol-1-yl)nicotinamido)-2-hydroxy-4-(3-fluorophenyl)-butanoic acid was prepared using processes analogous to steps 1.1 and 1.2.

6.1 N-(1-(3-Fluorophenyl)-3-hydroxy-4-(methoxyamino)-4-oxo-butan-2-yl)-2-(3-phenyl-1H-pyrazol-1-yl)nicotinamide The reaction was carried out in analogy to reaction step 1.3 by reacting 3-(2-(3-phenyl-1H-pyrazol-1-yl)nicotinamido)-2-hydroxy-4-(3-fluorophenyl)-butanoic acid with O-methylhydroxylamine hydrochloride. ESI-MS [M+H]⁺: 490.2

6.2 N-(1-(3-Fluorophenyl)-4-(methoxyamino)-3,4-dioxobutan-2-yl)-2-(3-phenyl-1H-pyrazol-1-yl)nicotinamide N-(1-(3-Fluorophenyl)-3-hydroxy-4-(methoxyamino)-4-oxo-butan-2-yl)-2-(3-phenyl-1H-pyrazol-1-yl)nicotinamide was oxidized in analogy to reaction step 2.4. ESI-MS [M+H]⁺: 488.2

¹H-NMR (400 MHz DMSO) δ [ppm]: 9.08 (m, 1H), 8.60 (m, 1H), 8.47 (m, 1H), 7.73 (m, 3H), 7.49 (m, 1H), 7.33 (m, 3H), 7.12 (m, 1H), 6.94 (m, 4H), 5.52 (m, 1H), 3.70 (s, 3H), 3.13 and 2.81 (each m, 1H).

Example 7

N-(4-(Ethoxyamino)-3,4-dioxo-1-phenylbutan-2-yl)-2-(3-phenyl-1H-pyrazol-1-yl)nicotinamide

7.1 N-(4-(Ethoxyamino)-3-hydroxy-4-oxo-1-phenylbutan-2-yl)-2-(3-phenyl-1H-pyrazol-1-yl)nicotinamide The reaction was carried out in analogy to reaction step 1.3 by reacting 2-hydroxy-4-phenyl-3-(2-(3-phenyl-1H-pyrazol-1-yl)nicotinamido)butanoic acid with O-ethylhydroxylamine hydrochloride. ESI-MS [M+H]⁺: 486.2

7.2 N-(4-(Ethoxyamino)-3,4-dioxo-1-phenylbutan-2-yl)-2-(3-phenyl-1H-pyrazol-1-yl)nicotinamide N-(4-(Ethoxyamino)-3-hydroxy-4-oxo-1-phenylbutan-2-yl)-2-(3-phenyl-1H-pyrazol-1-yl)nicotinamide was oxidized in analogy to reaction step 2.4. ESI-MS [M+H]⁺: 484.2

¹H-NMR (400 MHz DMSO) δ [ppm]: 11.82 (broad, 1H), 8.88 (m, 1H), 8.54 (m, 1H), 8.36 (m, 1H), 7.71 (m, 3H), 7.44 (m, 1H), 7.35 (m, 3H), 7.17 (m, 5H), 6.94 (m, 1H), 5.50 (m, 1H), 3.89 (m, 2H), 3.12 and 2.84 (each m, 1H), 1.16 (m, 3H).

Example 8

N-(4-(Allyloxyamino)-3,4-dioxo-1-phenylbutan-2-yl)-2-(3-phenyl-1H-pyrazol-1-yl)nicotinamide

8.1 N-(4-(Allyloxyamino)-3-hydroxy-4-oxo-1-phenylbutan-2-yl)-2-(3-phenyl-1H-pyrazol-1-yl)nicotinamide The reaction was carried out in analogy to reaction step 1.3 by reacting 2-hydroxy-4-phenyl-3-(2-(3-phenyl-1H-pyrazol-1-yl)nicotinamido)butanoic acid with O-allylhydroxylamine hydrochloride. ESI-MS [M+H]⁺: 498.2

8.2 N-(4-(Allyloxyamino)-3,4-dioxo-1-phenylbutan-2-yl)-2-(3-phenyl-1H-pyrazol-1-yl)nicotinamide N-(4-(Allyloxyamino)-3-hydroxy-4-oxo-1-phenylbutan-2-yl)-2-(3-phenyl-1H-pyrazol-1-yl)nicotinamide was oxidized in analogy to reaction step 2.4. ESI-MS [M+H]⁺: 496.2

¹H-NMR (400 MHz DMSO) δ [ppm]: 12.1 (broad, 1H), 9.01 (m, 1H), 8.71 (m, 1H), 8.28 (m, 1H), 7.72 (m, 3H), 7.466 (m, 1H), 7.36 (m, 2H), 7.18 (m, 5H), 7.01 (m, 1H), 5.95 (m, 1H), 5.51 (m, 1H), 5.36 (m, 1H), 5.24 (m, 1H), 4.35 (m, 3H), 3.08 (m, 2H), 2.78 (m, 1H).

Example 9

N-(4-(Methoxyamino)-1-(4-methoxyphenyl)-3,4-dioxo-butan-2-yl)-2-(3-phenyl-1H-pyrazol-1-yl)nicotinamide 3-(2-(3-Phenyl-1H-pyrazol-1-yl)nicotinamido)-2-hydroxy-4-(4-methoxyphenyl)-butanoic acid was prepared using processes analogous to steps 1.1 and 1.2.

9.1 N-(3-Hydroxy-4-(methoxyamino)-4-oxo-1-(4-methoxyphenyl)-butan-2-yl)-2-(3-phenyl-1H-pyrazol-1-yl)nicotinamide The reaction was carried out in analogy to reaction step 1.3 by reacting 2-hydroxy-4-(4-methoxyphenyl)-3-(2-(3-phenyl-1H-pyrazol-1-yl)nicotinamido)butanoic acid with O-methylhydroxylamine hydrochloride. ESI-MS [M+H]⁺: 502.2

9.2 N-(4-(Methoxyamino)-1-(4-methoxyphenyl)-3,4-dioxo-butan-2-yl)-2-(3-phenyl-1H-pyrazol-1-yl)nicotinamide N-(3-Hydroxy-4-(methoxyamino)-4-oxo-1-(4-methoxyphenyl)-butan-2-yl)-2-(3-phenyl-1H-pyrazol-1-yl)nicotinamide was oxidized in analogy to reaction step 2.4. ESI-MS [M+H]⁺: 500.2

¹H-NMR (400 MHz DMSO) δ [ppm]: 12.17 (s, 1H), 8.88 (m, 1H), 8.55 (m, 1H), 8.47 (m, 1H), 7.74 (m, 4H), 7.48 (m, 1H), 7.40 (m, 3H), 6.99 (m, 2H), 6.90 (m, 1H), 6.71 (m, 2H), 5.55 (m, 1H), 3.54 (s, 6H), 3.13 and 2.67 (each m, 1H).

Example 10

2-(4-Chloro-3-phenyl-1H-pyrazol-1-yl)-N-(4-(methoxyamino)-3,4-dioxo-1-phenylbutan-2-yl)nicotinamide

10.1 4-Chloro-3-phenyl-1H-pyrazole

To a solution of 3-phenyl-1H-pyrazole (3 g, 20.81 mmol) in dichloroethane (60 ml) N-chlorosuccinimide (2.92 g, 21.85 mmol) was added and the mixture was stirred over night at room temperature. The mixture was then concentrated under reduced pressure and the remainder was purified via chromatography on silica gel (eluent: cyclohexane/ethyl acetate 0-30% (v/v)). Concentration of the combined fractions gave 3.54 g of a slightly yellow amorphous solid; ESI-MS [M+H]⁺: 179.0

10.2 Ethyl 2-(4-chloro-3-phenyl-1H-pyrazol-1-yl)nicotinate

The reaction was carried out in analogy to reaction step 3.1 by reacting 4-chloro-3-phenyl-1H-pyrazole and ethyl 2-chloronicotinate. ESI-MS [M+H]⁺: 328.1

10.3 2-(4-Chloro-3-phenyl-1H-pyrazol-1-yl)nicotinic acid

Ethyl 2-(4-chloro-3-phenyl-1H-pyrazol-1-yl)nicotinate was saponified in analogy to reaction step 3.2. ESI-MS [M+H]⁺: 300.2

10.4 Ethyl 3-(2-(4-chloro-3-phenyl-1H-pyrazol-1-yl)nicotinamido)-2-hydroxy-4-phenylbutanoate The reaction was carried out in analogy to reaction step 1.1 by reacting 2-(4-chloro-3-phenyl-1H-pyrazol-1-yl)nicotinic acid and 4-ethoxy-3-hydroxy-4-oxo-1-phenylbutan-2-aminium chloride. ESI-MS [M+H]⁺: 505.15

10.5 3-(2-(4-Chloro-3-phenyl-1H-pyrazol-1-yl)nicotinamido)-2-hydroxy-4-phenylbutanoic acid Ethyl 3-(2-(4-chloro-3-phenyl-1H-pyrazol-1-yl)nicotinamido)-2-hydroxy-4-phenylbutanoate was saponified in analogy to reaction step 1.2. ESI-MS [M+H]⁺: 477.1

10.6 2-(4-Chloro-3-phenyl-1H-pyrazol-1-yl)-N-(3-hydroxy-4-(methoxyamino)-4-oxo-1-phenylbutan-2-yl)nicotinamide The reaction was carried out in analogy to reaction step 1.3 by reacting 3-(2-(4-Chloro-3-phenyl-1H-pyrazol-1-yl)nicotinamido)-2-hydroxy-4-phenylbutanoic acid with O-methylhydroxylamine hydrochloride. ESI-MS [M+H]⁺: 506.2

10.7 2-(4-Chloro-3-phenyl-1H-pyrazol-1-yl)-N-(4-(methoxyamino)-3,4-dioxo-1-phenylbutan-2-yl)nicotinamide 2-(4-Chloro-3-phenyl-1H-pyrazol-1-yl)-N-(3-hydroxy-4-(methoxyamino)-4-oxo-1-phenylbutan-2-yl)nicotinamide was oxidized in analogy to reaction step 2.4. ESI-MS [M+H]⁺: 504.15

¹H-NMR (400 MHz DMSO) δ [ppm]: 12.05 (s broad, 1H), 9.06 (m, 1H), 8.75 (s, 1H), 8.60 (m, 1H), 7.80 (m, 3H), 7.55/m, 1H), 7.44 (m, 3H), 7.17 (m, 6H), 5.48 (m 3.70 (s, 3H), 3.13 and 2.78 (each m, 1H).

Example 11

N-[4-(Isopropoxyamino)-3,4-dioxo-1-phenyl-2-butanyl]-2-(3-phenyl-1H-pyrazol-1-yl)nicotinamide 11.1 N-(3-Hydroxy-4-(isopropoxyamino)-4-oxo-1-phenylbutan-2-yl)-2-(3-phenyl-1H-pyrazol-1-yl)nicotinamide

ESI-MS [M+H+]: 500.2

11.2 N-[4-(Isopropoxyamino)-3,4-dioxo-1-phenyl-2-butanyl]-2-(3-phenyl-1H-pyrazol-1-yl)nicotinamide

ESI-MS [M+H+]: 498.2

Example 12

N-[3,4-Dioxo-1-phenyl-4-(propoxyamino)-2-butanyl]-2-(3-phenyl-1H-pyrazol-1-yl)nicotinamide 12.1 N-(3-Hydroxy-4-oxo-1-phenyl-4-(propoxyamino)butan-2-yl)-2-(3-phenyl-1H-pyrazol-1-yl)nicotinamide

ESI-MS [M+H+]: 500.2

12.2 N-[3,4-Dioxo-1-phenyl-4-(propoxyamino)-2-butanyl]-2-(3-phenyl-1H-pyrazol-1-yl)nicotinamide ESI-MS [M+H+]: 498.2
¹H-NMR (400 MHz DMSO), δ [ppm] (confomers, major/minor): 12.05/11.25 (s broad, 1H), 9.05/8.95 (broad, 1H), 8.55 (m, 2H), 7.97-7.70 (m, 3H), 7.48-7.37 (m, 4H), 7.19 (m, 5H), 7.02 (s, 1H), 5.51/5.65 (broad, 1H), 3.77/4.06 (broad, 2H), 3.14 and 2.84 (each broad, 2H), 1.70-1.57 (m, 3H), 0.92 (m, 4H).

Example 13

N-[4-(Methoxyamino)-3,4-dioxo-1-phenyl-2-butanyl]-2-{3-[4-(4-morpholinyl)phenyl]-1H-pyrazol-1-yl}nicotinamide 13.1 N-(3-hydroxy-4-(methoxyamino)-4-oxo-1-phenylbutan-2-yl)-2-(3-(4-morpholinophenyl)-1H-pyrazol-1-yl)nicotinamide

ESI-MS [M+H+]: 557.2

13.2 N-[4-(Methoxyamino)-3,4-dioxo-1-phenyl-2-butanyl]-2-{3-[4-(4-morpholinyl)phenyl]-1H-pyrazol-1-yl}nicotinamide ESI-MS [M+H+]: 555.2
¹H-NMR (400 MHz DMSO), δ [ppm]: 12.12 (s broad, 1H), 8.98 (broad, 1H), 8.53 (s, 1H), 8.44 (s, 1H) 7.70 (m, 1H), 7.63 (m, 2H), 7.44 (m, 1H), 7.19 (m, 5H), 6.93 (m, 3H), 5.48 (m, 1H), 3.78 (m, 4H), 3.63 (s broad, 3H), 3.17 (m, 5H), 2.83 (m, 1H).

Example 14

N-[4-(Methoxyamino)-3,4-dioxo-1-phenyl-2-butanyl]-2-{3-[4-(4-morpholinylmethyl)phenyl]-1H-pyrazol-1-yl}nicotinamide 14.1 N-(3-Hydroxy-4-(methoxyamino)-4-oxo-1-phenylbutan-2-yl)-2-(3-(4-(morpholinomethyl)phenyl)-1H-pyrazol-1-yl)nicotinamide

ESI-MS [M+H+]: 571.2

14.2 N-[4-(Methoxyamino)-3,4-dioxo-1-phenyl-2-butanyl]-2-{3-[4-(4-morpholinylmethyl)phenyl]-1H-pyrazol-1-yl}nicotinamide ESI-MS [M+H+]: 569.2
¹H-NMR (400 MHz DMSO), δ [ppm]: 12.10 (broad, 1H), 8.99 (s, 1H), 8.55 (d, 1H), 8.49 (s, 1H), 7.72 (m, 3h), 7.47 (m, 1H), 7.33 (m, 2H), 7.17 (m, 5H), 6.98 (s, 1H), 5.50 (m, 1H), 3.69 (s broad, 3H), 3.59-3.44 (superimposed by water), 3.13 and 2.82 (each dd, 1H), 2.37 (m, 4H).

Example 15

2-(3-{4-[(Diethylamino)methyl]phenyl}-1H-pyrazol-1-yl)-N-[4-(methoxyamino)-3,4-dioxo-1-phenyl-2-butanyl]nicotinamide 15.1 2-(3-(4-((Diethylamino)methyl)phenyl)-1H-pyrazol-1-yl)-N-(3-hydroxy-4-(methoxyamino)-4-oxo-1-phenylbutan-2-yl)nicotinamide

ESI-MS [M+H+]: 557.2

15.2 2-(3-{4-[(Diethylamino)methyl]phenyl}-1H-pyrazol-1-yl)-N-[4-(methoxyamino)-3,4-dioxo-1-phenyl-2-butanyl]nicotinamide ESI-MS [M+H+]: 555.2
¹H-NMR (400 MHz DMSO), δ [ppm]: 8.97 (d, 1 h), 8.55 (s, 1H), 8.48 (s, 1H), 7.72 (m, 3H), 7.46 (m, 1H), 7.35 (d, 2H), 7.18 (m, 5H), 6.98 (s, 1H), 5.50 (m, 1H), 3.69 (s, 2H), 3.48 (superimposed by water, 4H), 3.11 and 2.82 (each dd, 1 h), 2.49 (m, 4H).

Example 16

N-(4-{[(2-Methyl-2-propanyl)oxy]amino}-3,4-dioxo-1-phenyl-2-butanyl)-2-(3-phenyl-1H-pyrazol-1-yl)nicotinamide 16.1 N-(4-(tert-Butoxyamino)-3-hydroxy-4-oxo-1-phenylbutan-2-yl)-2-(3-phenyl-1H-pyrazol-1-yl)nicotinamide

ESI-MS [M+H+]: 514.2

16.2 N-(4-{[(2-Methyl-2-propanyl)oxy]amino}-3,4-dioxo-1-phenyl-2-butanyl)-2-(3-phenyl-1H-pyrazol-1-yl)nicotinamide ESI-MS [M+H+]: 512.2
¹H-NMR (400 MHz DMSO), (confomers, major/minor) δ [ppm]: 11.4/10.95 (s broad, 1H), 9.00/8.90 (m, 1H), 8.55-

8.48 (m, 2H), 7.75 (m, 3H), 7.46 (m, 1 h), 7.35 (m, 3H), 7.18 8m, 5H), 6.99 (m, 1H), 5.71/5.44 (m, 1 h), 3.13 and 2.81 (each m, 1 h), 1.18/1.33 (s, 9H).

Example 17

N-{4-[(Cyclopentyloxy)amino]-3,4-dioxo-1-phenyl-2-butanyl}-2-(3-phenyl-1H-pyrazol-1-yl)nicotinamide 17.1 N-(4-(Cyclopentyloxyamino)-3-hydroxy-4-oxo-1-phenylbutan-2-yl)-2-(3-phenyl-1H-pyrazol-1-yl)nicotinamide

ESI-MS [M+H+]: 526.2

17.2 N-{4-[(Cyclopentyloxy)amino]-3,4-dioxo-1-phenyl-2-butanyl}-2-(3-phenyl-1H-pyrazol-1-yl)nicotinamide ESI-MS [M+H+]: 524.2
$^1$H-NMR (400 MHz DMSO) δ [ppm]: 11.8 s broad, 1H), 8.98 (s, 1H), 8.55 (s, 1H), 8.48 (s, 1H), 7.73 (3H), 7.46 (m, 1H), 7.38 (m, 3H), 7.17 (m, 5H), 7.00 (s, 1H), 5.50 (m, 1H), 4.49 (m, 1H), 3.12 and 2.81 (each m, 1H), 1.74-1.50 (m, 8H).

Example 18

N-[4-(Ethoxyamino)-1-(4-fluorophenyl)-3,4-dioxo-2-butanyl]-2-(3-phenyl-1H-pyrazol-1-yl)nicotinamide 18.1 N-(4-(Ethoxyamino)-1-(4-fluorophenyl)-3-hydroxy-4-oxobutan-2-yl)-2-(3-phenyl-1H-pyrazol-1-yl)nicotinamide

ESI-MS [M+H+]: 504.2

18.2 N-[4-(Ethoxyamino)-1-(4-fluorophenyl)-3,4-dioxo-2-butanyl]-2-(3-phenyl-1H-pyrazol-1-yl)nicotinamide ESI-MS [M+H+]: 502.2
$^1$H-NMR (400 MHz DMSO) δ [ppm]: 11.8 (broad, 1H), 8.97 (s, 1H), 8.57 (s, 1H), 8.50 (s, 1H), 7.74 (m, 2H), 7.49 (m, 1H), 7.38 (m, 3H), 7.35 (m, 2H), 7.15 (m, 4H), 5.43 (m, 1H), 3.91 (m, 2H), 3.09 and 2.79 (each m, 1H), 1.20 (m, 3H).

Example 19

N-[4-(Ethoxyamino)-3,4-dioxo-1-phenyl-2-butanyl]-2-(4-fluoro-3-phenyl-1H-pyrazol-1-yl)nicotinamide 19.1 N-(4-(Ethoxyamino)-3-hydroxy-4-oxo-1-phenylbutan-2-yl)-2-(4-fluoro-3-phenyl-1H-pyrazol-1-yl)nicotinamide

ESI-MS [M+H+]: 504.2

19.2 N-[4-(Ethoxyamino)-3,4-dioxo-1-phenyl-2-butanyl]-2-(4-fluoro-3-phenyl-1H-pyrazol-1-yl)nicotinamide ESI-MS [M+H+]: 502.2
$^1$H-NMR (400 MHz DMSO) δ [ppm]: 11.90 (broad, 1H9, 9.00 (broad, 1H), 8.65 (d, 1H), 8.57 (d, 1H), 7.76 (m, 1H), 7.70 (m, 2H), 7.51 (m, 1H), 7.44 (m, 3H), 7.16 (m, 5H), 5.49 (m, 1h), 3.92 (m broad, 2H), 3.12 and 2.79 (each dd, 1H), 1.19 (m, 3H).

Example 20

N-{4-[(Cyclobutyloxy)amino]-3,4-dioxo-1-phenyl-2-butanyl}-2-(3-phenyl-1H-pyrazol-1-yl)nicotinamide 20.1 N-(4-(Cyclobutoxyamino)-3-hydroxy-4-oxo-1-phenylbutan-2-yl)-2-(3-phenyl-1H-pyrazol-1-yl)nicotinamide

ESI-MS [M+H+]: 512.2

20.2 N-{4-[(Cyclobutyloxy)amino]-3,4-dioxo-1-phenyl-2-butanyl}-2-(3-phenyl-1H-pyrazol-1-yl)nicotinamide ESI-MS [M+H+]: 502.2
$^1$H-NMR (400 MHz DMSO) δ [ppm]: 11.94 (s broad, 1H), 8.95 (broad, 1H), 8.55 (d, 1H), 8.47 (d, 1H), 7.76 (m, 3H), 7.48 (m, 1H), 7.36 (m, 3H), 7.15 (m, 5H), 6.99 (d, 1H), 5.48 (m, 1H), 4.39 (m, 1H), 3.10 and 2.82 (each m, 1H), 2.10 (m, 4H), 1.50 and 0.50 (each m, 1H).

Example 21

N-{4-[(2,2-Dimethylpropoxy)amino]-3,4-dioxo-1-phenyl-2-butanyl}-2-(3-phenyl-1H-pyrazol-1-yl)nicotinamide 21.1 N-(3-Hydroxy-4-(neopentyloxyamino)-4-oxo-1-phenylbutan-2-yl)-2-(3-phenyl-1H-pyrazol-1-yl)nicotinamide

ESI-MS [M+H+]: 528.2

21.2 N-{4-[(2,2-Dimethylpropoxy)amino]-3,4-dioxo-1-phenyl-2-butanyl}-2-(3-phenyl-1H-pyrazol-1-yl)nicotinamide ESI-MS [M+H+]: 526.2
$^1$H-NMR (400 MHz DMSO) δ [ppm]: 12.03 (broad, 1H), 8.94 (broad, 1H), 8.55 (d, 1H), 8.46 (d, 1H), 7.75 (m, 3H), 7.47 (m, 1H), 7.40 (m, 3H), 7.17 (m, 5H), 6.99 (s, 1H), 5.49 (m, 1H), 3.48 (broad, 2H), 3.08 and 2.81 (each dd, 1H), 0.90 (s, 9H).

Example 22

N-(4-{[2-(4-Morpholinyl)ethoxy]amino}-3,4-dioxo-1-phenyl-2-butanyl)-2-(3-phenyl-1H-pyrazol-1-yl)nicotinamide 22.1 N-(3-Hydroxy-4-(2-morpholinoethoxyamino)-4-oxo-1-phenylbutan-2-yl)-2-(3-phenyl-1H-pyrazol-1-yl)nicotinamide

ESI-MS [M+H+]: 571.2

22.2 N-(4-{[2-(4-Morpholinyl)ethoxy]amino}-3,4-dioxo-1-phenyl-2-butanyl)-2-(3-phenyl-1H-pyrazol-1-yl)nicotinamide

ESI-MS [M+H+]: 569.2

Example 23

N-{4-[(Cyclopropylmethoxy)amino]-3,4-dioxo-1-phenyl-2-butanyl}-2-(3-phenyl-1H-pyrazol-1-yl)nicotinamide 23.1 N-(4-(Cyclopropylmethoxyamino)-3-hydroxy-4-oxo-1-phenylbutan-2-yl)-2-(3-phenyl-1H-pyrazol-1-yl)nicotinamide

ESI-MS [M+H+]: 512.2

23.2 N-{4-[(Cyclopropylmethoxy)amino]-3,4-dioxo-1-phenyl-2-butanyl}-2-(3-phenyl-1H-pyrazol-1-yl)nicotinamide ESI-MS [M+H+]: 510.2
$^1$H-NMR (400 MHz DMSO) δ [ppm]: 11.97 (broad, 1H), 8.93 (broad, 1H9, 8.55 8d, 1H), 8.46 (d, 1H), 7.75-7.50 (m, 3H), 7.46 (m, 1H), 7.38 (m, 3H), 7.18 (m, 5H), 6.99 (d, 1H), 5.49 (m, 1H), 3.61 (broad, 2H), 3.10 and 2.82 (each dd, 1H), 1.05 (m, 1H), 0.51 and 0.24 (each m, 2H).

Example 24

N-[4-(Ethoxyamino)-1-(4-methoxyphenyl)-3,4-dioxo-2-butanyl]-2-(3-phenyl-1H-pyrazol-1-yl)nicotinamid 24.1 N-(4-(Ethoxyamino)-3-hydroxy-1-(4-methoxyphenyl)-4-oxobutan-2-yl)-2-(3-phenyl-1H-pyrazol-1-yl)nicotinamide
ESI-MS [M+H+]: 514.2

24.2 N-[4-(Ethoxyamino)-1-(4-methoxyphenyl)-3,4-dioxo-2-butanyl]-2-(3-phenyl-1H-pyrazol-1-yl)nicotinamid ESI-MS [M+H+]: 514.2
$^1$H-NMR (400 MHz DMSO) δ [ppm]: 11.94 (broad, 1H), 8.89 (broad, 1H), 8.55 (d, 1H9, 8.47 (d, 1H), 7.74 (m, 3H), 7.49 (m, 1H), 7.38 (m, 1H), 7.35 (m, 3H), 7.06 (m, 2H), 6.99 (m, 1H), 6.73 (m, 2H), 5.43 (m, 1H9, 3.84 (broad, 2H), 3.71 (s, 3H), 3.03 and 2.74 (each m, 1H), 1.16 (m, 3H).

Example 25

2-[3-(2-Fluorophenyl)-1H-pyrazol-1-yl]-N-[4-(methoxyamino)-3,4-dioxo-1-phenyl-2-butanyl]nicotinamide 25.1 2-(3-(2-Fluorophenyl)-1H-pyrazol-1-yl)-N-(3-hydroxy-4-(methoxyamino)-4-oxo-1-phenylbutan-2-yl)nicotinamide

ESI-MS [M+H+]: 490.2

25.2 2-[3-(2-Fluorophenyl)-1H-pyrazol-1-yl]-N-[4-(methoxyamino)-3,4-dioxo-1-phenyl-2-butanyl]nicotinamide ESI-MS [M+H+]: 488.2
$^1$H-NMR (400 MHz DMSO) δ [ppm]: 12.08 (broad, 1H), 9.00 (broad, 1H), 8.59 (d, 1H), 8.54 (s, 1H), 7.76 (m, 2H), 7.52 (m, 1h), 7.49 (m, 1H), 7.32 (m, 1H), 7.19 (m, 6H), 6.87 (s, 1H), 5.49 (m, 1H), 3.69 (m, 3H), 3.11 and 2.79 (each dd, 1H).

Example 26

N-[4-(Methoxyamino)-3,4-dioxo-1-phenyl-2-butanyl]-2-{3-[3-(trifluoromethyl)phenyl]-1H-pyrazol-1-yl}nicotinamide 26.1 N-(3-Hydroxy-4-(methoxyamino)-4-oxo-1-phenylbutan-2-yl)-2-(3-(3-(trifluoromethyl)phenyl)-1H-pyrazol-1-yl)nicotinamide

ESI-MS [M+H+]: 538.2

26.2 N-[4-(Methoxyamino)-3,4-dioxo-1-phenyl-2-butanyl]-2-{3-[3-(trifluoromethyl)phenyl]-1H-pyrazol-1-yl}nicotinamide ESI-MS [M+H+]: 540.2
$^1$H-NMR (400 MHz DMSO) δ [ppm]:12.01 (broad, 1H), 8.97 (broad, 1H), 8.58 (d, 1H), 8.52 (s, 1H), 8.09 (s, 1H), 8.02 (m, 1H), 7.77 (m, 1H), 7.69 (m, 1H), 7.62 (m, 1H), 7.51 (m, 1H), 7.17 (s, 1H), 7.08 (m, 5H), 5.39 (m, 1H), 3.67 (m, 3H), 3.10 and 2.76 (each dd, 1H).

Example 27

N-[4-(Methoxyamino)-3,4-dioxo-1-phenyl-2-butanyl]-2-[3-(2-pyridinyl)-1H-pyrazol-1-yl]nicotinamide 27.1 N-(3-Hydroxy-4-(methoxyamino)-4-oxo-1-phenylbutan-2-yl)-2-(3-(pyridin-2-yl)-1H-pyrazol-1-yl)nicotinamide

ESI-MS [M+H+]: 473.2.

27.2 N-[4-(Methoxyamino)-3,4-dioxo-1-phenyl-2-butanyl]-2-[3-(2-pyridinyl)-1H-pyrazol-1-yl]nicotinamide ESI-MS [M+H+]: 471.1
$^1$H-NMR (400 MHz DMSO) δ [ppm]: 12.11 (broad, 1H), 8.99 (broad, 1H), 8.58 (m, 2H), 8.49 (d, 1H), 7.74 (m, 3H), 7.50, (dd, 1H), 7.34 (dd, 1H), 7.20 (m, 5H), 7.03 (d, 1H), 5.48 (m, 1H), 3.64 (broad, 3H), 3.10 and 2.76 (each dd, 1H).

Example 28 (Comparative)

N-(3-Amino-1-benzyl-2,3-dioxopropyl)-2-[3-(4-fluorophenyl)-1H-pyrazol-1-yl]nicotinamide The title compound is identical with the compound of Example 38 of WO 08/080969 and was prepared as described therein.

Example 29

(2R)-1-benzyl-N-(4-(ethoxyamino)-3,4-dioxo-1-phenylbutan-2-yl)-5-oxopyrrolidine-2-carboxamide The building block (R)-1-Benzyl-5-oxo-pyrrolidine-2-carboxylic acid which was used in the following example is commercially available.

29.1 Ethyl 3-((R)-1-benzyl-5-oxopyrrolidine-2-carboxamido)-2-hydroxy-4-phenylbutanoate The reaction was carried out in analogy to reaction step 1.1 by reacting (R)-1-benzyl-5-oxopyrrolidine-2-carboxylic acid and 4-ethoxy-3-hydroxy-4-oxo-1-phenylbutan-2-aminium chloride. ESI-MS [M+H]$^+$=425.2.

29.2 3-((R)-1-benzyl-5-oxopyrrolidine-2-carboxamido)-2-hydroxy-4-phenylbutanoic acid Ethyl 3-((R)-1-benzyl-5-oxopyrrolidine-2-carboxamido)-2-hydroxy-4-phenylbutanoate was saponified in analogy to reaction step 1.2. ESI-MS [M+H]$^+$=397.2.

29.3 (2R)-1-benzyl-N-(4-(ethoxyamino)-3-hydroxy-4-oxo-1-phenylbutan-2-yl)-5-oxopyrrolidine-2-carboxamide The reaction was carried out in analogy to reaction step 1.3 by reacting 3-((R)-1-benzyl-5-oxopyrrolidine-2-carboxamido)-2-hydroxy-4-phenylbutanoic acid with O-ethylhydroxylamine hydrochloride using HATU (1.2 equivalents) as coupling reagent and DIPEA (6.8 equivalents) as base. ESI-MS [M+H]$^+$=440.2

29.4 (2R)-1-benzyl-N-(4-(ethoxyamino)-3,4-dioxo-1-phenylbutan-2-yl)-5-oxopyrrolidine-2-carboxamide IBX (2-iodoxybenzoic acid 432 mg, 0.694 mmol) was added to a solution of (2R)-1-benzyl-N-(4-(ethoxyamino)-3-hydroxy-4-oxo-1-phenylbutan-2-yl)-5-oxopyrrolidine-2-carboxamide (218 mg, 0.496 mmol) in DMSO (2 ml). After stiffing for 2 h at room temperature more IBX (123 mg, 0.198 mmol) was added and the stiffing was continued overnight. Saturated aqueous NaHCO$_3$ solution was added and the reaction mixture was diluted with water and dichloromethane. The precipitate formed was filtered off, the organic layer was separated and the aqueous layer extracted with dichloromethane. The combined organic layers were washed with water and dried (MgSO$_4$). The solvent was removed in vacuo, the resulting residue was redissolved in a small amount of dichloromethane and diethylether was added. The white precipitate formed was filtered, washed with diethylether and dried in vacuo. The crude product was dissolved in dichloromethane and treated with three drops of aqueous HCl (4M in dioxane). Removal of the solvent provided the title compound (8.2 mg, 0.015 mmol, 3.02% yield). ESI-MS [M+H]$^+$=438.2

Example 30

(2R)-1-benzyl-N-(4-(isopropoxyamino)-3,4-dioxo-1-phenylbutan-2-yl)-5-oxopyrrolidine-2-carboxamide The building block (R)-1-Benzyl-5-oxo-pyrrolidine-2-carboxylic acid used in the following example is commercially available.

30.1 Ethyl 3-((R)-1-benzyl-5-oxopyrrolidine-2-carboxamido)-2-hydroxy-4-phenylbutanoate The reaction was carried out in analogy to reaction step 1.1 by reacting (R)-1-benzyl-5-oxopyrrolidine-2-carboxylic acid and 4-ethoxy-3-hydroxy-4-oxo-1-phenylbutan-2-aminium chloride. ESI-MS [M+H]$^+$=425.2.

30.2 3-((R)-1-benzyl-5-oxopyrrolidine-2-carboxamido)-2-hydroxy-4-phenylbutanoic acid Ethyl 3-((R)-1-benzyl-5-oxopyrrolidine-2-carboxamido)-2-hydroxy-4-phenylbutanoate was saponified in analogy to reaction step 1.2. ESI-MS [M+H]$^+$=397.2.

30.3 (2R)-1-benzyl-N-(3-hydroxy-4-(isopropoxyamino)-4-oxo-1-phenylbutan-2-yl)-5-oxopyrrolidine-2-carboxamide The reaction can be carried out in analogy to reaction step 1.3 by reacting 3-((R)-1-benzyl-5-oxopyrrolidine-2-carboxamido)-2-hydroxy-4-phenylbutanoic acid with O-isopropylhydroxylamine.

30.4 (2R)-1-benzyl-N-(4-(isopropoxyamino)-3,4-dioxo-1-phenylbutan-2-yl)-5-oxopyrrolidine-2-carboxamide (2R)-1-benzyl-N-(3-hydroxy-4-(isopropoxyamino)-4-oxo-1-phenylbutan-2-yl)-5-oxopyrrolidine-2-carboxamide can be oxidized in analogy to reaction step 2.4.

Example 31

(2R)-1-benzyl-N-(4-(cyclopropylmethoxyamino)-3,4-dioxo-1-phenylbutan-2-yl)-5-oxopyrrolidine-2-carboxamide The building block (R)-1-Benzyl-5-oxo-pyrrolidine-2-carboxylic acid is commercially available.

31.1 Ethyl 3-((R)-1-benzyl-5-oxopyrrolidine-2-carboxamido)-2-hydroxy-4-phenylbutanoate The reaction was carried out in analogy to reaction step 1.1 by reacting (R)-1-benzyl-5-oxopyrrolidine-2-carboxylic acid and 4-ethoxy-3-hydroxy-4-oxo-1-phenylbutan-2-aminium chloride. ESI-MS [M+H]$^+$=425.2.

31.2 3-((R)-1-benzyl-5-oxopyrrolidine-2-carboxamido)-2-hydroxy-4-phenylbutanoic acid Ethyl 3-((R)-1-benzyl-5-oxopyrrolidine-2-carboxamido)-2-hydroxy-4-phenylbutanoate was saponified in analogy to reaction step 1.2. ESI-MS [M+H]$^+$=397.2.

31.3 (2R)-1-benzyl-N-(4-(cyclopropylmethoxyamino)-3-hydroxy-4-oxo-1-phenylbutan-2-yl)-5-oxopyrrolidine-2-carboxamide The reaction can be carried out in analogy to reaction step 1.3 by reacting 3-((R)-1-benzyl-5-oxopyrrolidine-2-carboxamido)-2-hydroxy-4-phenylbutanoic acid with O-(cyclopropylmethyl)hydroxylamine.

31.4 (2R)-1-benzyl-N-(4-(cyclopropylmethoxyamino)-3,4-dioxo-1-phenylbutan-2-yl)-5-oxopyrrolidine-2-carboxamide (2R)-1-benzyl-N-(4-(cyclopropylmethoxyamino)-3-hydroxy-4-oxo-1-phenylbutan-2-yl)-5-oxopyrrolidine-2-carboxamide can be oxidized in analogy to reaction step 2.4.

Example 32

(2R)-1-(2-fluorobenzyl)-N-(4-(methoxyamino)-3,4-dioxo-1-phenylbutan-2-yl)-5-oxopyrrolidine-2-carboxamide The building block (R)-1-(2-fluorobenzyl)-5-oxopyrrolidine-2-carboxylic acid was prepared in analogy to the procedure published by S. Marchalin et al., *Synthetic Communications* 28(19), 3619 (1998),

32.1 Ethyl 3-((R)-1-(2-fluorobenzyl)-5-oxopyrrolidine-2-carboxamido)-2-hydroxy-4-phenylbutanoate The reaction was carried out in analogy to reaction step 1.1 by reacting (R)-1-(2-fluorobenzyl)-5-oxopyrrolidine-2-carboxylic acid and 4-ethoxy-3-hydroxy-4-oxo-1-phenylbutan-2-aminium chloride. ESI-MS [M+H]$^+$=443.2.

32.2 3-((R)-1-(2-fluorobenzyl)-5-oxopyrrolidine-2-carboxamido)-2-hydroxy-4-phenylbutanoic acid Ethyl 3-((R)-1-(2-fluorobenzyl)-5-oxopyrrolidine-2-carboxamido)-2-hydroxy-4-phenylbutanoate was saponified in analogy to reaction step 1.2. ESI-MS [M+H]$^+$=415.2.

32.3 (2R)-1-(2-fluorobenzyl)-N-(3-hydroxy-4-(methoxyamino)-4-oxo-1-phenylbutan-2-yl)-5-oxopyrrolidine-2-carboxamide The reaction can be carried out in analogy to reaction step 1.3 by reacting 3-((R)-1-(2-fluorobenzyl)-5-oxopyrrolidine-2-carboxamido)-2-hydroxy-4-phenylbutanoic acid with O-methylhydroxylamine.

32.4 (2R)-1-(2-fluorobenzyl)-N-(4-(methoxyamino)-3,4-dioxo-1-phenylbutan-2-yl)-5-oxopyrrolidine-2-carboxamide (2R)-1-(2-fluorobenzyl)-N-(3-hydroxy-4-(methoxyamino)-4-oxo-1-phenylbutan-2-yl)-5-oxopyrrolidine-2-carboxamide can be oxidized in analogy to reaction step 2.4.

Example 33

(2R)-1-(2-chlorobenzyl)-N-(4-(methoxyamino)-3,4-dioxo-1-phenylbutan-2-yl)-5-oxopyrrolidine-2-carboxamide The building block (R)-1-(2-chlorobenzyl)-5-oxopyrrolidine-2-carboxylic acid was prepared in analogy to the procedure published by S. Marchalin et al., *Synthetic Communications* 28(19), 3619 (1998),

33.1 Ethyl 3-((R)-1-(2-chlorobenzyl)-5-oxopyrrolidine-2-carboxamido)-2-hydroxy-4-phenylbutanoate The reaction was carried out in analogy to reaction step 1.1 by reacting (R)-1-(2-chlorobenzyl)-5-oxopyrrolidine-2-carboxylic acid and 4-ethoxy-3-hydroxy-4-oxo-1-phenylbutan-2-aminium chloride. ESI-MS [M+H]$^+$=459.2.

33.2 3-((R)-1-(2-chlorobenzyl)-5-oxopyrrolidine-2-carboxamido)-2-hydroxy-4-phenylbutanoic acid Ethyl 3-((R)-1-(2-chlorobenzyl)-5-oxopyrrolidine-2-carboxamido)-2-hydroxy-4-phenylbutanoate was saponified in analogy to reaction step 1.2. ESI-MS [M+H]$^+$=431.1.

33.3 (2R)-1-(2-chlorobenzyl)-N-(3-hydroxy-4-(methoxyamino)-4-oxo-1-phenylbutan-2-yl)-5-oxopyrrolidine-2-carboxamide The reaction can be carried out in analogy to reaction step 1.3 by reacting 3-((R)-1-(2-chlorobenzyl)-5-oxopyrrolidine-2-carboxamido)-2-hydroxy-4-phenylbutanoic acid with O-methylhydroxylamine.

33.4 (2R)-1-(2-chlorobenzyl)-N-(4-(methoxyamino)-3,4-dioxo-1-phenylbutan-2-yl)-5-oxopyrrolidine-2-carboxamide (2R)-1-(2-chlorobenzyl)-N-(3-hydroxy-4-(methoxyamino)-4-oxo-1-phenylbutan-2-yl)-5-oxopyrrolidine-2-carboxamide can be oxidized in analogy to reaction step 2.4.

Example 34

N-(3,4-Dioxo-1-phenyl-4-(thiazol-2-ylamino)butan-2-yl)-2-(3-phenyl-1H-pyrazol-1-yl)nicotinamide

34.1: N-(3-Hydroxy-4-oxo-1-phenyl-4-(thiazol-2-ylamino)butan-2-yl)-2-(3-phenyl-1H-pyrazol-1-yl)nicotinamide

ESI-MS [M+H]$^+$=525.2.

34.2 N-(3,4-Dioxo-1-phenyl-4-(thiazol-2-ylamino)butan-2-yl)-2-(3-phenyl-1H-pyrazol-1-yl)nicotinamide ESI-MS [M+H+]: 523.15
$^1$H-NMR (400 MHz DMSO), δ [ppm]: 12.76 (broad, 1H), 9.12 (broad, 1H), 8.55 (d, 1H), 8.48 (d, 1H), 7.78 (m, 2H), 7.74 (m, 1H), 7.58 (m, 1H), 7.47 (m, 3H), 7.35 (m, 1H), 7.15 (m, 5H), 6.99 (d, 1H), 5.51 (m, 1H), 3.16 and 2.88 (each dd, 1H).

BIOLOGICAL INVESTIGATION OF INHIBITION OF CALPAIN AND CATHEPSINS

I Enzyme Inhibition in vitro:
Testing for blockade of the corresponding enzymic activities was carried out by means of kinetic fluorescence assays (excitation 390 nm, emission 460 nm).

Apparent Ki values were calculated from the experimentally determined IC$_{50}$ values by the Cheng-Prussoff relation assuming a reversible competitive enzyme inhibition. The Km values of the substrates used under the assay conditions indicated above were: 90 μM (Z-Phe-Arg-AMC, cathepsin B), 10 μM (Z-Gly-Pro-Arg-AMC, cathepsin K), 2 μM (Z-Phe-Arg-AMC, cathepsin L), and 30 μM (Z-Val-Val-Arg-AMC, cathepsin S). The indicated Ki values are averages of the inhibition constants calculated on the basis of 2 to 4 independent dose-effect plots.

The following assays were used:
1. Calpain I:
20 nM calpain-I—isolated from human erythrocytes (Calbiochem #208713), 100 μM Suc-Leu-Tyr-AMC (Bachem #I-1355) as substrate in buffer with 62 mM imidazole, 0.3 mM CaCl$_2$, 0.10% CHAPS, 0.05% BSA, 1 mM DTT at pH 7.3 and room temperature.
2. Cathepsin B:
0.25 nM cathepsin B—isolated from human liver (Calbiochem #219362), 100 μM Z-Phe-Arg-AMC (Bachem #I-1160) as substrate 50 mM MES, 2 mM EDTA, 0.05% Brij 35, 2.5 mM L-cysteine, pH 6.0, room temperature.
3. Cathepsin K:
3 nM cathepsin K—activated from recombinant human procathepsin K from *E. coli* (Calbiochem #342001), 10 μM Z-Gly-Pro-Arg-AMC (Biomol #P-142) as substrate in 50 mM MES, 2 mM EDTA, 0.05% Brij 35, 2.5 mM L-cysteine, pH 6.0, room temperature.

4. Cathepsin L:

1 nM cathepsin L—isolated from human liver (Calbiochem #219402), 2 μM Z-Phe-Arg-AMC (Bachem #I-1160) as substrate in 50 mM MES, 2 mM EDTA, 0.05% Brij 35, 2.5 mM L-cysteine, pH 6.0, room temperature.

5. Cathepsin S:

0.5 nM recombinant human cathepsin S from *E. coli* (Calbiochem #219343), 20 μM Z-Val-Val-Arg-AMC (Bachem #I-1540) as substrate in 50 mM MES, 2 mM EDTA, 0.05% Brij 35, 2.5 mM L-cysteine, pH 6.0, room temperature.

The results of the in vitro determination are indicated in Table 1. The following abbreviations are used in Table 1:

In the "Calpain activity" column, +++ stands for a calpain Ki (Ki(calpain)) of <200 nM, ++ means 200 nM≤Ki(calpain) of ≤300 nM, and + means 300 nM<Ki(Calpain)≤600 nM and o means 600 nM<Ki(Calpain)≤800 nM.

The "Sel. cat. B" column indicates the Ki(cathepsin B)/Ki(calpain) ratio. In this connection, +++ means a Ki(cathepsin B)/Ki(calpain) ratio of >10, ++ means 4<Ki(cathepsin B)/Ki(calpain)≤10, and + means 2≤Ki(cathepsin B)/Ki(calpain)≤4 and o means Ki(cathepsin B)/Ki(calpain)<2.

The "Sel. cat. K" column indicates the Ki(cathepsin K)/Ki(calpain) ratio. In this connection, +++ means a Ki(cathepsin K)/Ki(calpain) ratio of >10, ++ means 4<Ki(cathepsin K)/Ki(calpain)≤10, and + means 2≤Ki(cathepsin K)/Ki(calpain)≤4 and o means Ki(cathepsin K)/Ki(calpain)<2.

The "Sel. cat. L" column indicates the Ki(cathepsin L)/Ki(calpain) ratio. In this connection, +++ means a Ki(cathepsin L)/Ki(calpain) ratio of >50, ++ means 10<Ki(cathepsin L)/Ki(calpain)≤50, and + means 5≤Ki(cathepsin L)/Ki(calpain)≤10 and o means Ki(cathepsin L)/Ki(calpain)<5.

The "Sel. cat. S" column indicates the Ki(cathepsin S)/Ki(calpain) ratio. In this connection, +++ means a Ki(cathepsin S)/Ki(calpain) ratio of >50, ++ means 10<Ki(cathepsin S)/Ki(calpain)≤50, and + means 5≤Ki(cathepsin S)/Ki(calpain)≤10 and o means Ki(cathepsin S)/Ki(calpain)<5.

TABLE 1

| Example | Calpain activity | Sel cat. B | Sel cat. K | Sel cat. L | Sel cat. S | human cytCL | cyno cytCL |
|---|---|---|---|---|---|---|---|
| 1 | ++ | + | ++ | ++ | +++ | ++ | ++ |
| 2 | +++ | + | ++ | +++ | +++ | ++ | ++ |
| 3 | +++ | ++ | ++ | +++ | +++ | ++ | ++ |
| 4 | + | | + | ++ | + | ++ | ++ |
| 5 | + | | | ++ | ++ | ++ | ++ |
| 6 | ++ | + | ++ | ++ | +++ | ++ | ++ |
| 7 | +++ | ++ | + | ++ | +++ | ++ | ++ |
| 8 | +++ | | | + | ++ | ++ | ++ |
| 9 | n.a. | n.a. | n.a. | n.a. | n.a. | ++ | ++ |
| 10 | + | o | + | ++ | ++ | n.a. | n.a. |
| 11 | +++ | ++ | + | ++ | +++ | ++ | ++ |
| 12 | +++ | + | o | ++ | ++ | ++ | ++ |
| 13 | + | o | + | ++ | ++ | n.a. | n.a. |
| 16 | + | +++ | o | + | ++ | n.a. | n.a. |
| 17 | ++ | + | o | + | ++ | ++ | ++ |
| 18 | +++ | ++ | o | ++ | +++ | ++ | ++ |
| 19 | +++ | ++ | ++ | ++ | +++ | ++ | ++ |
| 20 | +++ | ++ | o | + | ++ | ++ | ++ |
| 21 | ++ | + | o | o | + | n.a. | n.a. |
| 22 | ++ | +++ | + | ++ | +++ | ++ | ++ |
| 23 | +++ | + | o | + | ++ | ++ | ++ |
| 24 | +++ | ++ | + | ++ | ++ | n.a. | n.a. |
| 25 | +++ | n.a. | n.a. | n.a. | n.a. | n.a. | n.a. |
| 28 (comp.) | +++ | n.a. | n.a. | n.a. | n.a. | + | − |
| 29 | o | +++ | ++ | ++ | ++ | n.a. | n.a. |
| 31 | +++ | + | o | o | ++ | n.a. | n.a. |

II Spectrin Molt-4 Assay to Determine Cellular Calpain Inhibition:

The following solutions and buffers were employed:

HBS (for 40 ml): 800 μl 1M HEPES; 2.16 ml 100 mM KCl; 4.8 ml 1M NaCl; 3.59 ml 5% glucose; 60 μl 1M MgSO$_4$; 400 μl 100 mM Na pyruvate, 28.19 ml water; pH 7.2-7.5.

lysis buffer (for 20 ml): 400 μl 1M Tris pH 8.2; 2.74 ml 1M NaCl; 520 μl 0.5M EDTA; 2 ml 10% triton X-100; 0.8 ml (=1:25) CompletePlus (1 tablet/2 ml H$_2$O); 200 μl 100 mM Pefabloc; 13.34 ml water, pH 8.2.

TBST (10×) (for 1 l): 100 mM Tris (12.1 g); 1.5M NaCl (87 g); 1% Tween 20 (10 g), adjusted to pH 8.

The assay design and procedure were as disclosed by Chatterjee; BMC 1998, 6, pp. 509-522; the EC$_{50}$ values are calculated from the percentage degradation of spectrin as a function of the dose.

Cell culture conditions: the molt-4 cells are maintained in RPMI 1640+Glutamax™ I medium (Gibco) with 10% FCS and 50 μg/ml gentamicin at 37° C., 5% CO$_2$ and split 1:15 twice a week.

Preparation of the molt-4 cells: the cells are washed, counted and taken up in a concentration of 2×10$^7$ cells/ml in HBS buffer.

Dilution of the inhibitor substances: all the inhibitors are dissolved in a concentration of 10$^{-2}$ M in DMSO. The stock solution is then diluted 1:15 in DMSO (=6.67×10$^{-4}$ M). Thereafter the stock solution diluted 1:15 is diluted 1:4 in DMSO in two steps (=1.67×10$^{-4}$ M and 4.17×10$^{-5}$ M). Thereafter, these three solutions are further diluted 1:50 in HBS buffer to give solutions having a concentration of 1.33× 10$^{-5}$ M, 3.36×10$^{-6}$ M and 8.34×10$^{-7}$ M.

Test mixture: for each mixture, 10$^6$ cells (see above) are introduced into a 1.5 ml Eppendorf tube. To these are added in each case 150 μl of the diluted substances (final conc. 10-5 M; 2.5×10$^{-6}$ M and 6.25×10$^{-7}$ M) and thoroughly mixed. A negative control and a positive control are used as controls. In this case, initially only 150 μl of HBS buffer is pipetted onto the cells. All the mixtures are incubated at 37° C., 5% CO$_2$ in an incubator for 10 min. Thereafter, except for the negative control, in each case CaCl$_2$ (final conc. 5 mM) and ionomycin (final conc. 5 μM) are added, thoroughly mixed and incubated at 37° C., 5% CO$_2$ in an incubator for 30 min. Then centrifuge at 700 g for 5 min. The supernatants are discarded and the pellets are taken up in 20 μl of lysis buffer. The mixtures are subsequently placed on ice for 30-60 min and then centrifuged at 15000 g for 15 min. The supernatants are removed and put into new Eppendorf tubes. The protein determination is then carried out thereon, e.g. with a MicroBCA assay (Pierce).

SDS-PAGE electrophoresis: 10 μg of total protein from each mixture are put into a new Eppendorf tube and, after pipetting in the same volume of 2×Tris-glycine SDS sample buffer (Invitrogen) and 1/10 volume of 1M DTT, thoroughly mixed and heated at 95° C. for 15 min. The solutions are briefly centrifuged and loaded onto a 6% SDS gel (Invitrogen). The gel is run at 100V with 1× Tris-glycine laemmli buffer (Biomol) until the lower band of the marker has reached the base of the gel.

Western blotting: the gel is removed from the apparatus and blotted onto nitrocellulose in 1× Tris-glycine transfer buffer (Invitrogen)+20% methanol with 1.5 A/cm$^2$ in a Fast-Blot chamber (Biometra) for 30 min. The nitrocellulose filter is removed, briefly washed in TBST buffer and blocked in TBST/5% milk powder for 1 h at RT (room temperature). The blocked nitrocellulose is then incubated with an anti-spectrin Ab (Chemicon) (1:10000 in TBST/5% milk powder) at RT for 3 h or at 4° C. overnight. The nitrocellulose is washed 3× in TBST buffer. It is then incubated with anti-mouse IgG (POD) antibody (Sigma) (1:10000 in TBST/5% milk powder) at room temperature for 1 h.

The nitrocellulose is then washed 5× in TBST buffer. In the next step, 5 ml of prepared solution of the SuperSignal® West Pico chemiluminescence substrate (Pierce) are put on the filter and incubated for 5 min. The nitrocellulose is then taken out of the solution, gently dabbed dry and inserted into a development folder film (Tropix). A digital image analysis system (VersaDoc, Biorad) is used to record and quantify the ECL (QuantityOne), and the percentage degradation of spectrin is calculated from the data. Graph-pad prism is used to fit the percentage spectrum degradation as a function of the dose to a sigmoidal dose-effect plot (top fixed at 100% and bottom at 0%), and the EC 50% is calculated.

III Assay for Determining Cytosolic Clearance of Compounds of Formula I:

For comparison purposes data measured with human liver cytosol were contrasted with those obtained with cynomolgus monkey liver cytosol.

0.5 µM of a compound to be tested was incubated with 1 mg/ml of human liver cytosol as well as monkey liver cytosol at 37° C. in 0.5 M of phosphate buffer at pH 7.5 while shaking (commercial sources: female cynomolgus liver cytosol from Tebu bio, human liver cytosol from BDgentest).

In each case aliquots of 65 µl were taken after 0, 5, 10 and 15 min and transferred into wells of a wellplate which were immediately filled with 130 µl of ethanol to stop the reaction. The samples were kept frozen until analysis on a LC/MS/MS system (Applied Biosystems SCIEX 4000).

Read out parameters were the loss of parent compounds, from which the half life periods ($T_{1/2}$) were calculated from. Based on these data the parameters cytosolic clearance (cytCL), scaled clearance (CLs) and predicted clearance (CLp) were calculated using the following equations:

$$cytCL = (\ln 2/T_{1/2}) \times [\text{cytosolic protein}] \times 1000 \quad 1)$$

$$CLs = cytCL \times [\text{cytosolic yield}]/1,000,000 \times 60 \quad 2)$$

$$CLp = (CLs + \text{hepatic plasma flow})/\text{hepatic plasma flow}/CLs \quad 3)$$

To assess the stability of the compounds tested the clearance ranges were adjusted to the hepatic plasma flow of the different species according to the following scheme:

stable=from 0 to about ⅓ of the hepatic plasma flow;
moderately stable=from about ⅓ to about ⅔ of the hepatic plasma flow;
instable=more than ⅔ of the hepatic plasma flow.

Based on this adjustment the following qualifiers were assigned to evaluate the cytosolic stabilities of the compounds tested:

| cytCL | symbol | human | cynomolgus monkey (cyno) |
|---|---|---|---|
| stable | ++ | 0-14 µl/min/mg | 0-18 µl/min/mg |
| moderately stable | + | 14-70 µl/min/mg | 18-90 µl/min/mg |
| instable | − | >70 µl/min/mg | >90 µl/min/mg |

The cytCL data obtained this way for the compounds of the Examples 1 to 18 are depicted in Table 1 above. As can be seen from Table 1 the compounds of formula I according to the invention feature improved stabilities over the related compound of WO 08/080969 having an unsubstituted carboxamide moiety (comparative Example 18).

IV In-vitro Assay for Determining Degradation of Compounds I into the Corresponding Hydroxyamide Metabolites in Hepatocytes:

Each compound to be tested (10 µl) was incubated in monkey and also in human hepatocytes to determine the concentration ratio of hydroxyamide metabolite to the compound of formula I as parent compound. Incubations were carried out at 37° C. for 0 and 4 hours in a 24-well plate, each well holding 0.5 ml hepatocyte medium with about 500,000 cells/ml. At the end of each time point, 1 ml of acetonitrile/ethanol (1/1, v/v) was added to each well to quench the reaction. The solutions were vortexed and mixed thoroughly. An aliquot was subjected to LC-UV-MS/MS analysis at UV wavelength of 254 nm Identities of compounds I tested and their corresponding hydroxyamide metabolites were confirmed by MS/MS analysis and by comparison with synthetic standards. UV areas for each test compound and its hydroxylamine metabolite were integrated. The concentration ratios of hydroxyamide metabolites to parent compounds (M/P ratios) were determined as ratios of the UV areas of metabolites to those of the compounds I, assuming that extinction coefficients $\epsilon_P$ and $\epsilon_M$ are approximately identical. The M/P ratios obtained this way for incubations terminated after 4 hours are shown in Table 2.

TABLE 2

| | M/P ratio | |
|---|---|---|
| Example | cyno | human |
| 2 | <0.1 | <0.1 |
| 11 (comp.) | 3.4 | 8.0 |

As can be seen from Table 2 the reductive degradation of the compound of Example 2 according to the invention is much slower in both human and cyno hepatocytes as compared to the related compound of WO 08/080969 (comparative Example 11).

V In-vivo Determination of the Ratio of Hydroxyamide Metabolite to the Parent Compound I in Plasma of Cynomolgus Monkeys The tested compounds were prepared as a solution for either intravenous or oral administration to groups of female cynomolgus monkeys. For intravenous dosing, the compounds were prepared in a 10% DMSO/PEG-400 vehicle at a concentration of 2 mg/ml. For oral dosing, the compounds were prepared in a lipid based vehicle at a concentration of 3 mg/ml. Groups of three monkeys received either a 1 mg/kg (0.5 ml/kg) intravenous dose or a 3 mg/kg (1 ml/kg) oral dose. The intravenous dose was administered as a slow bolus in a saphenous vein; the oral dose was administered by gastric intubation and was followed by ~5 ml water. Serial blood samples were obtained from each animal at selected time points up to 24 hours after drug administration. Plasma was separated from the blood by centrifugation and stored frozen (<−15 C) until analysis. Parent compounds I and the selected metabolites were separated from plasma using protein precipitation with mixture of methanol, acetonitrile and water. The supernatant was evaporated to dryness with a stream of dry nitrogen. The samples were reconstituted with an aliquot of mobile phase, followed by quantification by HPLC-MS/MS. Standard curves for both parent and the selected metabolites were prepared from authentic standards in blank monkey plasma; standards were analyzed simultaneously with the samples. The plasma concentration of each sample was calculated by least squares linear regression analysis of the peak area ratio (parent or metabolite/internal standard) of the spiked plasma standards versus concentration.

Peak plasma concentrations ($C_{max}$) and the time to peak plasma concentration ($T_{max}$) were read directly from the plasma concentration data for each monkey. The plasma concentration data for both parent and metabolite were submitted to multi-exponential curve fitting using WinNonlin. The area under the plasma concentration-time curve from 0 to t hours (time of the last measurable plasma concentration) after dosing ($AUC_{0-t}$) was calculated using the linear trapezoidal rule for the plasma concentration-time profiles. The residual area extrapolated to infinity, determined as the final measured plasma concentration (Ct) divided by the terminal elimination rate constant (β), was added to $AUC_{0-t}$ to produce the total area under the curve ($AUC_{0-inf}$). The apparent total plasma clearance ($CL_p$) was calculated by dividing the administered dose by the $AUC_{0-inf}$. The initial volume of distribution ($V_c$) was calculated as the dose divided by the extrapolated concentration at time=0 ($C_0$). The volume of distribution at steady state, $V_{ss}$, was estimated as a product of the plasma clearance ($CL_p$) and the mean residence time (MRT); the terminal-phase volume of distribution ($V_β$), was derived from the plasma clearance value ($CL_p$) divided by the plasma elimination rate constant (β). The bioavailability was calculated as the dose-normalized $AUC_{0-inf}$ from the oral dose divided by the corresponding value derived from the intravenous dose. Metabolite to parent ratios were calculated as the $C_{max}$ (metabolite)/$C_{max}$ (parent) or AUC(metabolite)/AUC (parent) for the peak concentrations and area under the curve, respectively. Results obtained in these ways are shown in Table 3.

TABLE 3

| Example | Bioavailability | M/P ratio |
|---|---|---|
| 2 | 59% | <0.05 |
| 11 (comp.) | 0.2-3% [1] | 7 |

[1] Depending on the dose and the vehicle used

As can be seen from Table 3 in comparison to the comparative compound disclosed in WO 08/080969 (Example 11) the compound of the invention from Example 2 exhibits a much higher stability against AKR-mediated reduction and in addition an almost 300 times higher oral bioavailability.

The invention claimed is:

1. A carboxamide compound of the formula I

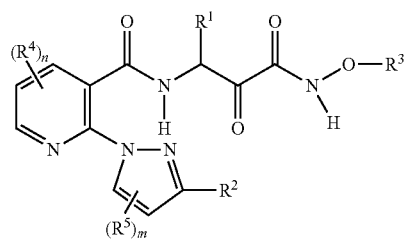

(I)

in which
R¹ is benzyl, which may be unsubstituted or carry 1 or 2 identical or different radicals selected from the group consisting of halogen, $C_1$-$C_2$-alkyl, and $C_1$-$C_2$-alkoxy;
R² is selected from the group consisting of aryl, aryl-$C_1$-$C_6$-alkyl, and aryl-$C_2$-$C_6$-alkenyl, where aryl in the last 3 radicals mentioned may be unsubstituted or carry 1, 2, 3, or 4 identical or different radicals $R^{2c}$;
where
$R^{2c}$ is selected independently of one another from the group consisting of halogen, $C_1$-$C_2$-alkyl, where the alkyl may be partly or completely halogenated, $C_1$-$C_2$-alkoxy, and —$(CH_2)_p$—$NR^{c6}R^{c7}$ with p=0, 1, or 2, where
$R^{c6}$ is selected from the group consisting of H and $C_1$-$C_4$-alkyl, and
$R^{c7}$ is selected from the group consisting of H and $C_1$-$C_4$-alkyl;
R³ is selected from the group consisting of $C_1$-$C_6$-alkyl, $C_1$-$C_3$-haloalkyl, $C_3$-$C_5$-alkenyl, $C_3$-$C_5$-alkynyl, $C_3$-$C_6$-cycloalkyl, $C_3$-$C_6$-cycloalkyl-$C_1$-$C_2$-alkyl, $C_1$-$C_2$-alkoxy-$C_1$-$C_2$-alkyl, aryl, and aryl-$C_1$-$C_3$-alkyl;
R⁴ and R⁵ are selected independently of one another from the group consisting of halogen, $NH_2$, CN, $CF_3$, $CHF_2$, $CH_2F$, O—$CF_3$, O—$CHF_2$, O—$CH_2F$, COOH, $OCH_2COOH$, $C_1$-$C_2$-alkyl, $C_1$-$C_2$-alkoxy, $C_1$-$C_2$-alkoxy-$C_1$-$C_2$-alkyl, $C_1$-$C_2$-alkylthio, and $CH_2NRR'$, where
R and R' are selected independently of one another from the group consisting of hydrogen and $C_1$-$C_4$-alkyl;
m is 0, 1, or 2; and
n is 0, 1, or 2;
or a tautomer thereof, or a pharmaceutically acceptable salt thereof.

2. The carboxamide compound of claim 1, in which m is 0 or 1 and, when m=1, R⁵ is selected from the group consisting of F, Cl, CN, $CF_3$, $C_1$-$C_2$-alkyl, and $C_1$-$C_2$-alkoxy.

3. The carboxamide compound of claim 1, in which n is 0 or 1 and, when n=1, R⁴ is selected from the group consisting of F, Cl, CN, $CF_3$, $C_1$-$C_2$-alkyl, and $C_1$-$C_2$-alkoxy.

4. The carboxamide compound of claim 1, in which R³ is selected from the group consisting of methyl, ethyl, n-propyl, isopropyl, propenyl, but-2-enyl, but-3-enyl, propinyl, cyclopropyl, cyclobutyl, cyclopentyl, and cyclopropyl-methyl.

5. The carboxamide compound of claim 1, in which R³ is selected from the group consisting of $C_1$-$C_3$-alkyl, $C_1$-$C_3$-haloalkyl, $C_3$-$C_5$-alkenyl, $C_3$-$C_5$-alkynyl, $C_3$-$C_6$-cycloalkyl, $C_1$-$C_2$-alkoxy-$C_1$-$C_2$-alkyl, aryl, and aryl-$C_1$-$C_3$-alkyl.

6. The carboxamide compound of claim 5, in which R³ is selected from the group consisting of methyl, ethyl, propenyl, but-2-enyl, but-3-enyl, propinyl, cyclopropanyl, cyclopropanyl-methyl, phenyl, and benzyl.

7. The carboxamide compound of claim 1, in which R² is phenyl, which may be unsubstituted or carry 1 or 2 identical or different radicals $R^{2c}$.

8. The carboxamide compound of claim 1, in which R² is phenyl, which may be unsubstituted or carry 1 or 2 identical or different radicals selected from the group consisting of halogen, $C_1$-$C_2$-alkyl, $C_1$-$C_2$-alkoxy, and —$(CH_2)_p$—$NR^{c6}R^{c7}$ with p=0, 1 or 2, where
$R^{c6}$ is selected from the group consisting of H and $C_1$-$C_4$-alkyl, and
$R^{c7}$ is selected from the group consisting of H and $C_1$-$C_4$-alkyl.

9. The carboxamide compound of claim 1, which has the S configuration at the carbon atom carrying the group R¹.

10. A carboxamide compound which is selected from the group consisting of:
2-[3-(4-Fluorophenyl)-1H-pyrazol-1-yl]-N-[4-(methoxyamino)-3,4-dioxo-1-phenylbutan-2-yl]pyridine-3-carboxamide;

(2R)-2-[3-(4-Fluorophenyl)-1H-pyrazol-1-yl]-N-[4-(methoxyamino)-3,4-dioxo-1-phenylbutan-2-yl]pyridine-3-carboxamide;
(2S)-2-[3-(4-Fluorophenyl)-1H-pyrazol-1-yl]-N-[4-(methoxyamino)-3,4-dioxo-1-phenylbutan-2-yl]pyridine-3-carboxamide;
N-(4-(Methoxyamino)-3,4-dioxo-1-phenylbutan-2-yl)-2-(3-phenyl-1H-pyrazol-1-yl)nicotinamide;
(2R)—N-(4-(Methoxyamino)-3,4-dioxo-1-phenylbutan-2-yl)-2-(3-phenyl-1H-pyrazol-1-yl)nicotinamide;
(2S)—N-(4-(Methoxyamino)-3,4-dioxo-1-phenylbutan-2-yl)-2-(3-phenyl-1H-pyrazol-1-yl)nicotinamide;
2-(4-Fluoro-3-phenyl-1H-pyrazol-1-yl)-N-(4-(methoxyamino)-3,4-dioxo-1-phenylbutan-2-yl)nicotinamide;
(2R)-2-(4-Fluoro-3-phenyl-1H-pyrazol-1-yl)-N-(4-(methoxyamino)-3,4-dioxo-1-phenylbutan-2-yl)nicotinamide;
(2S) 2-(4-Fluoro-3-phenyl-1H-pyrazol-1-yl)-N-(4-(methoxyamino)-3,4-dioxo-1-phenylbutan-2-yl)nicotinamide;
N-[4-(Methoxyamino)-3,4-dioxo-1-phenylbutan-2-yl]-2-(4-methyl-3-phenyl-1H-pyrazol-1-yl)pyridine-3-carboxamide;
(2R)—N-[4-(Methoxyamino)-3,4-dioxo-1-phenylbutan-2-yl]-2-(4-methyl-3-phenyl-1H-pyrazol-1-yl)pyridine-3-carboxamide;
(2S)—N-[4-(Methoxyamino)-3,4-dioxo-1-phenylbutan-2-yl]-2-(4-methyl-3-phenyl-1H-pyrazol-1-yl)pyridine-3-carboxamide;
N-(1-(4-Fluorophenyl)-4-(methoxyamino)-3,4-dioxo-butan-2-yl)-2-(3-phenyl-1H-pyrazol-1-yl)nicotinamide;
(2R)—N-(1-(4-Fluorophenyl)-4-(methoxyamino)-3,4-dioxo-butan-2-yl)-2-(3-phenyl-1H-pyrazol-1-yl)nicotinamide;
(2S)—N-(1-(4-Fluorophenyl)-4-(methoxyamino)-3,4-dioxo-butan-2-yl)-2-(3-phenyl-1H-pyrazol-1-yl)nicotinamide;
N-(1-(3-Fluorophenyl)-4-(methoxyamino)-3,4-dioxobutan-2-yl)-2-(3-phenyl-1H-pyrazol-1-yl)nicotinamide;
(2R)—N-(1-(3-Fluorophenyl)-4-(methoxyamino)-3,4-dioxobutan-2-yl)-2-(3-phenyl-1H-pyrazol-1-yl)nicotinamide;
(2S)—N-(1-(3-Fluorophenyl)-4-(methoxyamino)-3,4-dioxobutan-2-yl)-2-(3-phenyl-1H-pyrazol-1-yl)nicotinamide;
N-(4-(Ethoxyamino)-3,4-dioxo-1-phenylbutan-2-yl)-2-(3-phenyl-1H-pyrazol-1-yl)nicotinamide;
(2R)—N-(4-(Ethoxyamino)-3,4-dioxo-1-phenylbutan-2-yl)-2-(3-phenyl-1H-pyrazol-1-yl)nicotinamide;
(2S)—N-(4-(Ethoxyamino)-3,4-dioxo-1-phenylbutan-2-yl)-2-(3-phenyl-1H-pyrazol-1-yl)nicotinamide;
N-(4-(Allyloxyamino)-3,4-dioxo-1-phenylbutan-2-yl)-2-(3-phenyl-1H-pyrazol-1-yl)nicotinamide;
(2R)—N-(4-(Allyloxyamino)-3,4-dioxo-1-phenylbutan-2-yl)-2-(3-phenyl-1H-pyrazol-1-yl)nicotinamide;
(2S)—N-(4-(Allyloxyamino)-3,4-dioxo-1-phenylbutan-2-yl)-2-(3-phenyl-1H-pyrazol-1-yl)nicotinamide;
N-(4-(Methoxyamino)-1-(4-methoxyphenyl)-3,4-dioxo-butan-2-yl)-2-(3-phenyl-1H-pyrazol-1-yl)nicotinamide;
(2R)—N-(4-(Methoxyamino)-1-(4-methoxyphenyl)-3,4-dioxo-butan-2-yl)-2-(3-phenyl-1H-pyrazol-1-yl)nicotinamide;
(2S)—N-(4-(Methoxyamino)-1-(4-methoxyphenyl)-3,4-dioxo-butan-2-yl)-2-(3-phenyl-1H-pyrazol-1-yl)nicotinamide;
2-(4-Chloro-3-phenyl-1H-pyrazol-1-yl)-N-(4-(methoxyamino)-3,4-dioxo-1-phenylbutan-2-yl)nicotinamide;
(2R)-2-(4-Chloro-3-phenyl-1H-pyrazol-1-yl)-N-(4-(methoxyamino)-3,4-dioxo-1-phenylbutan-2-yl)nicotinamide;
(2S)-2-(4-Chloro-3-phenyl-1H-pyrazol-1-yl)-N-(4-(methoxyamino)-3,4-dioxo-1-phenylbutan-2-yl)nicotinamide;
N-[4-(Isopropoxyamino)-3,4-dioxo-1-phenyl-2-butanyl]-2-(3-phenyl-1H-pyrazol-1-yl)nicotinamide;
(2R)—N-[4-(Isopropoxyamino)-3,4-dioxo-1-phenyl-2-butanyl]-2-(3-phenyl-1H-pyrazol-1-yl)nicotinamide;
(2S)—N-[4-(Isopropoxyamino)-3,4-dioxo-1-phenyl-2-butanyl]-2-(3-phenyl-1H-pyrazol-1-yl)nicotinamide;
N-[3,4-Dioxo-1-phenyl-4-(propoxyamino)-2-butanyl]-2-(3-phenyl-1H-pyrazol-1-yl)nicotinamide;
(2R)—N-[3,4-Dioxo-1-phenyl-4-(propoxyamino)-2-butanyl]-2-(3-phenyl-1H-pyrazol-1-yl)nicotinamide;
(2S)—N-[3,4-Dioxo-1-phenyl-4-(propoxyamino)-2-butanyl]-2-(3-phenyl-1H-pyrazol-1-yl)nicotinamide;
2-(3-{4-[(Diethylamino)methyl]phenyl}-1H-pyrazol-1-yl)-N-[4-(methoxyamino)-3,4-dioxo-1-phenyl-2-butanyl]nicotinamide;
(2R)-2-(3-{4-[(Diethylamino)methyl]phenyl}-1H-pyrazol-1-yl)-N-[4-(methoxyamino)-3,4-dioxo-1-phenyl-2-butanyl]nicotinamide;
(2S)-2-(3-{4-[(Diethylamino)methyl]phenyl}-1H-pyrazol-1-yl)-N-[4-(methoxyamino)-3,4-dioxo-1-phenyl-2-butanyl]nicotinamide;
N-(4-{[(2-Methyl-2-propanyl)oxy]amino}-3,4-dioxo-1-phenyl-2-butanyl)-2-(3-phenyl-1H-pyrazol-1-yl)nicotinamide;
(2R)—N-(4-{[(2-Methyl-2-propanyl)oxy]amino}-3,4-dioxo-1-phenyl-2-butanyl)-2-(3-phenyl-1H-pyrazol-1-yl)nicotinamide;
(2S)—N-(4-{[(2-Methyl-2-propanyl)oxy]amino}-3,4-dioxo-1-phenyl-2-butanyl)-2-(3-phenyl-1H-pyrazol-1-yl)nicotinamide;
N-{4-[(Cyclopentyloxy)amino]-3,4-dioxo-1-phenyl-2-butanyl}-2-(3-phenyl-1H-pyrazol-1-yl)nicotinamide;
(2R)—N-{4-[(Cyclopentyloxy)amino]-3,4-dioxo-1-phenyl-2-butanyl}-2-(3-phenyl-1H-pyrazol-1-yl)nicotinamide;
(2S)—N-{4-[(Cyclopentyloxy)amino]-3,4-dioxo-1-phenyl-2-butanyl}-2-(3-phenyl-1H-pyrazol-1-yl)nicotinamide;
N-[4-(Ethoxyamino)-1-(4-fluorophenyl)-3,4-dioxo-2-butanyl]-2-(3-phenyl-1H-pyrazol-1-yl)nicotinamide;
(2R)—N-[4-(Ethoxyamino)-1-(4-fluorophenyl)-3,4-dioxo-2-butanyl]-2-(3-phenyl-1H-pyrazol-1-yl)nicotinamide;
(2S)—N-[4-(Ethoxyamino)-1-(4-fluorophenyl)-3,4-dioxo-2-butanyl]-2-(3-phenyl-1H-pyrazol-1-yl)nicotinamide;
N-[4-(Ethoxyamino)-3,4-dioxo-1-phenyl-2-butanyl]-2-(4-fluoro-3-phenyl-1H-pyrazol-1-yl)nicotinamide;
(2R)—N-[4-(Ethoxyamino)-3,4-dioxo-1-phenyl-2-butanyl]-2-(4-fluoro-3-phenyl-1H-pyrazol-1-yl)nicotinamide;
(2S)—N-[4-(Ethoxyamino)-3,4-dioxo-1-phenyl-2-butanyl]-2-(4-fluoro-3-phenyl-1H-pyrazol-1-yl)nicotinamide;
N-{4-[(Cyclobutyloxy)amino]-3,4-dioxo-1-phenyl-2-butanyl}-2-(3-phenyl-1H-pyrazol-1-yl)nicotinamide;

(2R)—N-{4-[(Cyclobutyloxy)amino]-3,4-dioxo-1-phenyl-2-butanyl}-2-(3-phenyl-1H-pyrazol-1-yl)nicotinamide;
(2S)—N-{4-[(Cyclobutyloxy)amino]-3,4-dioxo-1-phenyl-2-butanyl}-2-(3-phenyl-1H-pyrazol-1-yl)nicotinamide;
N-{4-[(2,2-Dimethylpropoxy)amino]-3,4-dioxo-1-phenyl-2-butanyl}-2-(3-phenyl-1H-pyrazol-1-yl)nicotinamide;
(2R)—N-{4-[(2,2-Dimethylpropoxy)amino]-3,4-dioxo-1-phenyl-2-butanyl}-2-(3-phenyl-1H-pyrazol-1-yl)nicotinamide;
(2S)—N-{4-[(2,2-Dimethylpropoxy)amino]-3,4-dioxo-1-phenyl-2-butanyl}-2-(3-phenyl-1H-pyrazol-1-yl)nicotinamide;
N-{4-[(Cyclopropylmethoxy)amino]-3,4-dioxo-1-phenyl-2-butanyl}-2-(3-phenyl-1H-pyrazol-1-yl)nicotinamide;
(2R)—N-{4-[(Cyclopropylmethoxy)amino]-3,4-dioxo-1-phenyl-2-butanyl}-2-(3-phenyl-1H-pyrazol-1-yl)nicotinamide;
(2S)—N-{4-[(Cyclopropylmethoxy)amino]-3,4-dioxo-1-phenyl-2-butanyl}-2-(3-phenyl-1H-pyrazol-1-yl)nicotinamide;
N-[4-(Ethoxyamino)-1-(4-methoxyphenyl)-3,4-dioxo-2-butanyl]-2-(3-phenyl-1H-pyrazol-1-yl)nicotinamide;
(2R)—N-[4-(Ethoxyamino)-1-(4-methoxyphenyl)-3,4-dioxo-2-butanyl]-2-(3-phenyl-1H-pyrazol-1-yl)nicotinamide;
(2S)—N-[4-(Ethoxyamino)-1-(4-methoxyphenyl)-3,4-dioxo-2-butanyl]-2-(3-phenyl-1H-pyrazol-1-yl)nicotinamide;
2-[3-(2-Fluorophenyl)-1H-pyrazol-1-yl]-N-[4-(methoxyamino)-3,4-dioxo-1-phenyl-2-butanyl]nicotinamide;
(2R)-2-[3-(2-Fluorophenyl)-1H-pyrazol-1-yl]-N-[4-(methoxyamino)-3,4-dioxo-1-phenyl-2-butanyl]nicotinamide;
(2S)-2-[3-(2-Fluorophenyl)-1H-pyrazol-1-yl]-N-[4-(methoxyamino)-3,4-dioxo-1-phenyl-2-butanyl]nicotinamide;
N-[4-(Methoxyamino)-3,4-dioxo-1-phenyl-2-butanyl]-2-{3-[3-(trifluoromethyl)phenyl]-1H-pyrazol-1-yl}nicotinamide;
(2R)—N-[4-(Methoxyamino)-3,4-dioxo-1-phenyl-2-butanyl]-2-{3-[3-(trifluoromethyl)phenyl]-1H-pyrazol-1-yl}nicotinamide; and
(2S)—N-[4-(Methoxyamino)-3,4-dioxo-1-phenyl-2-butanyl]-2-{3-[3-(trifluoromethyl)phenyl]-1H-pyrazol-1-yl}nicotinamide;

or a tautomer thereof, or a pharmaceutically acceptable salt thereof.

11. A pharmaceutical composition comprising at least one carboxamide compound of claim 1 and a carrier.

* * * * *